United States Patent [19]

Ishizuka et al.

[11] Patent Number: 5,698,137
[45] Date of Patent: Dec. 16, 1997

[54] OPTICALLY ACTIVE DIHYDROPYRAN DERIVATIVE, AND LIQUID CRYSTAL COMPOSITION, LIQUID CRYSTAL DEVICE, AND RACEMIC MIXTURE COMPRISING THE DERIVATIVE

[75] Inventors: Tatsushi Ishizuka; Mitsunori Takeda; Masaaki Namekawa; Keizou Itoh, all of Ibaraki-ken, Japan

[73] Assignee: Kashima Oil Company, Tokyo, Japan

[21] Appl. No.: 632,118

[22] Filed: Apr. 15, 1996

[30] Foreign Application Priority Data

May 1, 1995 [JP] Japan ..................... 7-107190

[51] Int. Cl.$^6$ .............. C09K 19/34; G02F 1/13; C07D 309/30; C07D 309/22
[52] U.S. Cl. ............ 252/299.61; 549/416; 549/417; 549/420; 549/370; 546/282.1; 544/238; 544/239; 544/318; 544/333; 544/405; 349/182
[58] Field of Search ................. 549/416, 417, 549/420, 370; 252/299.61; 546/282.1; 544/238, 239, 318, 333, 405

[56] References Cited

U.S. PATENT DOCUMENTS

| | | |
|---|---|---|
| 4,818,431 | 4/1989 | Eldenschiak et al. |
| 5,437,814 | 8/1995 | Koden et al. ............ 252/299.01 |
| 5,443,755 | 8/1995 | Namekawa et al. ........ 252/299.61 |
| 5,595,684 | 1/1997 | Namekawa et al. ........ 252/299.61 |

FOREIGN PATENT DOCUMENTS

| | | |
|---|---|---|
| 0 409 066 | 1/1991 | European Pat. Off. |
| 0 684 246 | 11/1995 | European Pat. Off. |

OTHER PUBLICATIONS

Patent Abstracts of Japan, vol. 17, No. 647 (C–1135), Dec. 2, 1993, JP–A–05 208969, Aug. 20, 1993.
Tetrahedron: Asymmetry, vol. 4, No. 5, pp. 1059–1062, Jan. 18, 1993, Takashi Yamazaki, et al., "Preparation of 6–Deoxy–6,6,6–Trifluro–D–Mannose and D–Allose From Enzymatically Resolved 2–Butenolides".

*Primary Examiner*—Nicky Chan
*Attorney, Agent, or Firm*—Oblon, Spivak, McClelland, Maier & Neustadt, P.C.

[57] ABSTRACT

A 2H-5,6-optically active dihydropyran derivative represented by the general formula (I) or (I'):

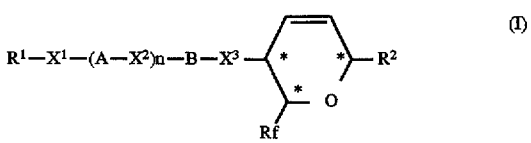

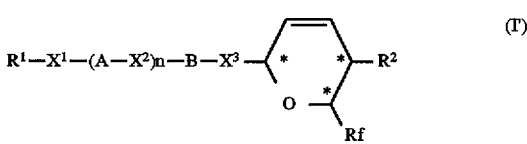

wherein Rf represents a fluoroalkyl group having 1 or 2 carbon atoms; a liquid crystal composition and a liquid crystal device comprising the derivative; and a racemic mixture comprising at least one type of the derivative. The derivative is a novel compound which exhibits the liquid crystal property by itself or can be used as an excellent dopant providing a high speed response to a composition comprising it even when the compound does not exhibit the liquid crystal property by itself. The derivative also exhibits a large spontaneous polarization.

6 Claims, No Drawings

OPTICALLY ACTIVE DIHYDROPYRAN DERIVATIVE, AND LIQUID CRYSTAL COMPOSITION, LIQUID CRYSTAL DEVICE, AND RACEMIC MIXTURE COMPRISING THE DERIVATIVE

FIELD OF THE INVENTION

The present invention relates to an optically active dihydropyran derivative, a liquid crystal composition comprising the derivative, and a liquid crystal device comprising the derivative. More particularly, the present invention relates to a novel optically active dihydropyran derivative which is advantageously used as a liquid crystal material for a display device or an electro-optical device, and a liquid crystal composition, a liquid crystal device, and a racemic mixture comprising the derivative.

PRIOR ART OF THE INVENTION

The field of application of liquid crystals is recently expanding to various types of display device, electro-optical device, and liquid crystal sensor. In accordance with the expansion in the field of application, liquid crystals having various structures are proposed. More particularly, nematic liquid crystals are the main liquid crystal material for display devices at present. Nematic liquid crystal material are used in simple matrix display devices of the TN type or the STN type and in active matrix display devices of the TFT type in which a thin film transistor is provided to each display element. However, the nematic liquid crystals have a drawback in that the response time is essentially slow (the order of millisecond) because the driving force is based on the weak interaction between the anisoptropy of dielectric constant of the liquid crystal material and the electric field. Therefore, the nematic liquid crystal cannot advantageously be used as the material for a large area display device which requires a high speed response.

On the other hand, a ferroelectric liquid crystal which was first synthesized by R. B. Meyer et al. in 1975 exhibits spontaneous polarization, and a large driving force is obtained because the spontaneous polarization causes the direct interaction with the electric field. The ferroelectric liquid crystal attracted attention when N. A. Clark reported in 1980 that a surface stabilized ferroelectric liquid crystal device (SSFLCD) exhibited a high speed response of the order of microsecond and a memory effect. Many ferroelectric liquid crystal compounds have been synthesized since that time.

The response time π of a ferroelectric liquid crystal can be expressed by the equation π=η(Ps.E). In the equation, η represents the rotational viscosity, Ps represents the spontaneous polarization, and E represents the strength of an electric field. Based the equation, a liquid crystal having a smaller viscosity and a larger spontaneous polarization has been the target of the development to achieve a high speed response. Other properties such as chemical stability and a wide range in the temperature for use are also required for a liquid crystal material. Satisfying these requirements with a single compound has been difficult. Therefore, a ferroelectric liquid crystalline composition exhibiting the chiral smectic C (SmC*) phase and having the desired properties has heretofore been obtained by mixing a plurality of compounds exhibiting the SmC* phase or by adding an optically active compound to a base liquid crystal exhibiting the smectic C (SmC) phase and having a low viscosity.

When the second of the above methods is used, it is not required that the chiral dopant added to the base liquid crystal exhibit the SmC* phase by itself. Instead, it is required that the chiral dopant has a good compatibility with the base liquid crystal, induce a large spontaneous polarization, and does not cause increase in the viscosity.

The spontaneous polarization is considered to take place because free rotation of the dipolemoment in the direction perpendicular to the longitudinal molecular axis around the longitudinal molecular axis is restricted by the effect of the asymmetric carbon. Therefore, attempts to increase the spontaneous polarization have been made by (1) bringing the dipole part to a position closer to the skeleton part called core, (2) bringing the dipole part and the asymmetric carbon to positions closer to each other, or (3) restricting the free rotation around the longitudinal molecular axis by attaching a sterically large substituent to the asymmetric carbon. It is also recently reported that the free rotation is effectively restricted in a compound having the structure in which the dipole part and the asymmetric carbon are directly bonded to a five-membered lactone ring, and a large spontaneous polarization is exhibited (Japanese Journal of Applied Physics, Volume 29, No. 6, pp L 981 to L 983).

SUMMARY OF THE INVENTION

An object of the present invention is to provide a novel optically active compound having a dihydropyran ring which can be advantageously used as a novel type of liquid crystal.

As the result of extensive studies undertaken by the present inventors, it was discovered that a novel compound which has a fluoroalkyl group having a large electron attracting property by itself on the asymmetric carbon atom in a dihydropyran ring exhibits the liquid crystalline property by itself or can be used as an excellent dopant providing a high speed response to a composition comprising it even when the compound does not exhibit the liquid crystal property by itself. The present invention has been completed on the basis of the discovery.

The present invention provides a 2H-5,6-optically active dihydropyran derivative represented by the general formula (I) or (I'):

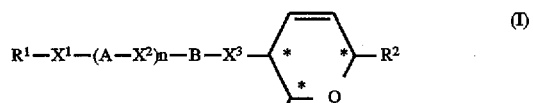

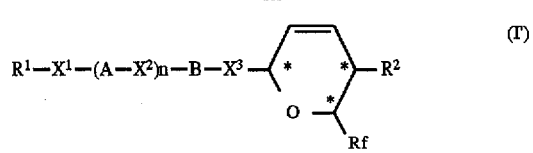

wherein Rf represents a fluoroalkyl group having 1 or 2 carbon atoms, $R^1$ represents a linear or branched alkyl group having 1 to 20 carbon atoms, $X^1$ represents —COO—, —OCO—, —O—, or a single bond, $R^2$ represents a substituent group represented by the general formula (II):

wherein $X^4$ represents —O— or —OCO—, and $R^3$ represents hydrogen, a linear or branched alkyl group having 1 to 15 carbon atoms, an alkenyl group having 2 to 15 carbon atoms, or an aralkyl group having 7 to 10 carbon atoms, or the general formula (III):

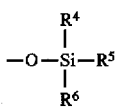

wherein $R^4$, $R^5$, and $R^6$ represent each independently hydrogen, a linear or branched alkyl group having 1 to 15 carbon atoms, an alkenyl group having 2 to 15 carbon atoms, an aryl group having 6 to 10 carbon atoms, or an aralkyl group having 7 to 10 carbon atoms, and Si represents silicon, $X^2$ represents —COO—, —OCO—, —$CH_2O$—, —$OCH_2$—, —C≡C—, or a single bond, $X^3$ represents —COO—, —$CH_2O$—, or —O—, * represents asymmetry of a carbon, A and B represent each independently a substituted or unsubstituted group containing a six-membered ring, and n represents 0 or 1.

The present invention also provides a liquid crystal composition comprising the optically active dihydropyran derivative, a liquid crystal device comprising the liquid crystal composition, and a racemic mixture comprising the optically active dihydropyran derivative.

DETAILED DESCRIPTION OF THE INVENTION

The optically active dihydropyran derivative of the present invention is represented by the general formula (I) or (I'). In the formulae, Rf represents a fluoroalkyl group having 1 or 2 carbon atoms, more specifically trifluoromethyl group, difluoromethyl group, chlorodifluoromethyl group, or pentafluoroethyl group, and preferably trifluoromethyl group.

$R^1$ represents a linear or branched alkyl group having 1 to 20 carbon atoms, such as methyl group, ethyl group, n-propyl group, isopropyl group, n-butyl group, isobutyl group, sec-butyl group, tert-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-eicosyl group. Among these groups, branched alkyl groups having an asymmetric carbon atom are optically active groups.

$R^3$ represents hydrogen, a linear or branched alkyl group having 1 to 15 carbon atoms, an alkenyl group having 2 to 15 carbon atoms, or an aralkyl group having 7 to 10 carbon atoms. Examples of the linear or branched alkyl group having 1 to 15 atoms include methyl group, ethyl group, propyl group, isopropyl group, n-butyl group, sec-butyl group, tert-butyl group, n-pentyl group, isopentyl group, 1-methylbutyl group, n-hexyl group, n-heptyl group, 1-methylheptyl group, n-octyl group, 1-ethylheptyl group, 1-methyloctyl group, n-nonyl group, 1-ethyloctyl group, 1-methylnonyl group, n-decyl group, n-undecyl group, n-dodecyl group, n-tridecyl group, n-tetradecyl group, and n-pentadecyl group. Examples of the alkenyl group having 2 to 15 carbon atoms include vinyl group, allyl group, 1-propenyl group, isopropenyl group, 1-butenyl group, 2-butenyl group, 2-methylallyl group, 1-pentenyl group, 1-hexenyl group, 1-heptenyl group, 1-octenyl group, 2-octenyl group, 1-nonenyl group, 2-nonenyl group, 1-decenyl group, 2-decenyl group, 1-undecenyl group, 2-undecenyl group, 1-dodecenyl group, 2-dodecenyl group, 1-tridecenyl group, 2-tridecenyl group, 1-tetradecenyl group, 2-tetradecenyl group, 1-pentadecenyl group, and 2-pentadecenyl group. Examples of the aralkyl group having 7 to 10 carbon atoms include benzyl group, phenetyl group, phenylpropyl group, and phenylbutyl group.

$R^4$, $R^5$, and $R^6$ represent each independently hydrogen, a linear or branched alkyl group having 1 to 15 carbon atoms, an alkenyl group having 2 to 15 carbon atoms, an aryl group having 6 to 10 carbon atoms, or an aralkyl group having 7 to 10 carbon atoms. Examples of the linear or branched alkyl group having 1 to 15 carbon atoms include methyl group, ethyl group, n-propyl group, isopropyl group, n-butyl group, sec-butyl group, tert-butyl group, n-pentyl group, isopentyl group, 1-methylbutyl group, n-hexyl group, n-heptyl group, 1-methylheptyl group, n-octyl group, 1-ethylheptyl group, 1-methyloctyl group, n-nonyl group, 1-ethyloctyl group, 1-methylnonyl group, n-decyl group, n-undecyl group, n-dodecyl group, n-tridecyl group, n-tetradecyl group, and n-pentadecyl group. Examples of the alkenyl group having 2 to 15 carbon atoms include vinyl group, allyl group, 1-propenyl group, isopropenyl group, 1-butenyl group, 2-butenyl group, 2-methylallyl group, 1-pentenyl group, 1-hexenyl group, 1-heptenyl group, 1-octenyl group, 2-octenyl group, 1-nonenyl group, 2-nonenyl group, 1-decenyl group, 2-decenyl group, 1-undecenyl group, 2-undecenyl group, 1-dodecenyl group, 2-dodecenyl group, 1-tridecenyl group, 2-tridecenyl group, 1-tetradecenyl group, 2-tetradecenyl group, 1-pentadecenyl group, and 2-pentadecenyl group. Examples of the aryl group having 6 to 10 carbon atoms include phenyl group, toluyl group, p-fluorophenyl group, m-fluorophenyl group, o-fluorophenyl group, p-chlorophenyl group, m-chlorophenyl group, o-chlorophenyl group, p-trifluoromethylphenyl group, and p-tert-butylphenyl group. Examples of the aralkyl group having 7 to 10 carbon atoms include benzyl group, phenetyl group, phenylpropyl group, and phenylbutyl group.

Among these groups, $R^4$, $R^5$, and $R^6$ are each preferably a linear or branched alkyl group having 1 to 10 carbon atoms, more preferably a linear or branched alkyl group having 1 to 6 carbon atoms.

The compound represented by the general formula (I) or (I') of the present invention can be prepared in accordance with various processes. Examples of such processes for the preparation of the compound represented by the general formula (I) include the following processes.

(1) The case of $X^2$=a single bond, $X^3$=—COO—, $R^2$=a group represented by the general formula (II), and n=1:

A compound represented by the following general formula (IV):

[wherein $R^1$, $X^1$, A, and B are the same as those described above, and Hal represents a halogen, such as chlorine, bromine, or iodine] and a compound represented by the following general formula (V):

[wherein Rf, $R^2$ and * are the same as those described above] are brought into reaction with each other to obtain the compound represented by the general formula (I). This reaction can be conducted in the presence of an organic base such as pyridine or triethylamine in a solvent such as toluene, benzene, or methylene chloride at a temperature of −20° to 80° C.

(2) The case of $X^2$=a single bond, $X^3$=—CH$_2$O—, $R^2$=a group represented by the general formula (II), and n=1:

A compound represented by the following general formula (VI):

[wherein $R^1$, $X^1$, A, and B are the same as those described above, and Z represents chlorine, bromine, iodine, or tosyl group] and the compound represented by the general formula (V) are brought into reaction with each other to obtain the compound represented by the general formula (I). This reaction can be conducted by treatment of the compound represented by the general formula (V) with a base such as an alkali metal hydride, sodium hydroxide, or potassium hydroxide, followed by addition of the compound represented by the general formula (VI) to the treated compound.

(3) The case of $X^2$=—COO—, $X^3$=—COO—, $R^2$=a group represented by the general formula (II), and n=1:

A compound represented by the following general formula (VII):

[wherein B and Hal are the same as those described above, and Bz represents benzyl group] and the compound represented by the general formula (V) are brought into reaction with each other to obtain a compound represented by the following general formula (VIII):

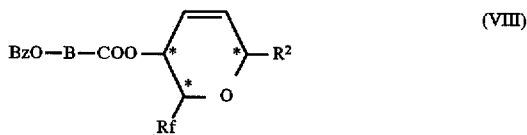

[wherein Rf, Bz, B, $R^2$, and * are the same as those described above]. This reaction can be conducted in the presence of an organic base such as pyridine or triethylamine in a solvent such as toluene, benzene, or methylene chloride at a temperature of −20° to 80° C.

The benzyl group in the resultant compound represented by the general formula (VIII) is eliminated in accordance with a conventional method to form a compound represented by the following general formula (IX):

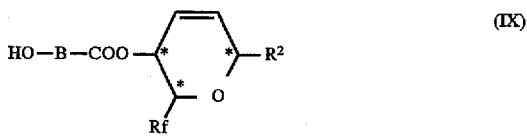

[wherein Rf, B, $R^2$, and * are the same as those described above]. The reaction of elimination of the benzyl group can be conducted by decomposition with hydrogenation under an ordinary pressure in the presence of a catalyst such as a Pd/C catalyst in an alcoholic solvent such as methanol, ethanol, or propanol or in acetic acid.

The resultant compound represented by the general formula (IX) is brought into reaction with a compound represented by the following general formula (X):

[wherein $R^1$, $X^1$, A, and Hal are the same as those described above] to obtain the compound represented by the general formula (I). This reaction can be conducted in the presence of an organic base such as pyridine or triethylamine in a solvent such as toluene, benzene, or methylene chloride at a temperature of −20° to 80° C.

(4) The case of $X^2$=—COO—, $X^3$=—CH$_2$O—, $R^2$=a group represented by the general formula (II), and n=1:

A compound represented by the following general formula (XI):

[wherein Thp represents tetrahydropyranyl group, and B and Z are the same as those described above] and the compound represented by the general formula (V) are brought into reaction with each other to obtain a compound represented by the following general formula (XII):

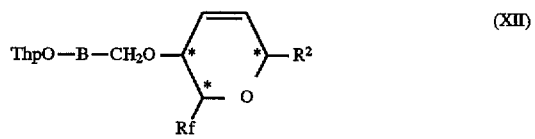

[wherein Rf, Thp, B, $R^2$, and * are the same as those described above]. This reaction can be conducted by treatment of the compound represented by the general formula (V) with a base such as an alkali metal hydride, sodium hydroxide, or potassium hydroxide, followed by addition of the compound represented by the general formula (XI) to the treated compound.

The tetrahydropyranyl group in the resultant compound represented by the general formula (XII) is eliminated in accordance with a conventional method to form a compound represented by the following general formula (XIII):

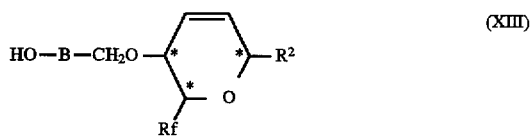

[wherein Rf, B, $R^2$, and * are the same as those described above]. The reaction of elimination of the tetrahydropyranyl group can be conducted in the presence of an acid catalyst such as hydrochloric acid, sulfuric acid, or para-toluenesulfonic acid in a solvent such as diethyl ether, tetrahydrofuran, or chloroform.

The resultant compound represented by the general formula (XIII) is brought into reaction with the compound represented by the general formula (X) to obtain the compound represented by the general formula (I). This reaction can be conducted in the presence of an organic base such as pyridine or triethylamine in a solvent such as toluene, benzene, or methylene chloride at a temperature of −20° to 80° C.

(5) The case of $X^2$=—COO—, $X^3$=—O—, $R^2$=a group represented by the general formula (II), and n=1:

A compound represented by the following general formula (XIV):

[wherein Thp, B, and Hal are the same as those described above] and the compound represented by the general formula (V) are brought into reaction with each other to obtain a compound represented by the following general formula (XV):

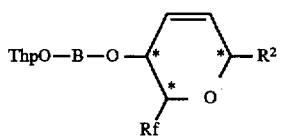

(XV)

[wherein Rf, Thp, B, $R^2$, and * are the same as those described above]. This reaction can be conducted by treatment of the compound represented by the general formula (V) with a base such as an alkali metal hydride, sodium hydroxide, or potassium hydroxide, followed by reaction of the treated compound with the compound represented by the general formula (XIV) under the refluxing condition of dimethylformamide or dimethylsulfoxide in the presence of copper (I) iodide used as the catalyst.

The tetrahydropyran group in the resultant compound represented by the general formula (XV) is eliminated in accordance with a conventional method to obtain a compound represented by the following general formula (XVI):

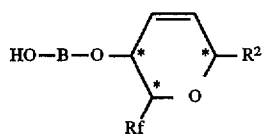

(XVI)

[wherein Rf, B, $R^2$, and * are the same as those described above].

The reaction of elimination of the tetrahydropyran group can be conducted in the presence of an acid catalyst such as hydrochloric acid, sulfuric acid, or para-toluenesulfonic acid in a solvent such as diethyl ether, tetrahydrofuran, or chloroform.

The resultant compound represented by the general formula (XVI) is brought into reaction with the compound represented by the general formula (X) to obtain the compound represented by the general formula (I). This reaction can be conducted in the presence of an organic base such as pyridine or triethylamine in a solvent such as toluene, benzene, or methylene chloride at a temperature of –20° to 80° C.

(6) The case of $X^2$=—$CH_2O$—, $X^3$=—COO—, $R^2$=a group represented by the general formula (II), and n=1:

The compound represented by the general formula (IX) and a compound represented by the following general formula (XVII):

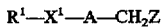

R¹—X¹—A—CH₂Z   (XVII)

[wherein $R^1$, $X^1$, A, and Z are the same as those described above] are brought into reaction with each other to obtain the compound represented by the general formula (I). This reaction can be conducted by treatment of the compound represented by the general formula (IX) with a base such as an alkali metal hydride, sodium hydroxide, or potassium hydroxide, followed by reaction of the compound represented by the general formula (XVII) with the treated compound.

(7) The case of $X^2$=—$OCH_2$—, $X^3$=—COO—, $R^2$=a group represented by the general formula (II), and n=1:

A compound represented by the following general formula (XVIII):

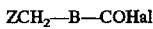

ZCH₂—B—COHal   (XVIII)

[wherein Z, B, and Hal are the same as those described above] and the compound represented by the general formula (V) are brought into reaction with each other to obtain a compound represented by the following general formula (XIX):

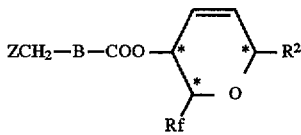

(XIX)

[wherein Rf, Z, B, $R^2$, and * are the same as those described above]. This reaction can be conducted in the presence of an organic base such as pyridine or triethylamine in a solvent such as toluene, benzene, or methylene chloride at a temperature of –20° to 80° C.

The resultant compound represented by the general formula (XIX) is brought into reaction with a compound represented by the following general formula (XX):

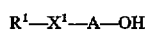

R¹—X¹—A—OH   (XX)

[wherein $R^1$, $X^1$, and A are the same as those described above] to obtain the compound represented by the general formula (I). This reaction can be conducted by treatment of the compound represented by the general formula (XX) with a base such as an alkali metal hydride, sodium hydroxide, or potassium hydroxide, followed by addition of the compound represented by the general formula (XIX) to the treated compound.

(8) The case of $X^3$=—COO—, $R^2$=a group represented by the general formula (III), and n=0:

A compound represented by the following general formula (XXI):

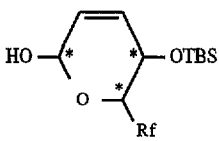

(XXI)

[wherein Rf and * are the same as those described above, and TBS represents tert-butyldimethylsilyl group] and dihydropyran are brought into reaction with each other to obtain a compound represented by the following general formula (XXII):

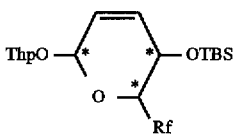

(XXII)

[wherein Rf, TBS, and * are the same as those described above, and Thp represents tetrahydropyranyl group]. This reaction can be conducted in the presence of an acid catalyst such as hydrochloric acid, sulfuric acid, or para-toluenesulfonic acid in a solvent such as diethyl ether, tetrahydrofuran, or chloroform.

The silyl group in the resultant compound having the general formula (XXII) is eliminated to obtain a compound represented by the following general formula (XXIII):

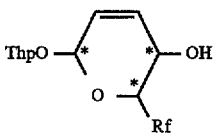

(XXIII)

[wherein Rf, Thp, and * are the same as those described above]. The reaction of elimination of the silyl group can be conducted in accordance with various processes. For example, the reaction can be conducted in a solvent such as tetrahydrofuran in the presence of tetra-n-butyl-ammonium fluoride used as the catalyst at 0° to 50° C.

The resultant compound represented by the general formula (XXIII) is brought into reaction with a compound represented by the following general formula (XXIV):

(XXIV)

[wherein R¹, X¹, B, and Hal are the same as those described above] to obtain a compound represented by the following general formula (XXV)

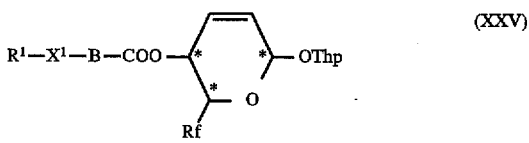
(XXV)

[wherein R¹, X¹, B, Rf, Thp, and * are the same as those described above]. This reaction can be conducted in the presence of an organic base such as pyridine or triethylamine in a solvent such as toluene, benzene, or methylene chloride at a temperature of −20° to 80° C.

The tetrahydropyranyl group in the resultant compound represented by the general formula (XXV) is eliminated in accordance with a conventional method to obtain a compound represented by the following general formula (XXVI):

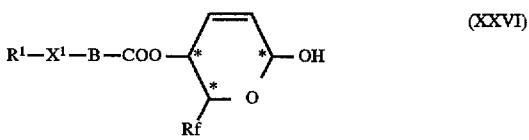
(XXVI)

[wherein R¹, X¹, B, Rf, and * are the same as those described above]. The reaction of elimination of the tetrahydropyranyl group can be conducted in the presence of an acid catalyst such as hydrochloric acid, sulfuric acid, or para-toluenesulfonic acid in a solvent such as diethyl ether, tetrahydrofuran, or chloroform.

The thus obtained compound represented by the general formula (XXVI) is brought into reaction with a compound represented by the following general formula (XXVII):

(XXVII)

[wherein R⁴, R⁵, R⁶, Si, and Hal are the same as those described above] to obtain the object compound represented by the general formula (I). This reaction can be conducted in the presence of an organic base such as imidazole in a solvent such as methylene chloride, diethyl ether, tetrahydrofuran, or toluene at a temperature of −20° to 120° C.

(9) The case of X³=—CH₂O—, R²=a group represented by the general formula (III), and n=0:

The compound represented by the general formula (XXIII) and a compound represented by the following general formula (XXVIII):

(XXVIII)

[wherein R¹, X¹, and B are the same as those described above, and Z represents chlorine, bromine, iodine, or tosyl group] are brought into reaction with each other to obtain a compound represented by the following general formula (XXIX)

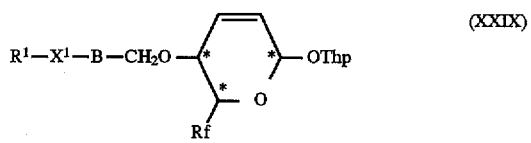
(XXIX)

[wherein R¹, X¹, B, Rf, Thp, and * are the same as those described above]. This reaction can be conducted by treatment of the compound represented by the general formula (XXIII) with a base such as an alkali metal hydride, sodium hydroxide, or potassium hydroxide, followed by addition of the compound represented by the general formula (XXVIII) to the treated compound.

The tetrahydropyranyl group in the resultant compound represented by the general formula (XXIX) is eliminated in accordance with a conventional method to obtain a compound represented by the following general formula (XXX):

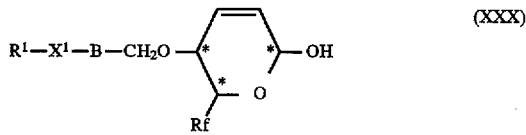
(XXX)

[wherein R¹, X¹, B, Rf, and * are the same as those described above]. The reaction of elimination of the tetrahydropyranyl group can be conducted in the presence of an acid catalyst such as hydrochloric acid, sulfuric acid, or para-toluenesulfonic acid in a solvent such as diethyl ether, tetrahydrofuran, or chloroform.

The resultant compound represented by the general formula (XXX) is brought into reaction with the compound represented by the general formula (XXVII) to obtain the object compound represented by the general formula (I). This reaction can be conducted in the presence of an organic base such as imidazole in a solvent such as methylene chloride, diethyl ether, tetrahydrofuran, or toluene at a temperature of −20° to 120° C.

The compound represented by the general formula (I') of the present invention can be prepared in accordance with various processes. Examples of such processes include the following processes.

(1') The case of X³=—COO—, R²=a group represented by the general formula (II), X⁴=—OCO—, and n=0:

The compound represented by the general formula (XXIV) and the compound represented by the general formula (XXI) are brought into reaction with each other to obtain a compound represented by the following general formula (II'):

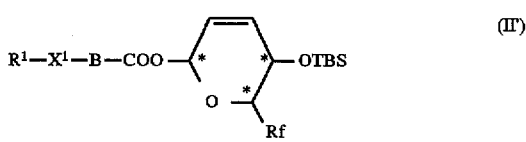
(II')

[wherein R¹, X¹, B, Rf, TBS, and * are the same as those described above]. This reaction can be conducted in the presence of an organic base such as pyridine or triethylamine in a solvent such as toluene, benzene, or methylene chloride at a temperature of −20° to 80° C.

The silyl group in the resultant compound represented by the general formula (II') is eliminated to obtain a compound represented by the following general formula (III'):

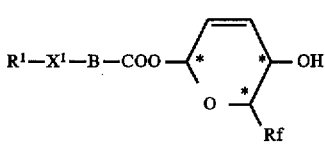
(III')

[wherein R¹, X¹, B, Rf, and * are the same as those described above]. The reaction of elimination of the silyl group can be conducted in accordance with various processes. For example, the reaction can be conducted in tetrahydrofuran as the solvent in the presence of tetra-n-butylammonium fluoride as the catalyst at 0° to 50° C.

The compound represented by the general formula (III') is a mixture of two types of diastereomer. These diastereomers can easily be separated from each other by the silica-gel column chromatography.

The compound represented by the general formula (III') is brought into reaction with a compound represented by the following general formula (IV'):

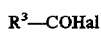
R³—COHal     (IV')

[wherein R³ and Hal are the same as those described above] to obtain the object compound represented by the general formula (I'). This reaction can be conducted in the presence of an organic base such as pyridine or triethylamine in a solvent such as toluene, benzene, or methylene chloride at a temperature of −20° to 80° C.

(2') The case of X³=—COO—, R²=a group represented by the general formula (II), X⁴=—O—, and n=0:

A compound represented by the following general formula (V'):

R⁷—OH     (V')

[wherein R⁷ represents a linear or branched alkyl group having 1 to 15 carbon atoms, an alkenyl group having 2 to 15 carbon atoms, or an aralkyl group having 7 to 10 carbon atoms] and the compound represented by the general formula (XXI) are brought into reach with each other to obtain a compound represented by the following general formula (VI')

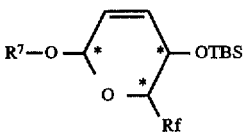
(VI')

[wherein Rf, R⁷, TBS, and * are the same as those described above]. This reaction can be conducted without using any solvent or in a solvent such as tetrahydrofuran in the presence of an acid catalyst such as para-toluenesulfonic acid at 0° to 50° C.

The silyl group in the resultant compound represented by the general formula (VI') is eliminated to obtain a compound represented by the following general formula (VII'):

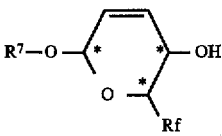
(VII')

[wherein Rf, R⁷, and * are the same as those described above]. The reaction of elimination of the silyl group can be conducted in accordance with various processes. For example, the reaction can be conducted in tetrahydrofuran as the solvent in the presence of tetra-n-butyl-ammonium fluoride as the catalyst at 0° to 50° C.

Then, the resultant compound represented by the general formula (VII') is brought into reaction with a compound represented by the following general formula (VIII'):

R³—Z     (VIII')

[wherein R³ and Z are the same as those described above] to obtain a compound represented by the following general formula (IX'):

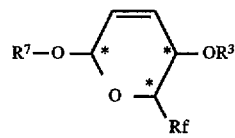
(IX')

[wherein Rf, R³, R⁷, and * are the same as those described above]. This reaction can be conducted by treatment of the compound represented by the general formula (VII') with a base such as an alkali metal hydride, sodium hydroxide, or potassium hydroxide, followed by addition of the compound represented by the general formula (VIII') to the treated compound.

The resultant compound represented by the general formula (IX') is allowed to react in the presence of an acid catalyst to obtain a compound represented by the following general formula (X'):

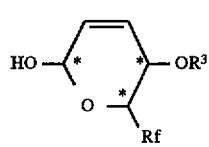
(X')

[wherein Rf, R³, and * are the same as those described above]. This reaction can be conducted in the presence of water in a solvent such as tetrahydrofuran, diethyl ether, or toluene in the presence of an acid catalyst such as para-toluenesulfonic acid, hydrochloric acid, or sulfuric acid at 0° to 100° C.

The compound represented by the general formula (X') is brought into reaction with the compound represented by the general formula (XXI) to obtain the object compound represented by the general formula (I'). This reaction can be conducted in the presence of an organic base such as pyridine or triethylamine in a solvent such as toluene, benzene, or methylene chloride at temperature of −20° to 80° C.

(3') The case of X³=—CH₂O—, R²=a group represented by the general formula (II), X=—OCO—, and n=0:

The compound represented by the general formula (XXVIII) and the compound represented by the general formula (XXI) are brought into reaction with each other to obtain a compound represented by the following general formula (XI'):

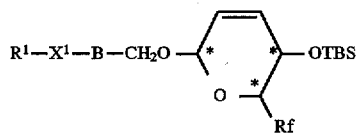
(XI')

[wherein Rf, R¹, X¹, B, TBS, and * are the same as those described above]. This reaction is conducted, for example, in the presence of an acid catalyst such as para-toluenesulfonic acid, sulfuric acid, or trifluoromethanesulfonic acid in a solvent such as tetrahydrofuran, diethyl ether, methylene chloride, or toluene at 0° to 100° C.

Then, the silyl group in the resultant compound represented by the general formula (XI') is eliminated to obtain a compound represented by the following general formula (XII'):

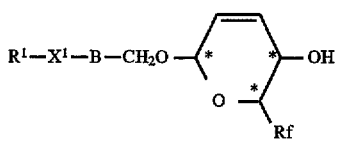

[wherein Rf, $R^1$, $X^1$, B, and * are the same as those described above]. The reaction of elimination of the silyl group can be conduced in accordance with various processes. For example, the reaction can be conducted in tetrahydrofuran as the solvent in the presence of tetra-n-butyl-ammonium fluoride as the catalyst at 0° to 50° C.

The compound represented by the general formula (XII') is a mixture of two types of diastereomer. The diastereomers can easily be separated by the silica-gel column chromatography.

The compound represented by the general formula (XII') is brought into reaction with the compound represented by the general formula (IV') to obtain the object compound represented by the general formula (I'). This reaction can be conducted in the presence of an organic base such as pyridine or triethylamine in a solvent such as toluene, benzene, or methylene chloride at a temperature of −20° to 80° C.

(4') The case of $X^3$=—$CH_2O$—, $R^2$=a group represented by the general formula (II), $X^4$=—O—, and n=0:

The compound represented by the general formula (XII') and the compound represented by the general formula (VIII') are brought into reaction with each other to obtain the object compound represented by the general formula (I'). This reaction can be conducted by treatment of the compound represented by the general formula (XII') with a base such as an alkali metal hydride, sodium hydroxide, or potassium hydroxide, followed by addition of the compound represented by the general formula (VIII') to the treated compound.

(5') The case of $X^2$=—COO—, $X^3$=—COO—, $R^2$=a group represented by the general formula (II), $X^4$=—O—, and n=1:

The compound represented by the general formula (VII) and the compound represented by the general formula (X') are brought into reaction with each other to obtain a compound represented by the following general formula (XIII'):

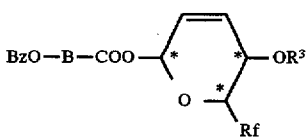

[wherein Rf, $R^3$, B, Bz, and * are the same as those described above]. This reaction can be conducted in the presence of an organic base such as pyridine or triethylamine in a solvent such as toluene, benzene, or methylene chloride at a temperature of −20° to 80° C.

Then, the benzyl group in the resultant compound represented by the general formula (XIII') is eliminated to obtain a compound represented by the following general formula (XIV'):

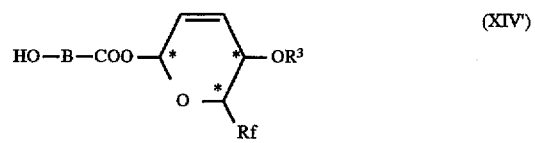

[wherein Rf, $R^3$, B, and * are the same as those described above]. The reaction of elimination of the benzyl group can be conducted in accordance with various processes. For example, the reaction can be conducted by decomposition with hydrogenation under an ordinary pressure in the presence of a palladium-carbon (Pd/C) catalyst in an alcoholic solvent such as methanol, ethanol, or propanol or in acetic acid.

The compound represented by the general formula (XIV') is brought into reaction with the compound represented by the general formula (X) to obtain the object compound represented by the general formula (I'). This reaction can be conducted in the presence of an organic base such as pyridine or triethylamine in a solvent such as toluene, benzene, or methylene chloride at a temperature of −20° to 80° C.

(6') The case of $X^3$=—COO—, $R^2$=a group represented by the general formula (III), and n=0:

The compound represented by the general formula (III') and the compound represented by the general formula (XXVII) are brought into reaction with each other to obtain the object compound represented by the general formula (I'). This reaction can be conducted in the presence of an organic base such as imidazole in a solvent such as methylene chloride, diethyl ether, tetrahydrofuran, or toluene at a temperature of −20° to 120° C.

(7') The case of $X^3$—$CH_2O$—, $R^2$=a group represented by the general formula (III), and n=0:

The compound represented by the general formula (XII') and the compound represented by the general formula (XXVII) are brought into reaction with each other to obtain the object compound represented by the general formula (I'). This reaction can be conducted in the presence of an organic base such as imidazole in a solvent such as methylene chloride, diethyl ether, tetrahydrofuran, or toluene at a temperature of −20° to 120° C.

(8') The case of $X^2$=—COO—, $X^3$=—COO—, $R^2$=a group represented by the general formula (III), and n=1:

The compound represented by the general formula (VII) and the compound represented by the general formula (XXI) are brought into reaction with each other to obtain a compound represented by the following general formula (XV'):

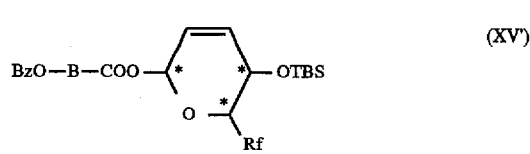

[wherein Rf, B, Bz, TBS, and * are the same as those described above]. This reaction can be conducted in the presence of an organic base such as pyridine or triethylamine in a solvent such as toluene, benzene, or methylene chloride at a temperature of −20° to 80° C.

Then, the silyl group in the resultant compound represented by the general formula (XV') is eliminated to obtain a compound represented by the following general formula (XVI'):

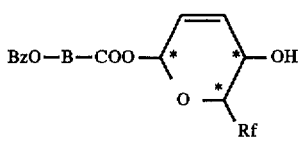
(XVI')

[wherein Rf, B, Bz, and * are the same as those described above]. The reaction of elimination of the silyl group can be conducted in accordance with various processes. For example, the reaction can be conducted in tetrahydrofuran as the solvent in the presence of tetra-n-butyl-ammonium fluoride as the catalyst at 0° to 50° C.

The resultant compound represented by the general formula (XVI') is brought into reaction with the compound represented by the general formula (XXVII) to obtain a compound represented by the following general formula (XVII'):

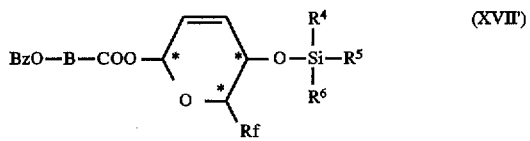
(XVII')

[wherein Rf, $R^4$, $R^5$, $R^6$, B, Bz, Si, and * are the same as those described above]. This reaction can be conducted in the presence of an organic base such as imidazole in a solvent such as methylene chloride, diethyl ether, tetrahydrofuran, or toluene at a temperature of –20° to 120° C.

Then, the benzyl group in the resultant compound represented by the general formula (XVII') is eliminated to obtain a compound represented by the following general formula (XVIII'):

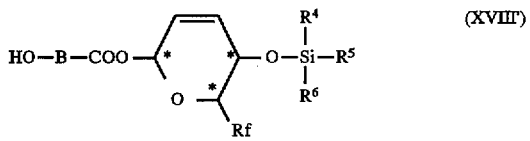
(XVIII')

[wherein Rf, $R^4$, $R^5$, $R^6$, B, Si, and * are the same as those described above]. The reaction of elimination of the benzyl group can be conducted in accordance with various processes. For example, the reaction can be conducted by decomposition with hydrogenation under an ordinary pressure in the presence of a palladium-carbon (Pd/C) catalyst in an alcoholic solvent such as methanol, ethanol, or propanol or in acetic acid.

Then, the resultant compound represented by the general formula (XVIII') is brought into reaction with the compound represented by the general formula (X) to obtain the object compound represented by the general formula (I'). This reaction can be conducted in the presence of an organic base such as pyridine or triethylamine in a solvent such as toluene, benzene, or methylene chloride at a temperature of –20° to 80° C.

(9') The case of $X^2$=a single bond, $X^3$=—COO—, $R^2$=—O—TBS, and n=1:

The compound represented by the general formula (XXI) and the compound represented by the general formula (IV) are brought into reaction with each other to obtain the object compound (I'). This reaction can be conducted in the presence of an organic base such as pyridine or triethylamine in a solvent such as toluene, benzene, or methylene chloride at a temperature of –20° to 80° C.

The compound represented by the general formula (V) used as a starting material for the preparation of the compound represented by the general formula (I) or (I') in which $R^2$ is a group represented by the general formula (III) can be prepared in accordance with various processes. Examples of the compound represented by the general formula (V) include the following compounds:

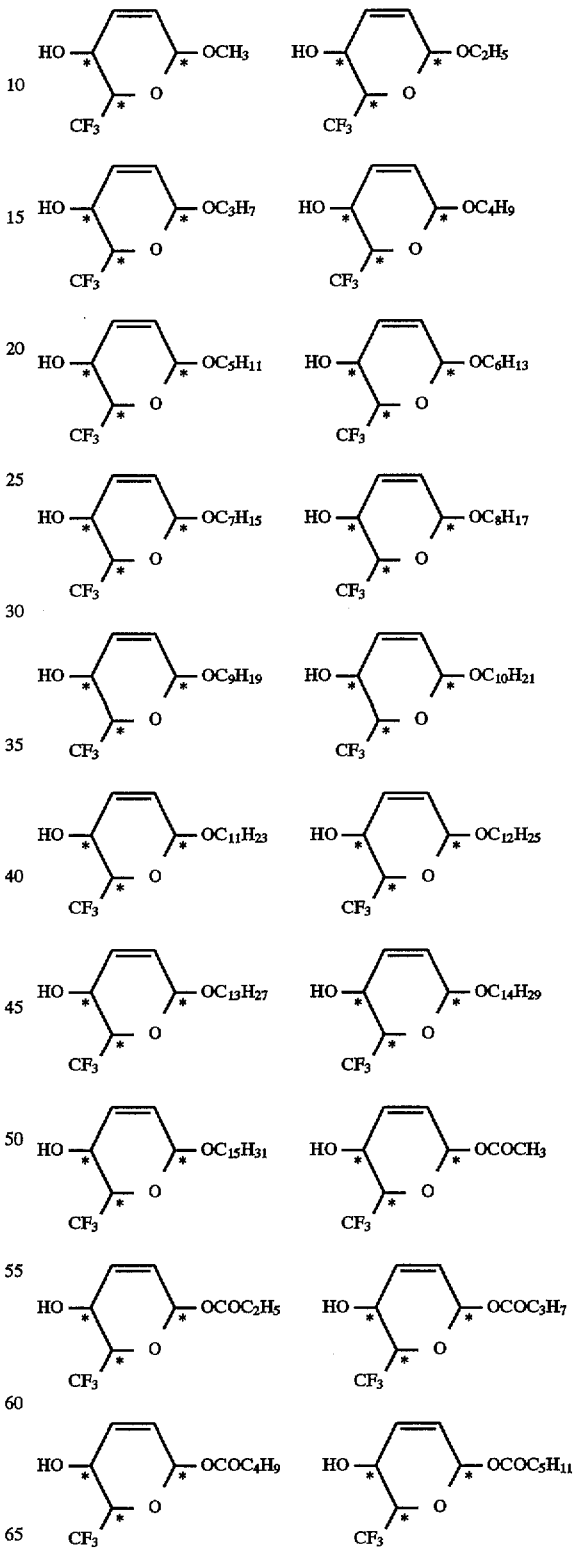

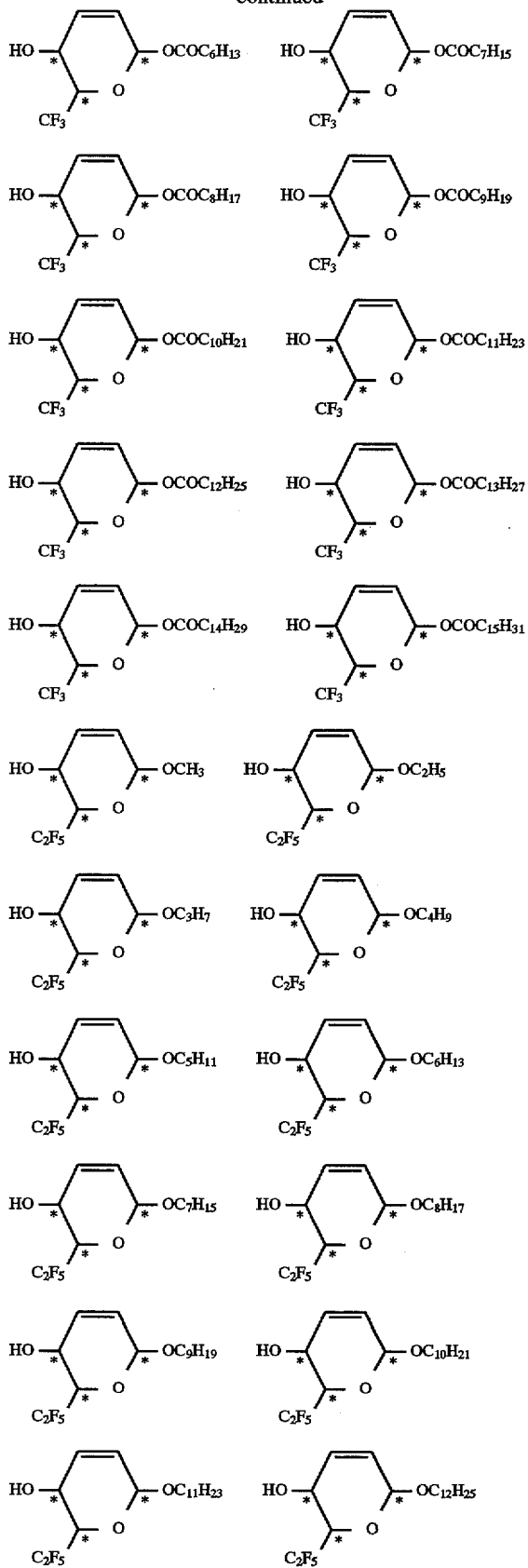
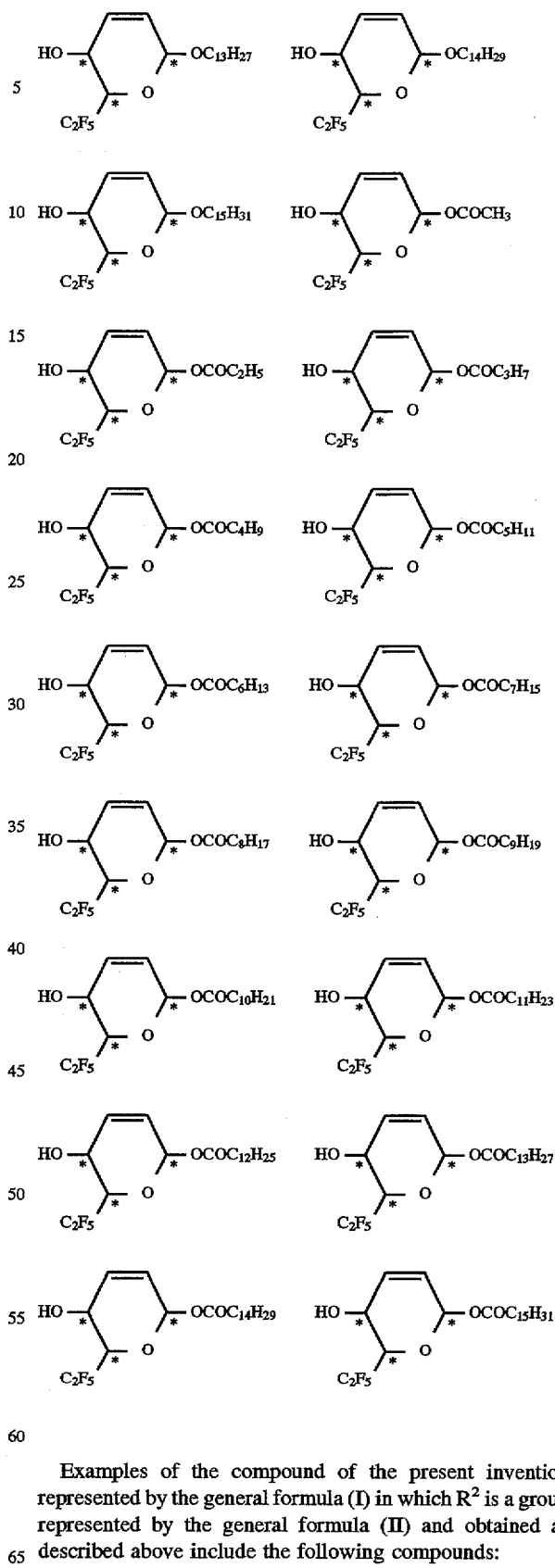
Examples of the compound of the present invention represented by the general formula (I) in which $R^2$ is a group represented by the general formula (II) and obtained as described above include the following compounds:

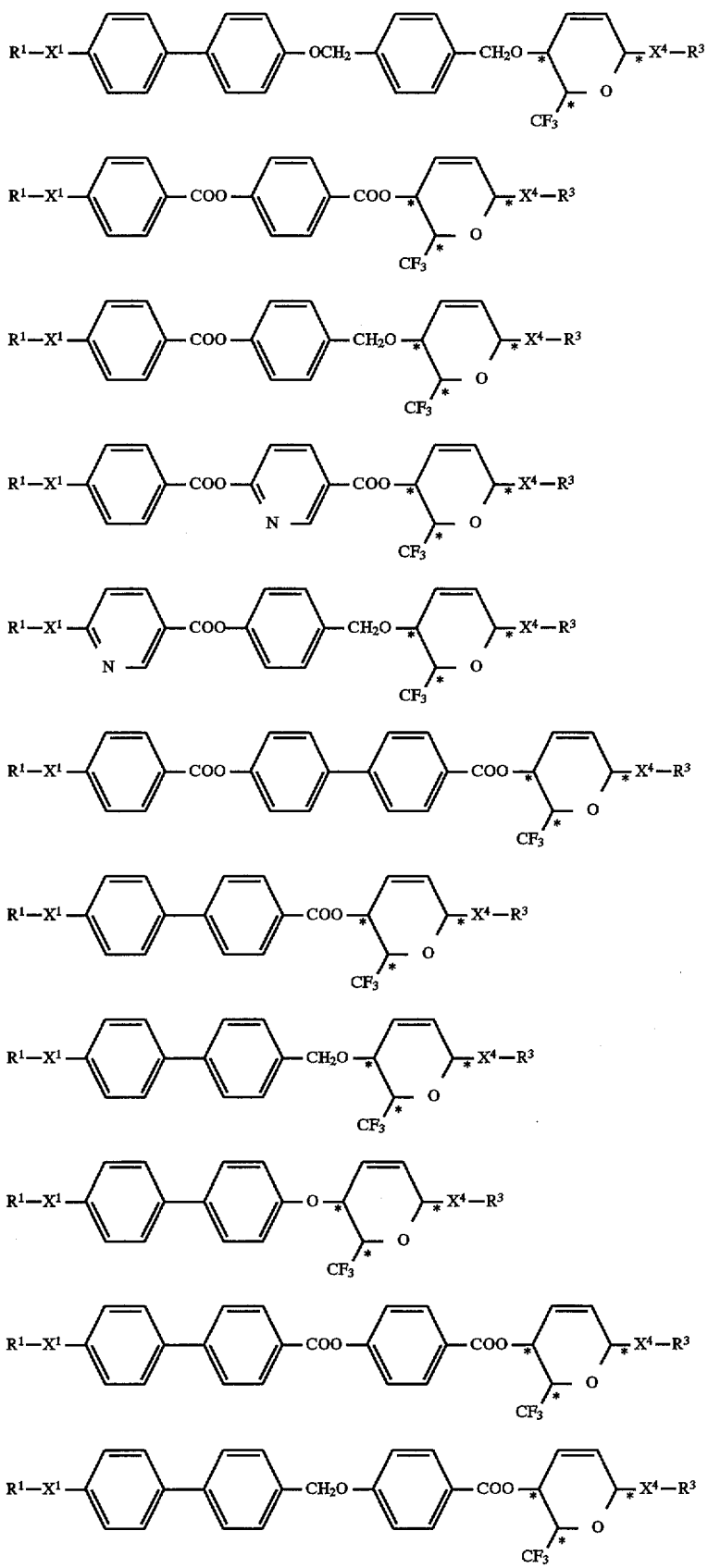

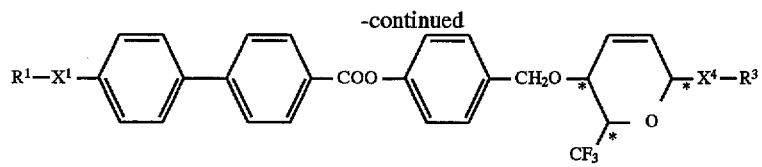
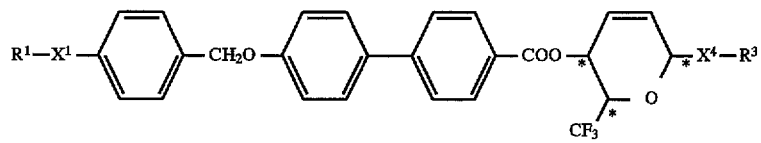
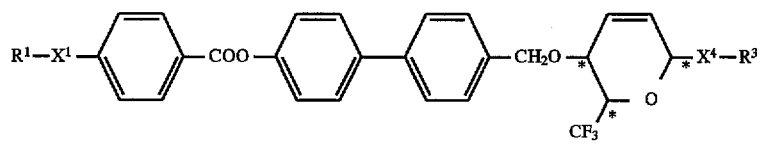
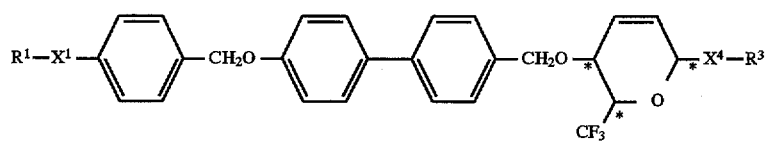
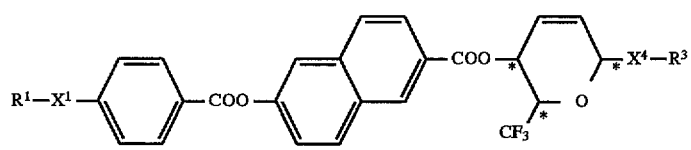
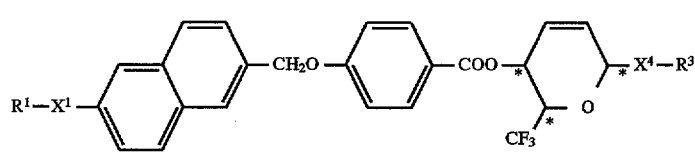
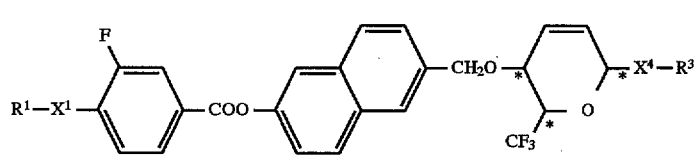
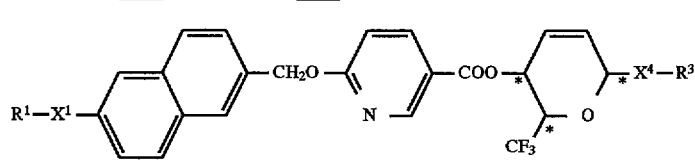
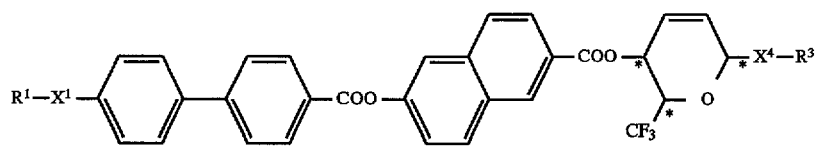
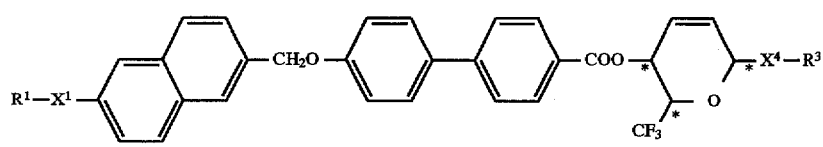
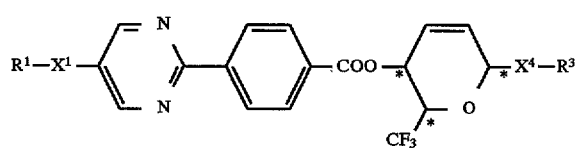

-continued
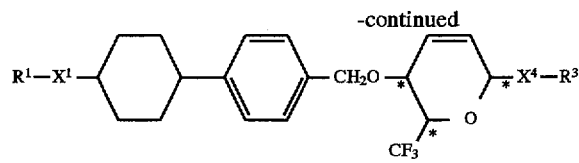
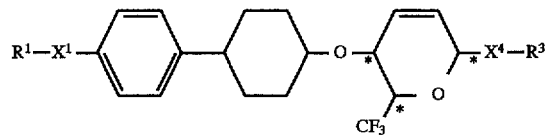
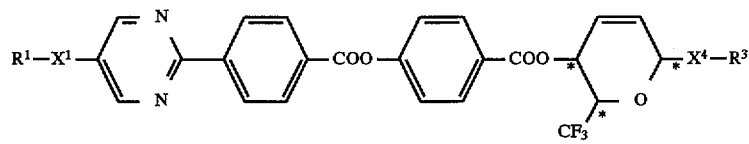
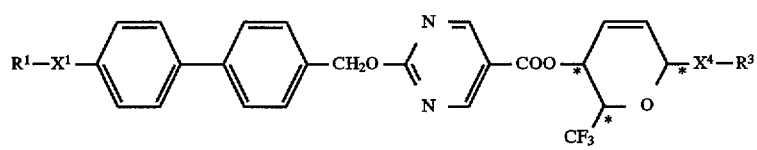
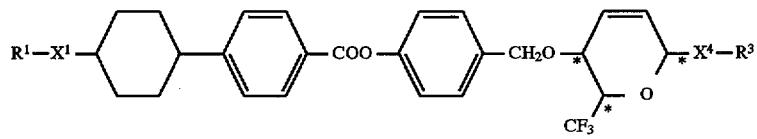
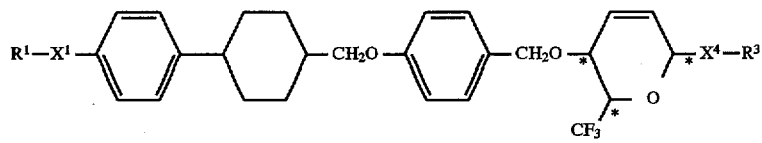
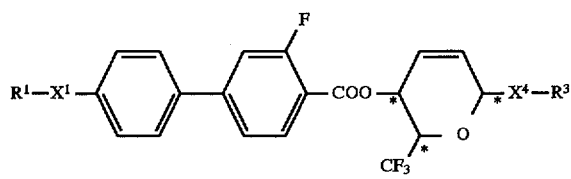
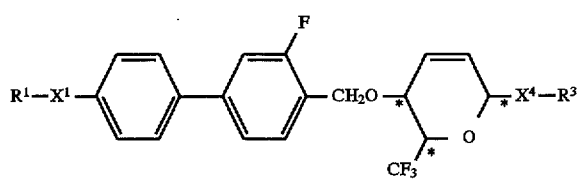
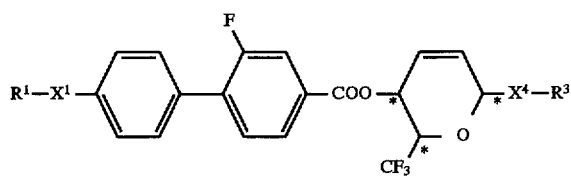
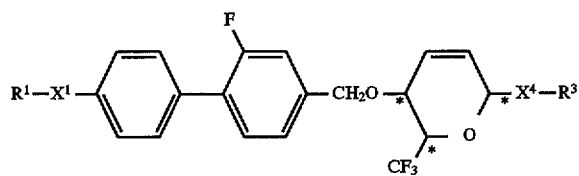

-continued
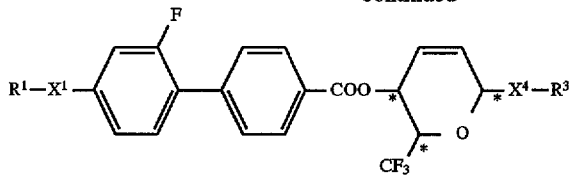
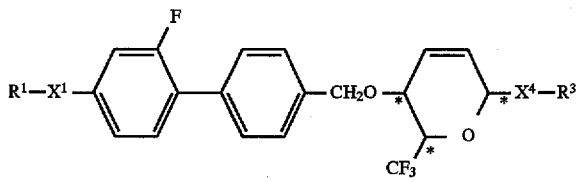
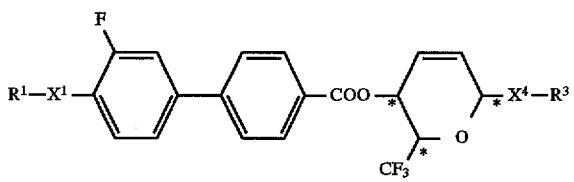
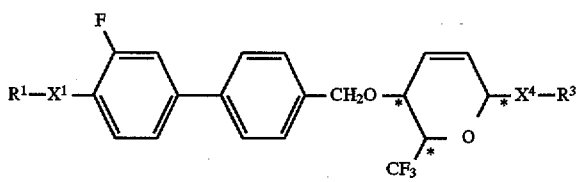
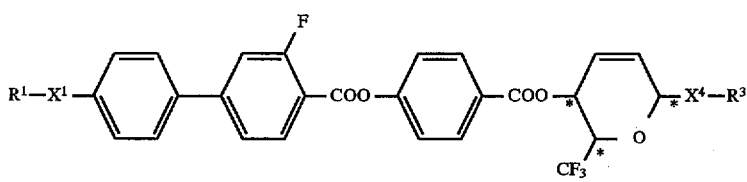
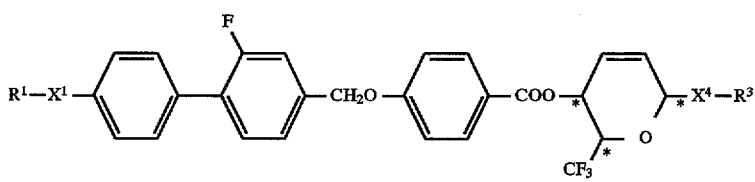
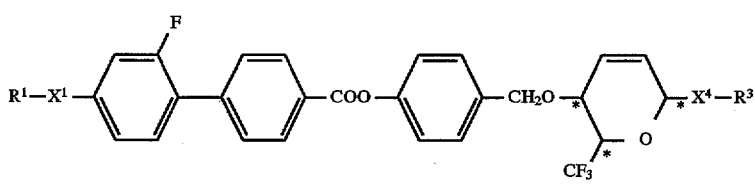
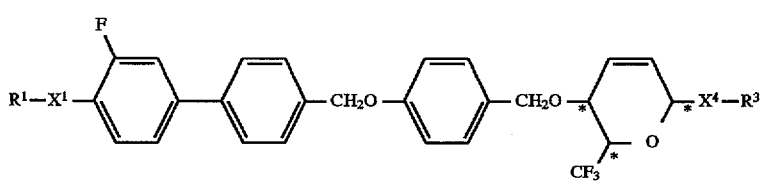
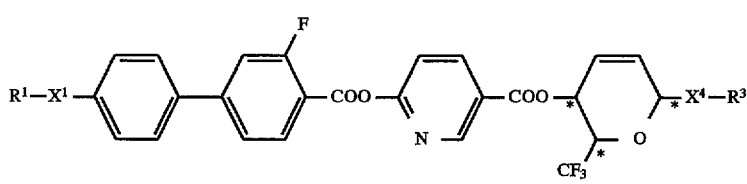

-continued
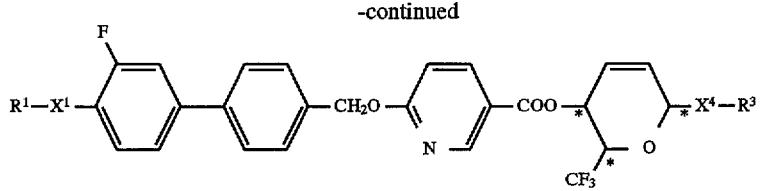
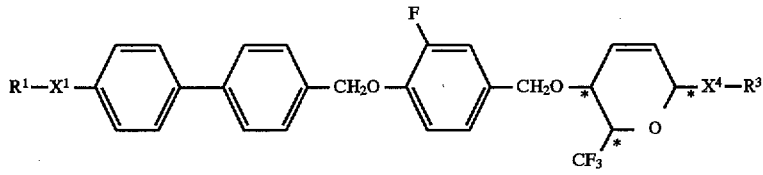
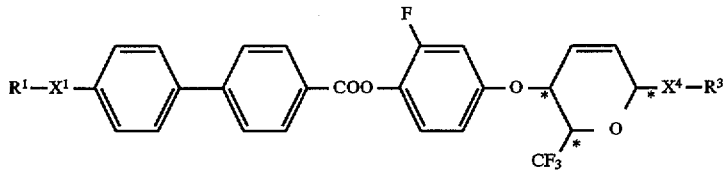
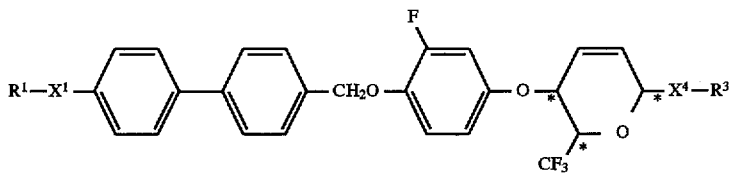
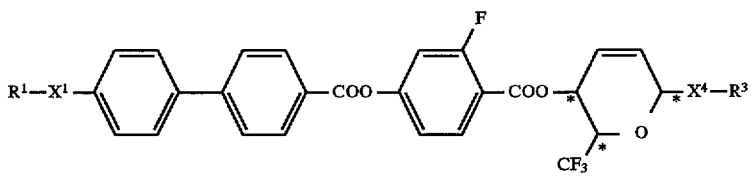
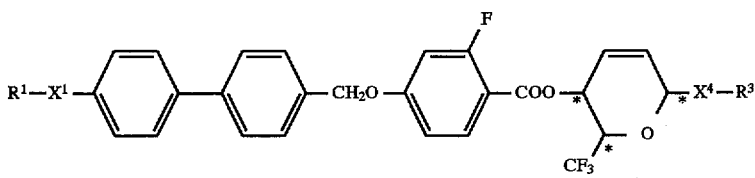
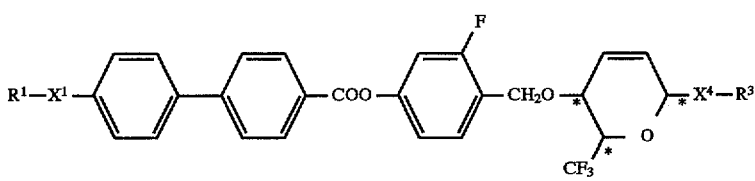
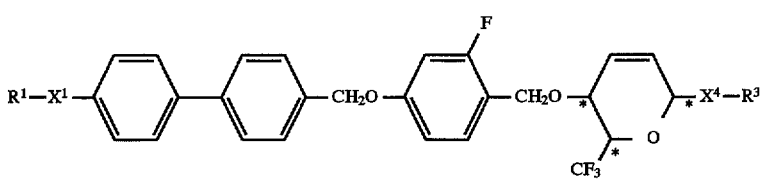
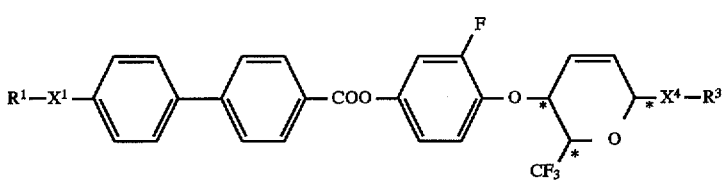

-continued
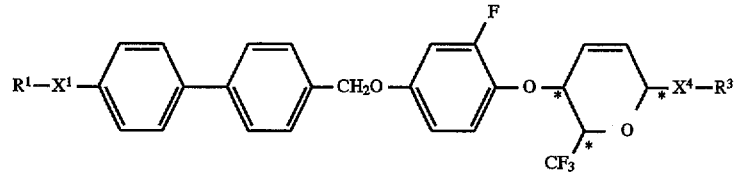
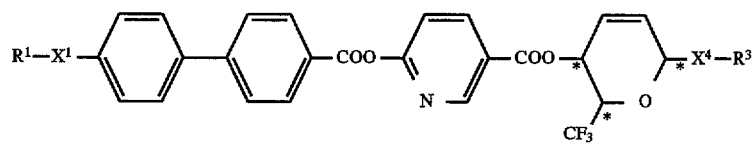
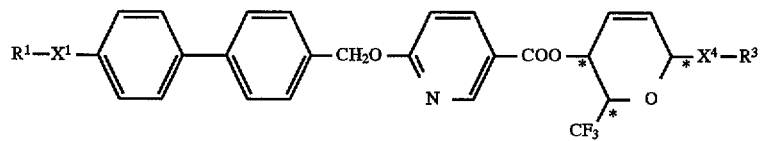
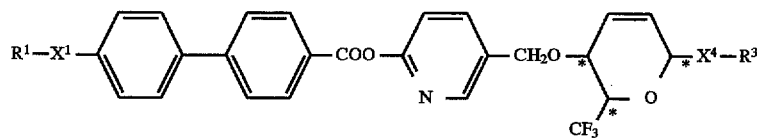
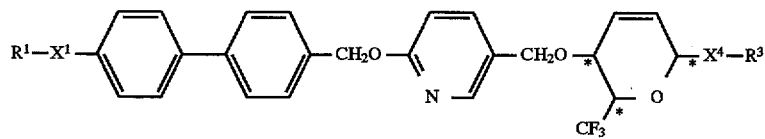
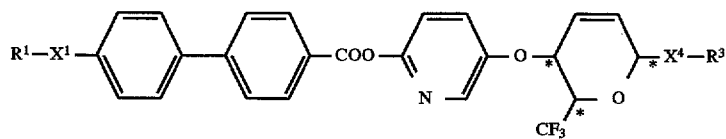
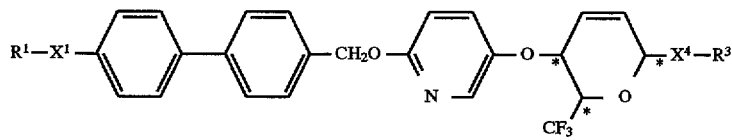
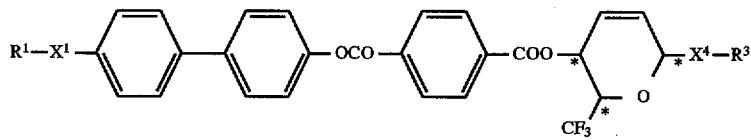
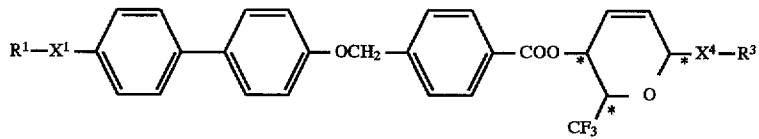
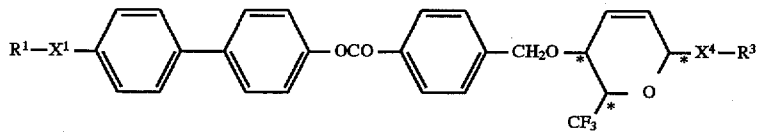
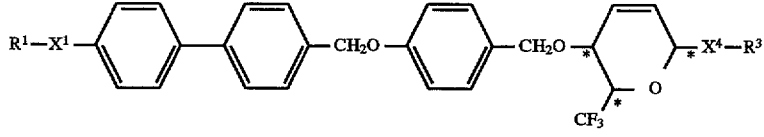

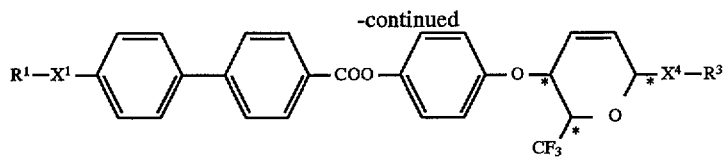
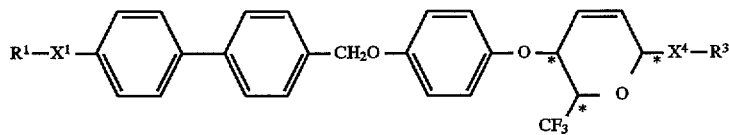
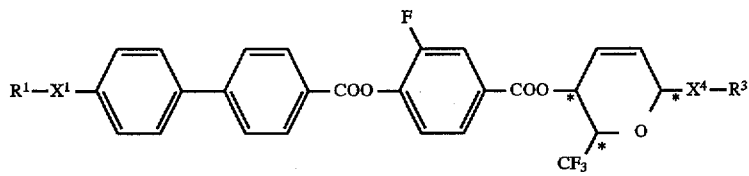
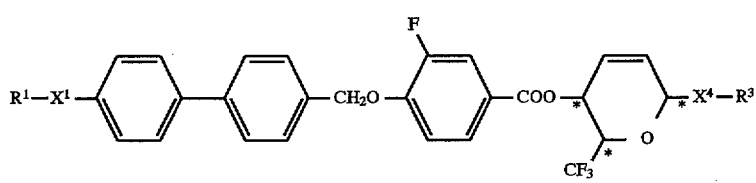
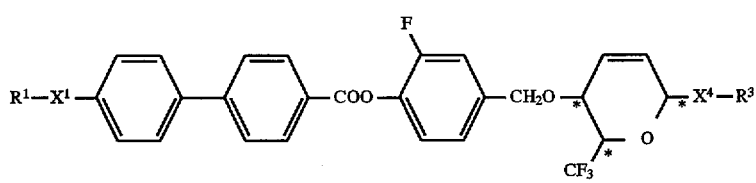
In the above formulae, $R^1$, $R^3$, $X^1$, $X^4$, and * are the same as those described above.
Examples of the compound of the present invention represented by the general formula (I') in which $R^2$ is a group represented by the general formula (II) and obtained as described above include the following compounds:
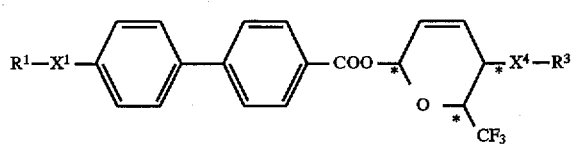
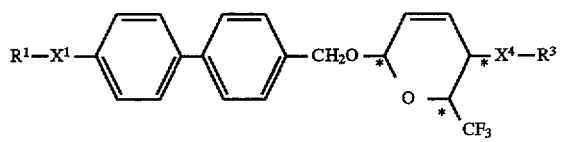
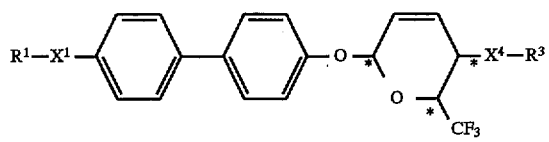
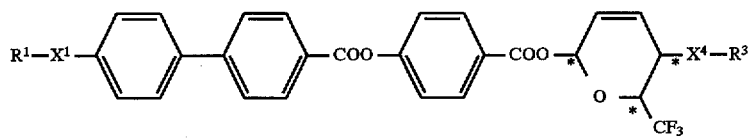

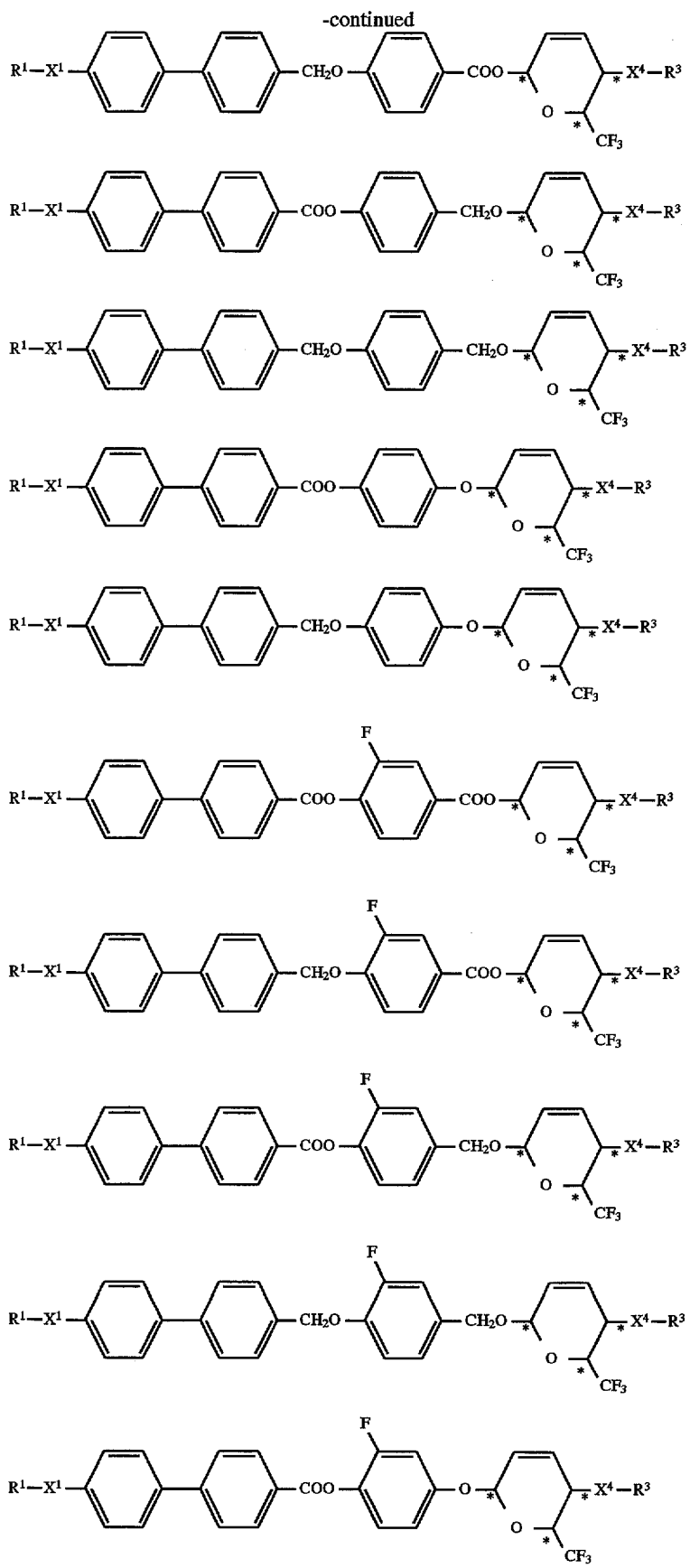

-continued
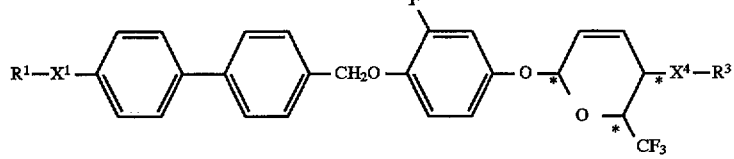
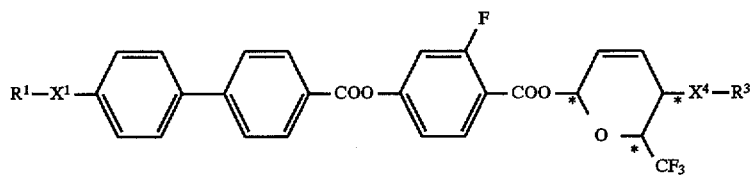
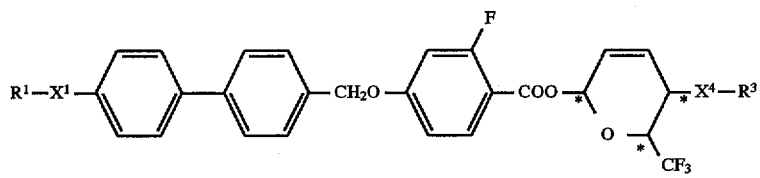
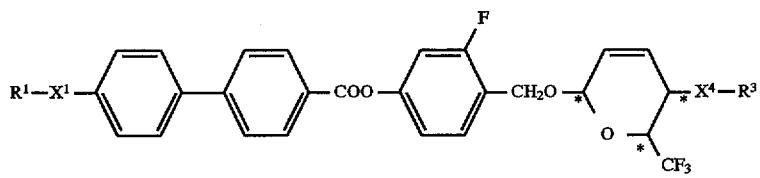
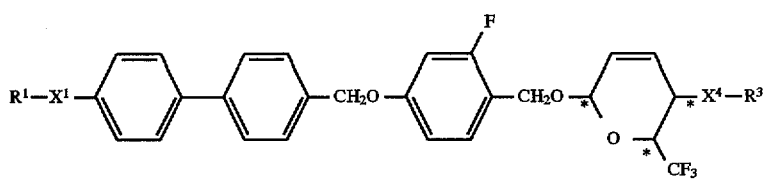
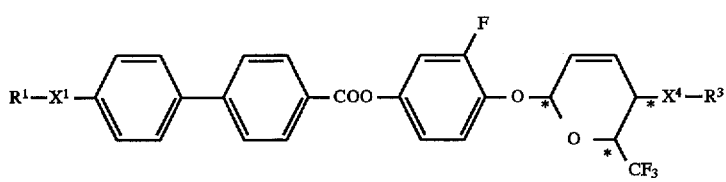
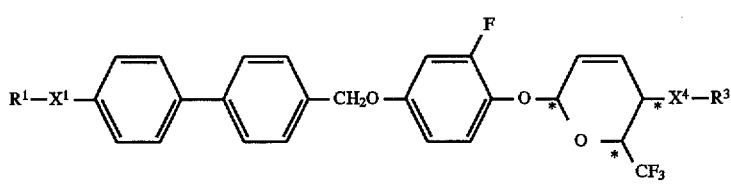
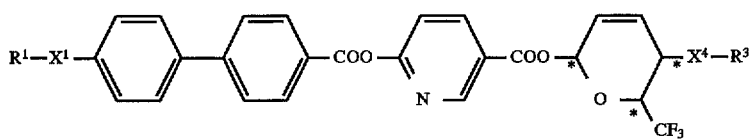
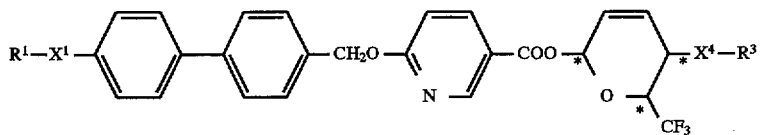

-continued
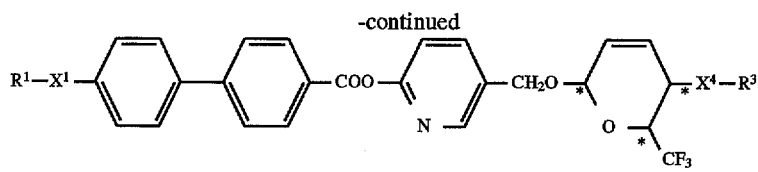
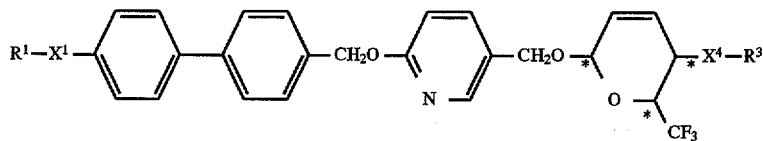
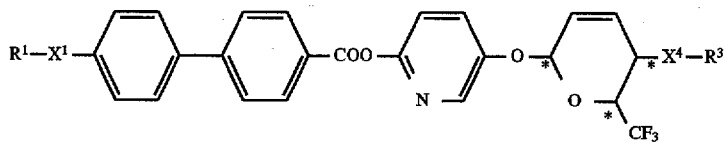
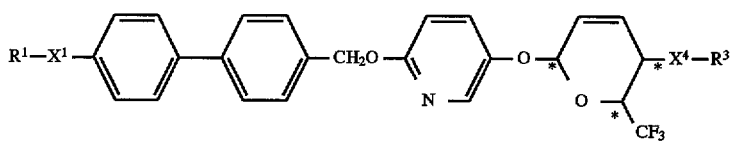
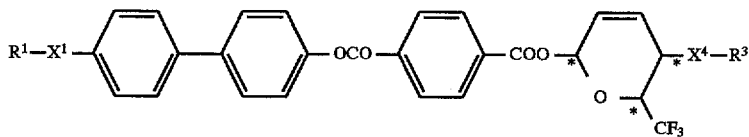
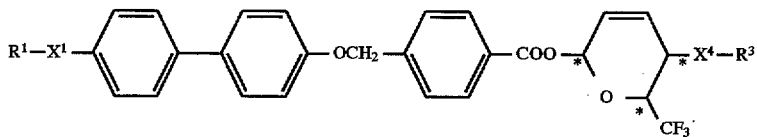
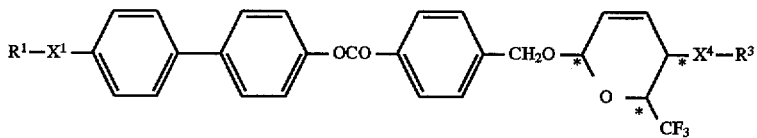
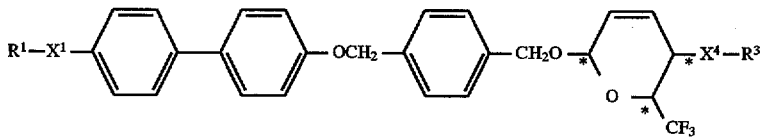
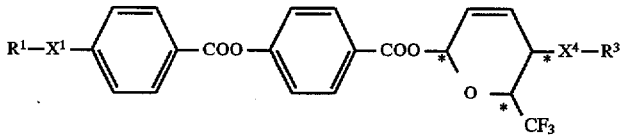
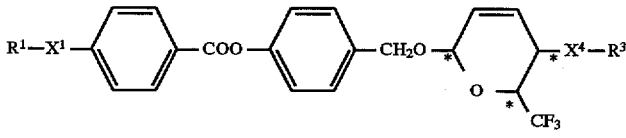
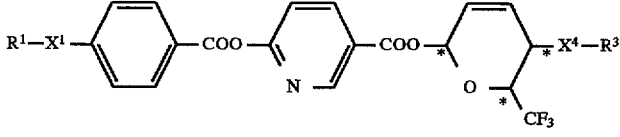

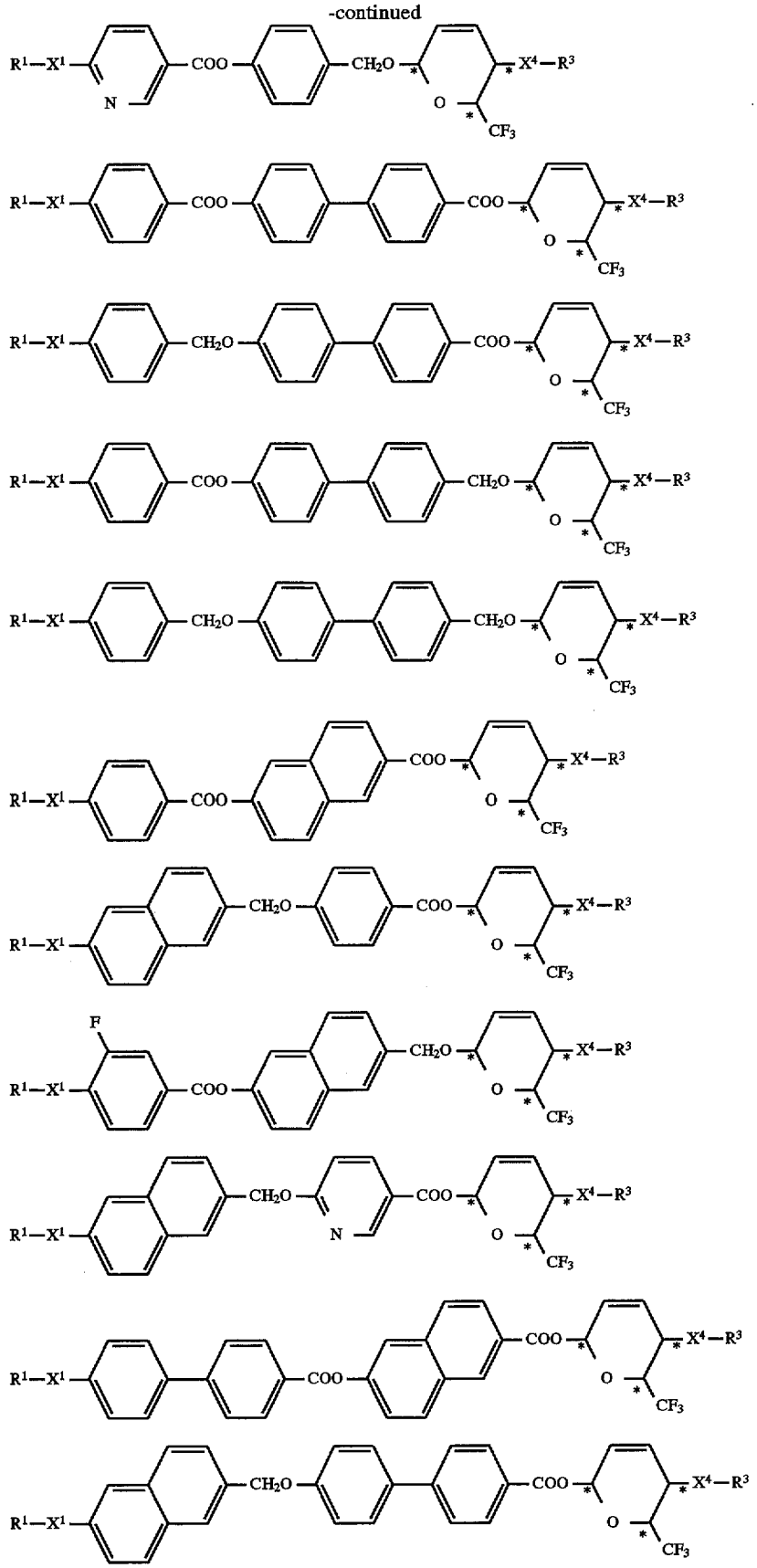

-continued
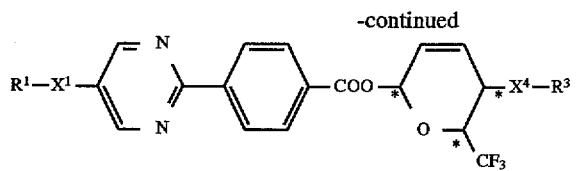
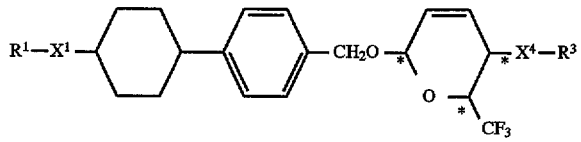
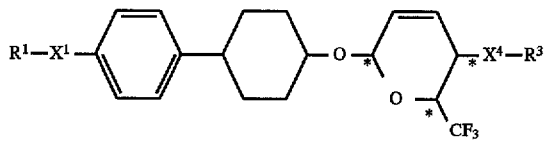
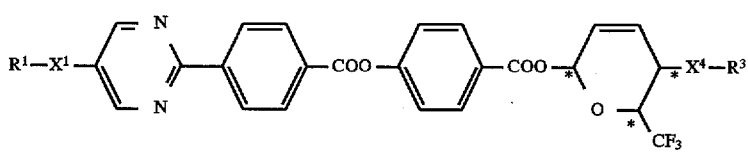
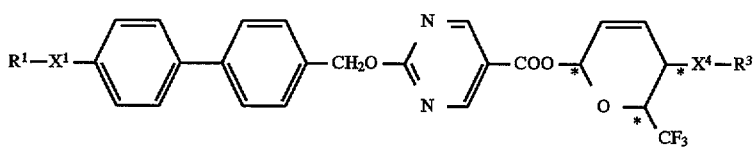
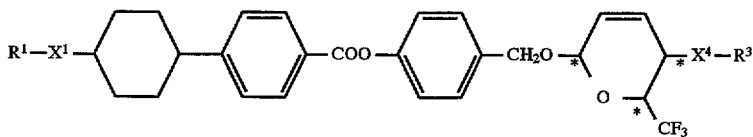
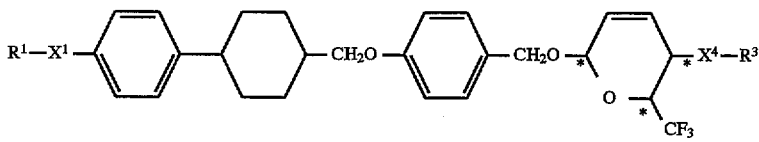
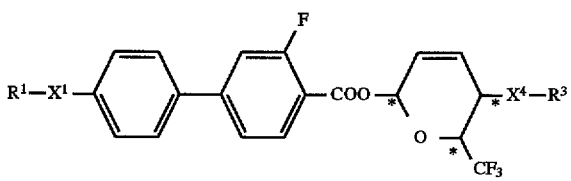
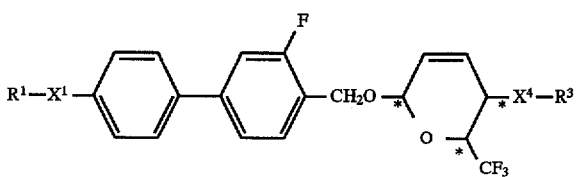
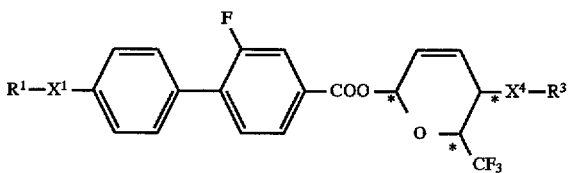

-continued
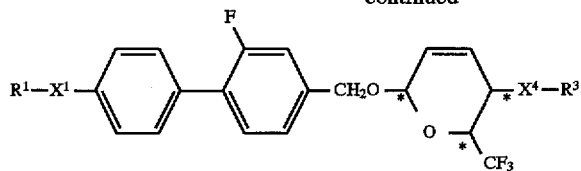
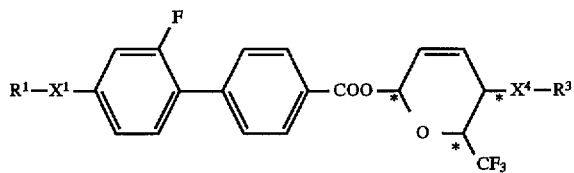
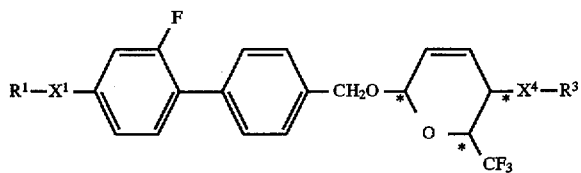
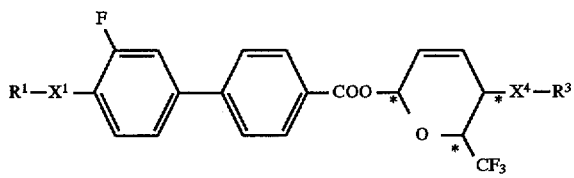
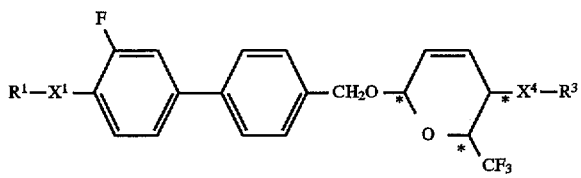
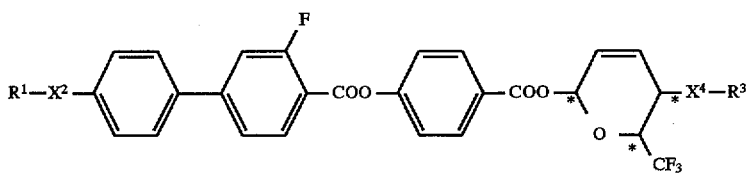
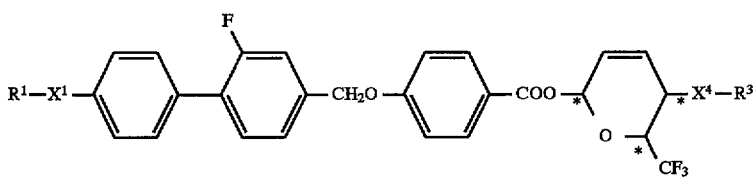
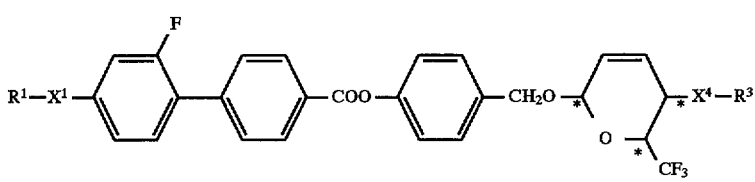
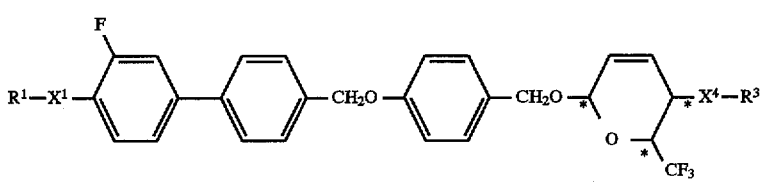

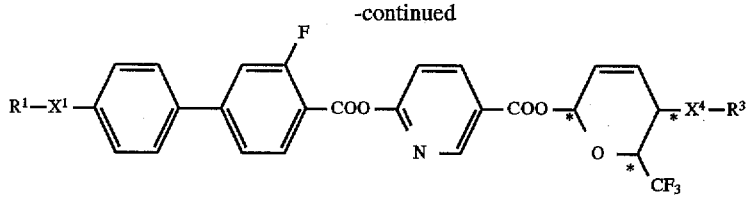

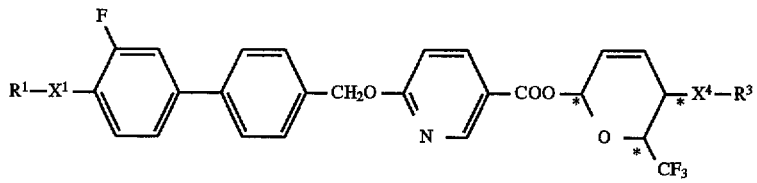

In the above formulae, $R^1$, $R^3$, $X^1$, $X^4$, and * are the same as those described above.

The compound represented by the general formula (XXI) used as a starting material for the preparation of the compound represented by the general formula (I) or (I') in which $R^2$ is a group represented by the general formula (III) can be prepared in accordance with various processes. Examples of the compound represented by the general formula (XXI) include the following compounds:

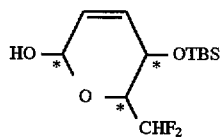

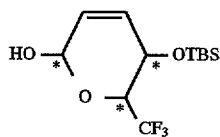

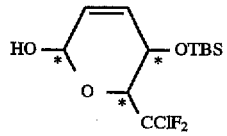

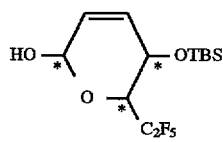

In the above formulae, TBS and * are the same as described above.

Examples of the compound of the present invention represented by the general formula (I) in which $R^2$ is a group represented by the general formula (III) and obtained as described above include the following compounds:

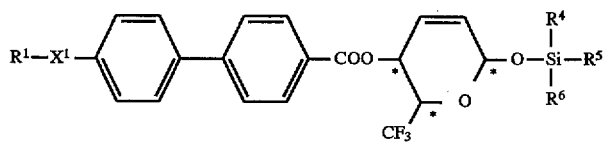

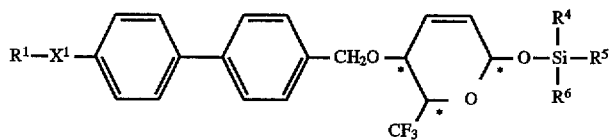

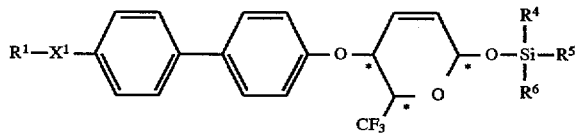

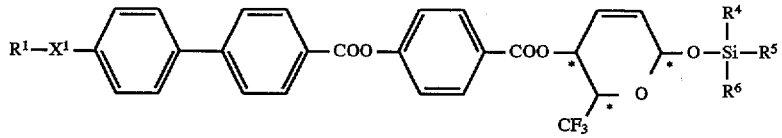

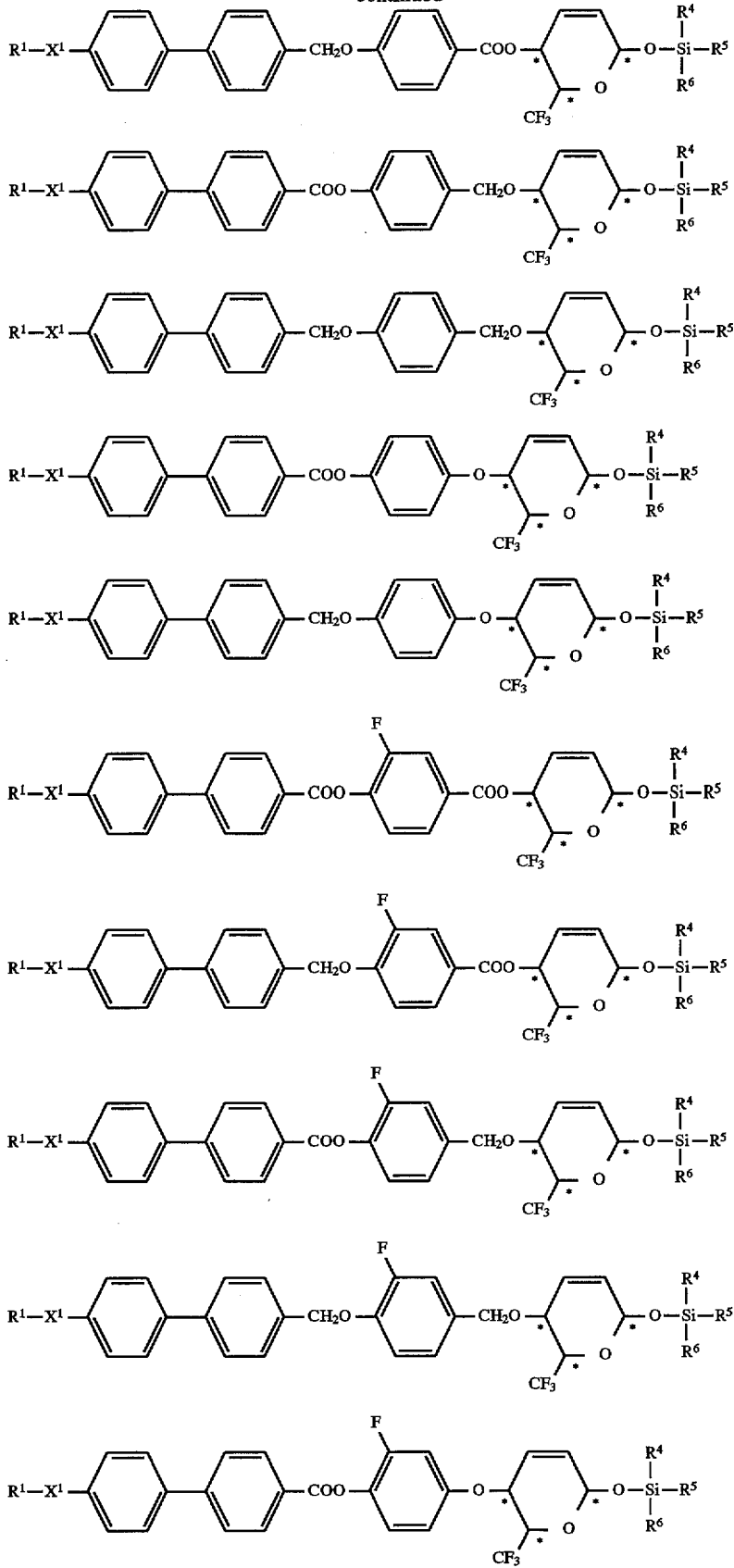

-continued
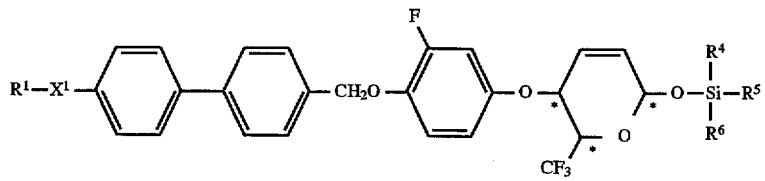
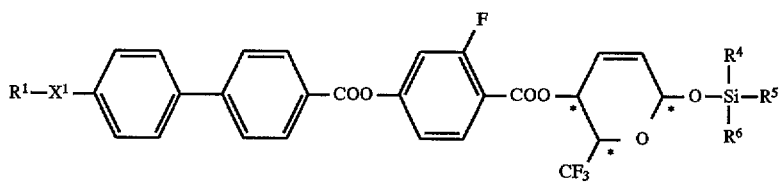
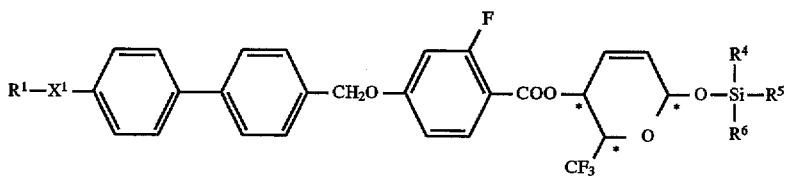
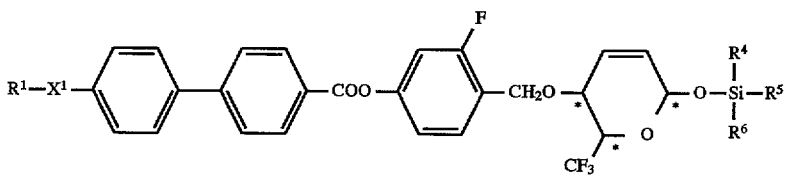
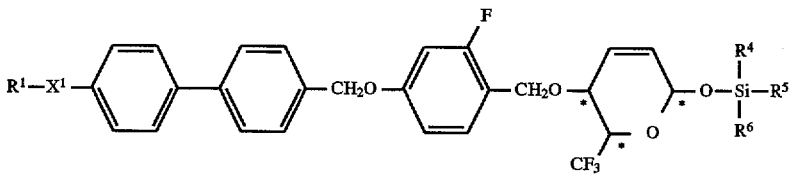
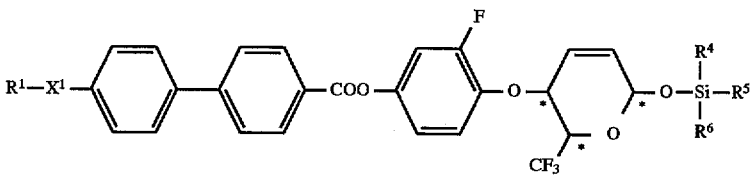
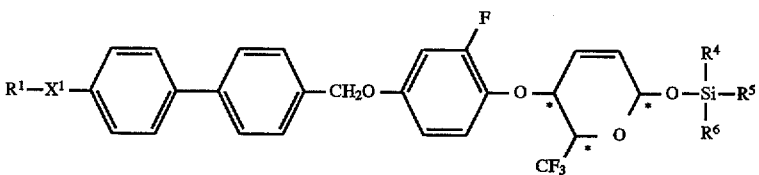
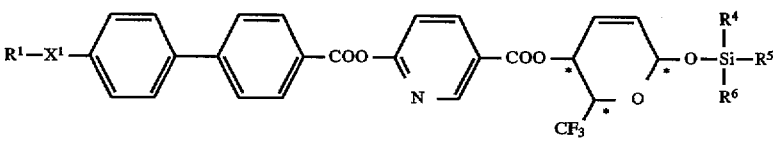
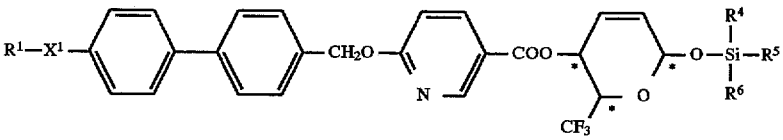

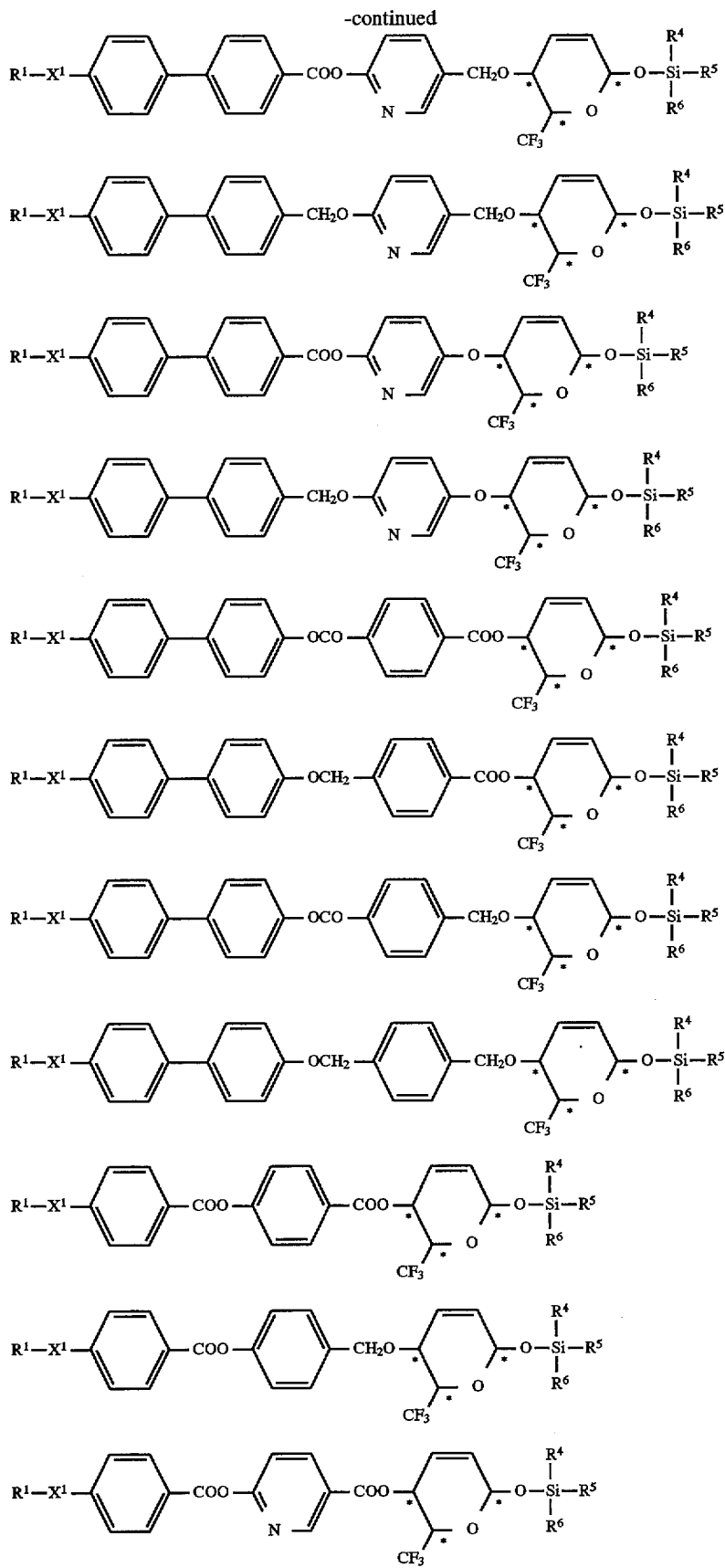

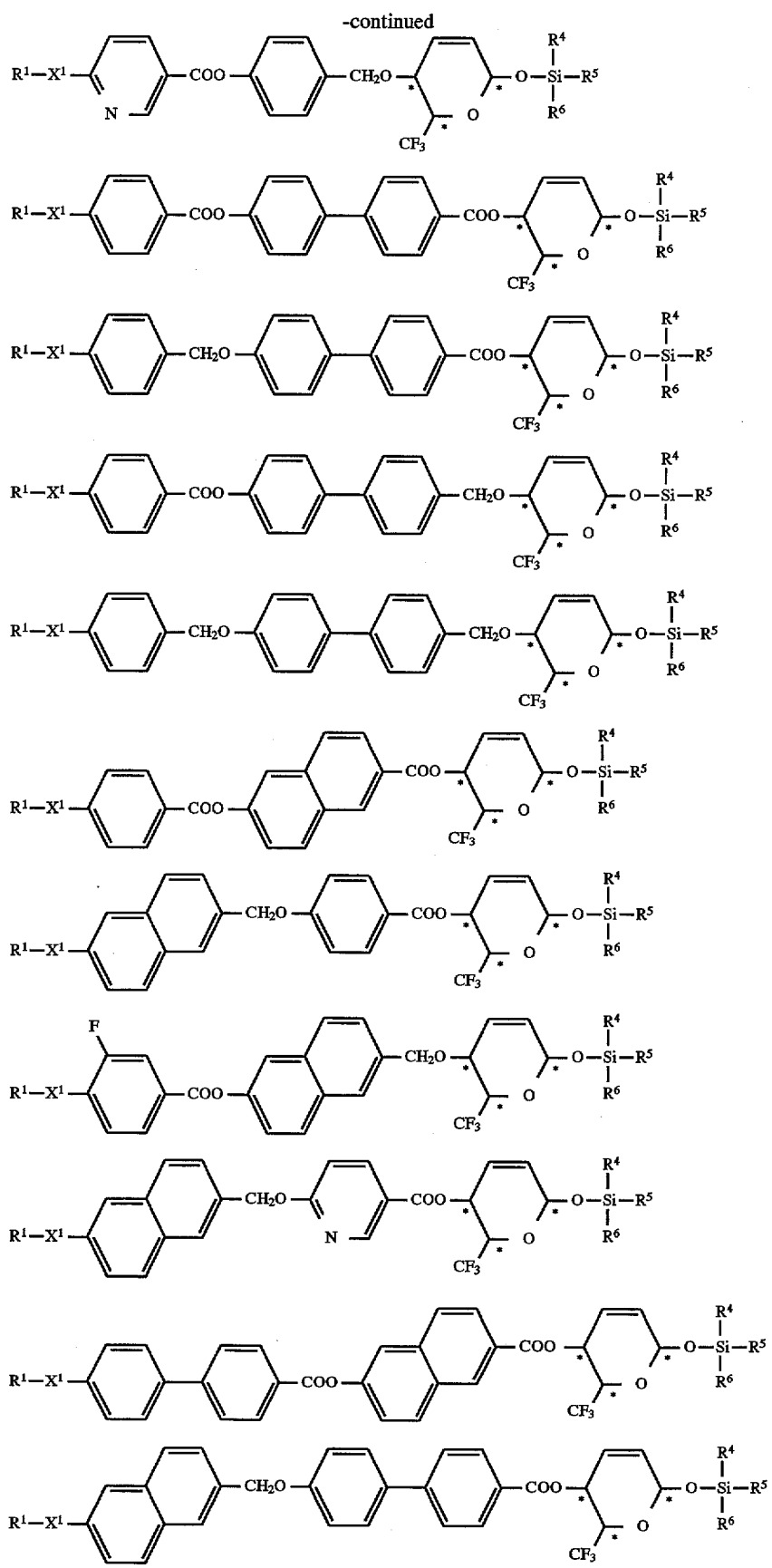

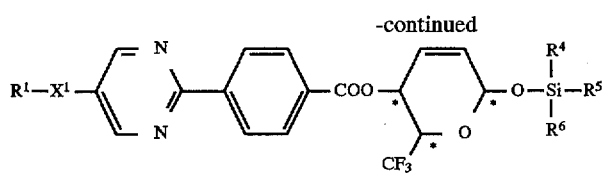
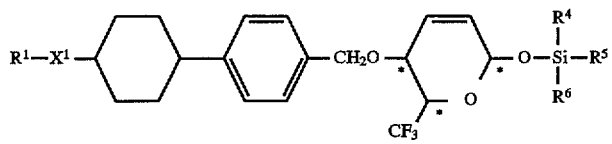
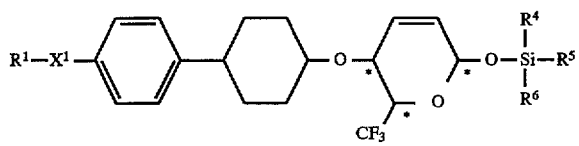
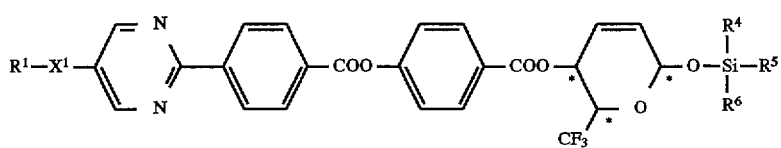
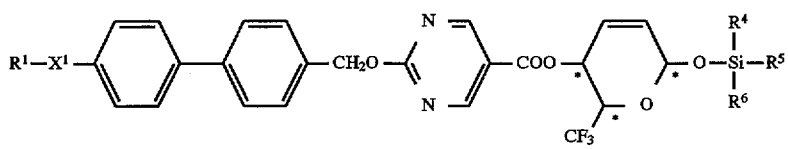
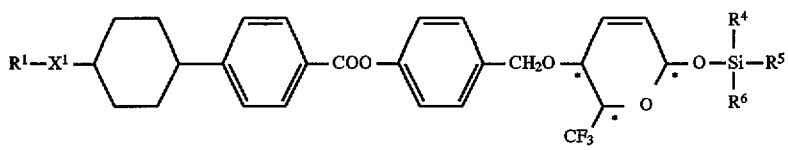
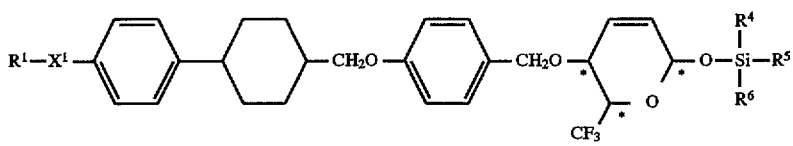
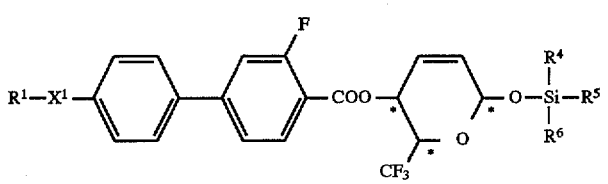
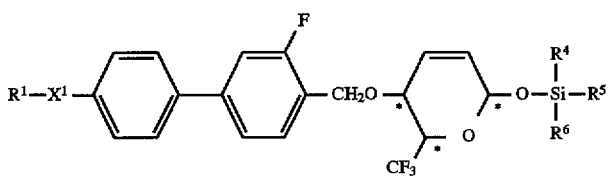
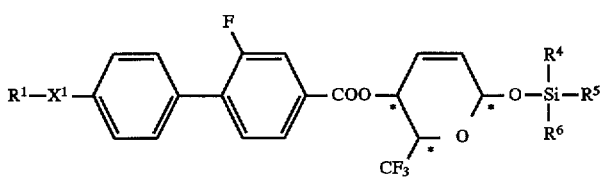

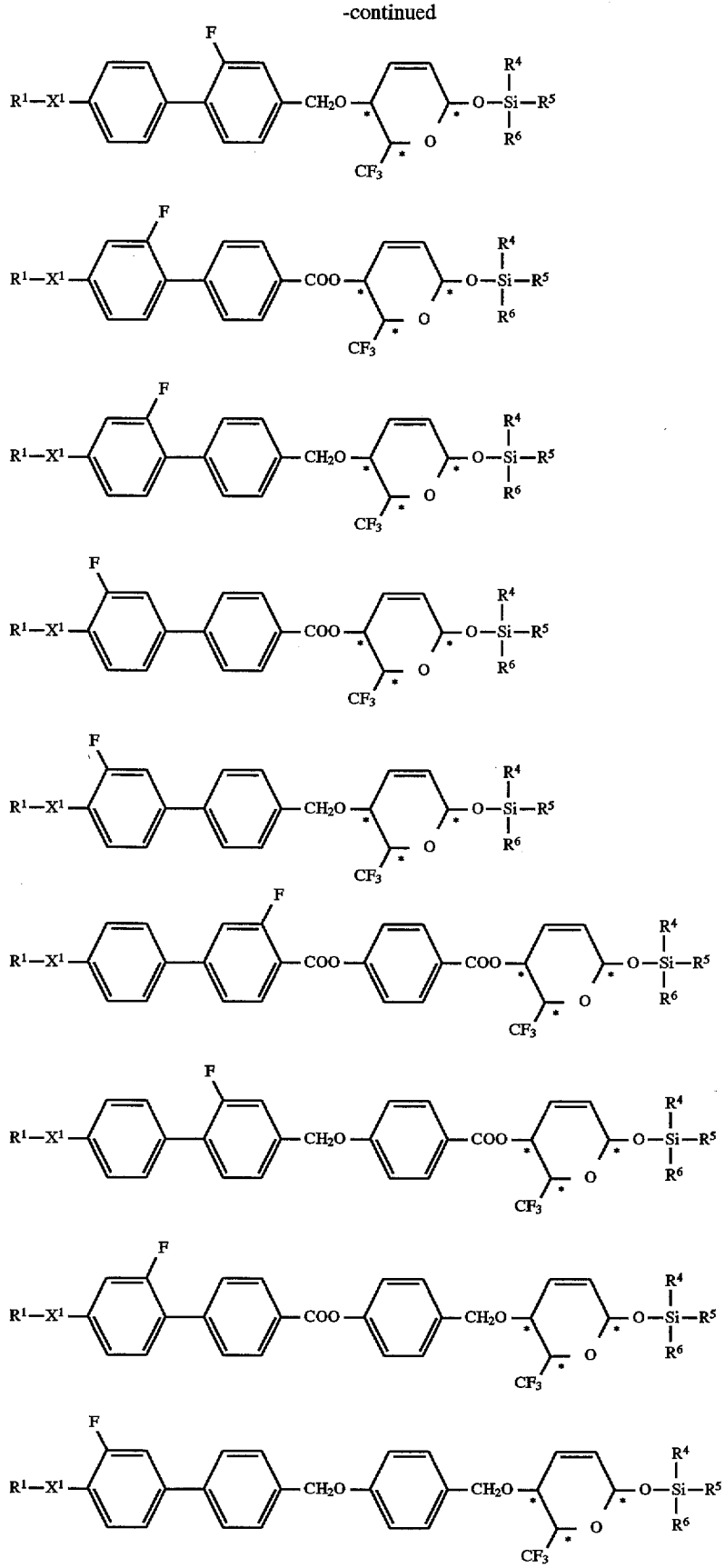

-continued
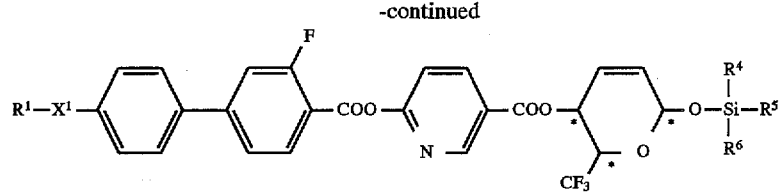
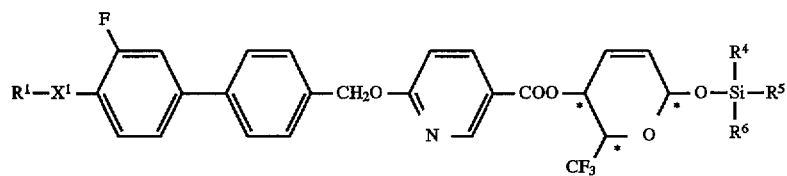
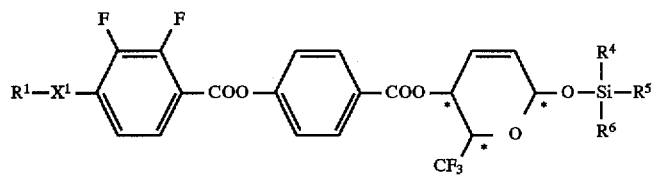
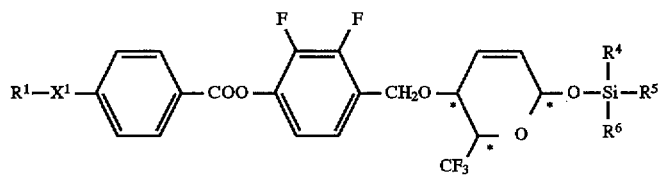
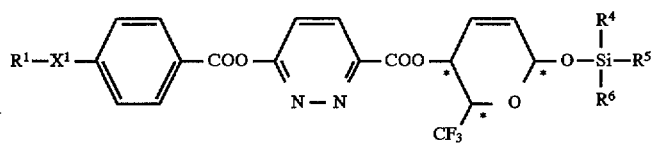
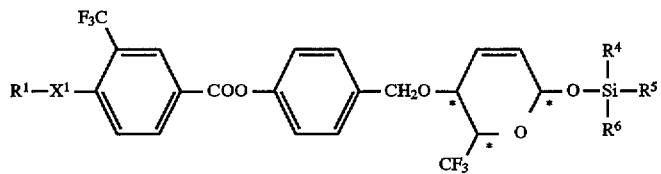
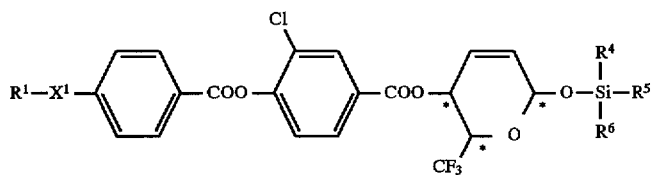
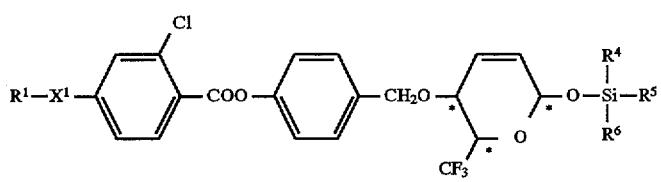
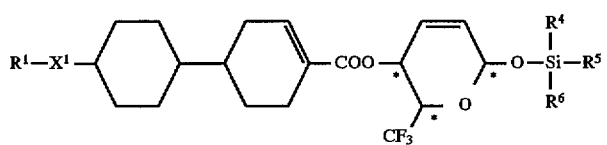

-continued
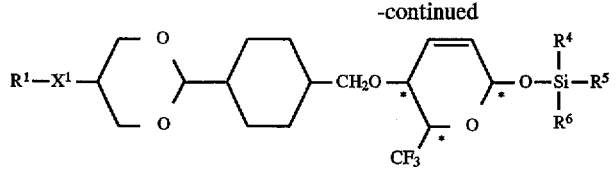
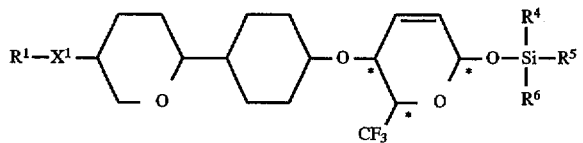
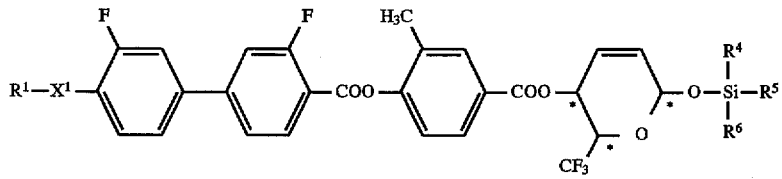
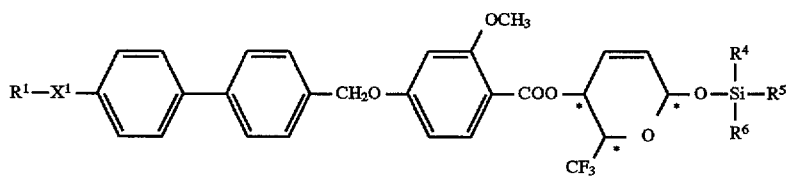
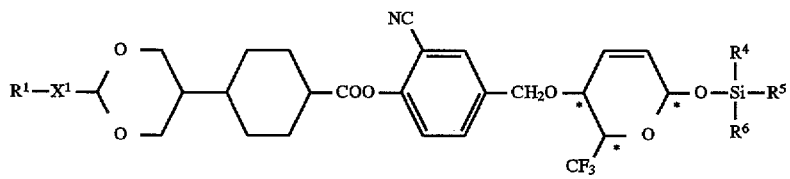
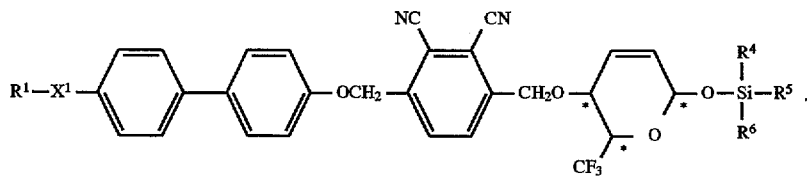
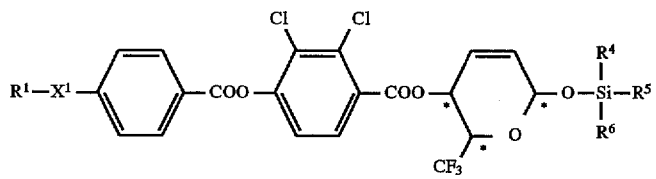
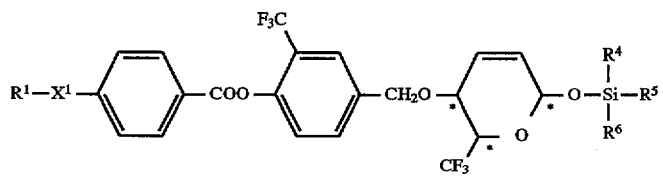
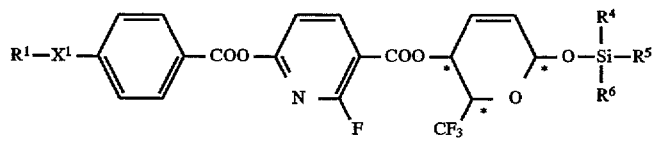

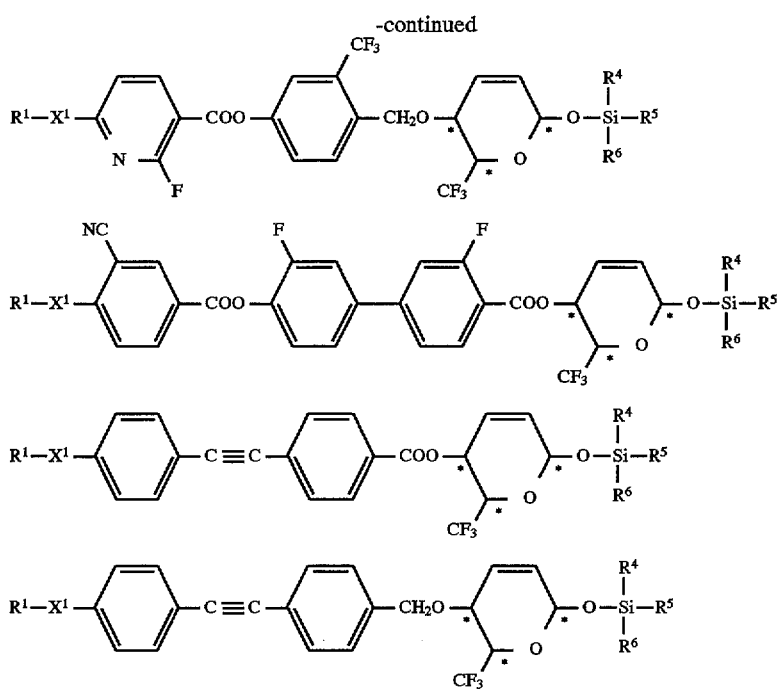
In the above formulae, $R^1$, $R^4$, $R^5$, $R^6$, $X^1$, Si, and * are the same as those described above.
Examples of the compound of the present invention represented by the general formula (I') in which $R^2$ is a group represented by the general formula (III) and obtained as described above include the following compounds.
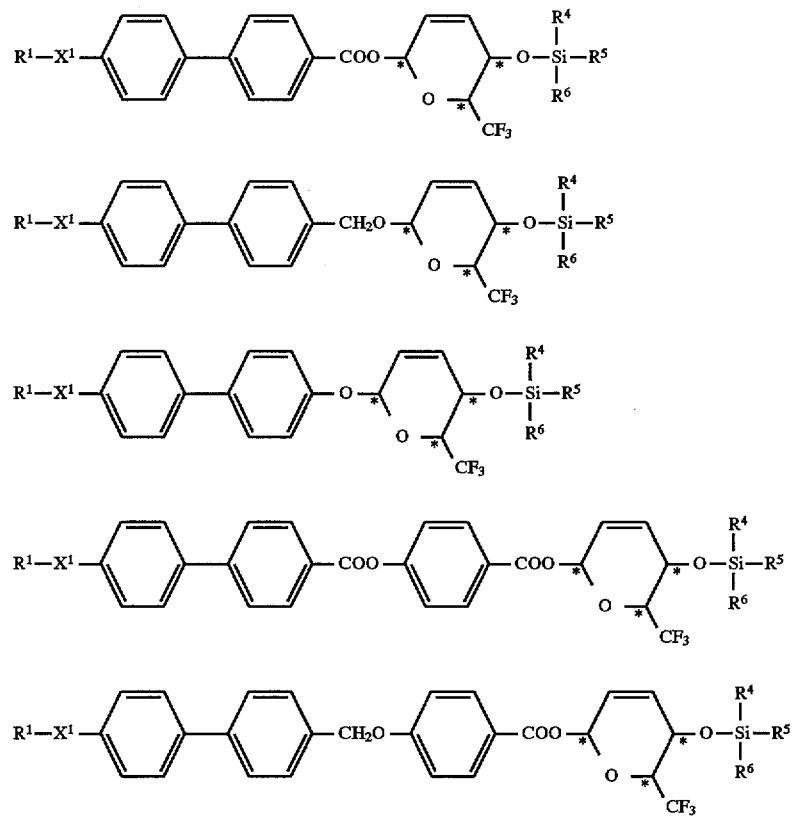

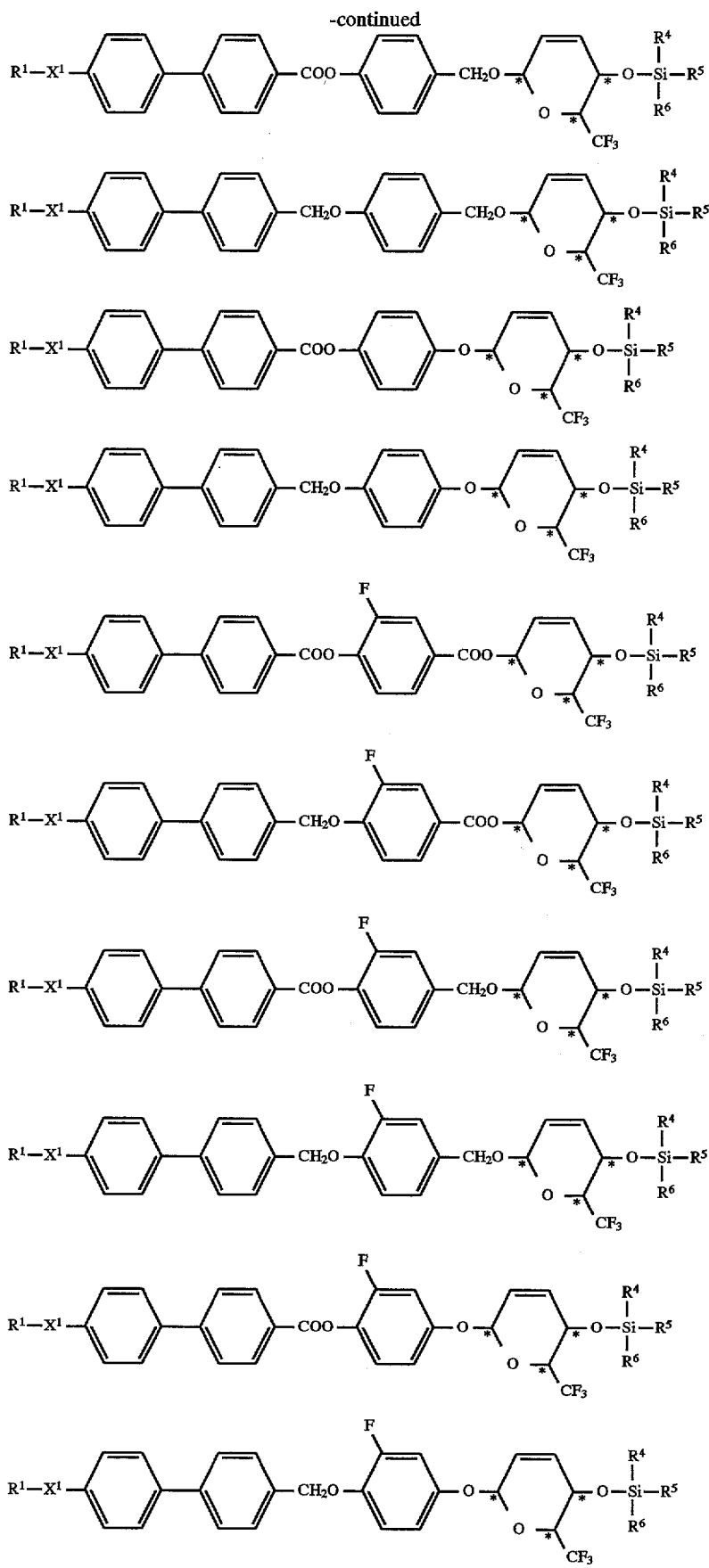

-continued
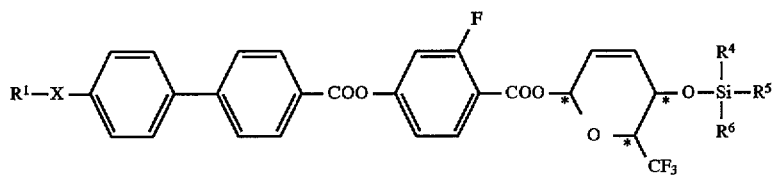
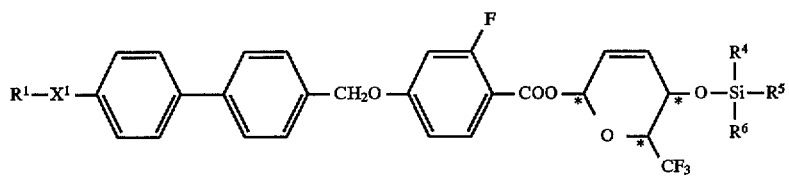
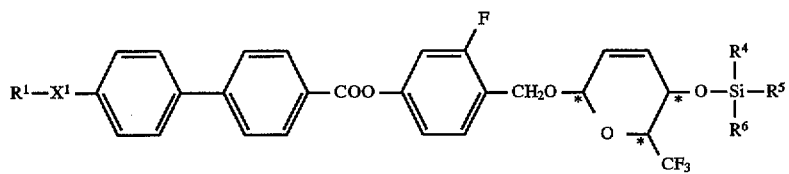
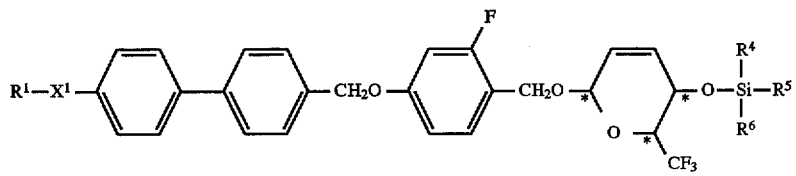
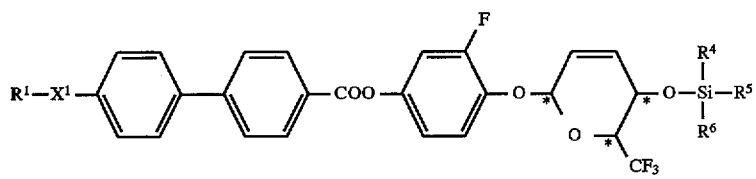
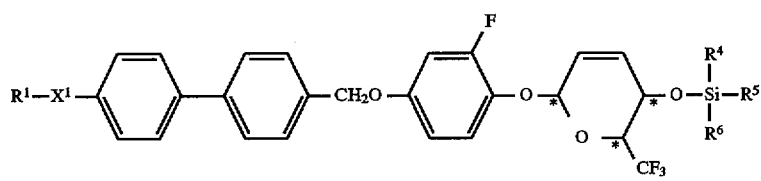
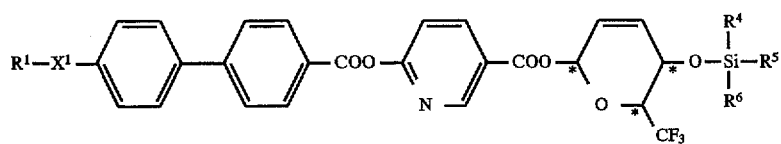
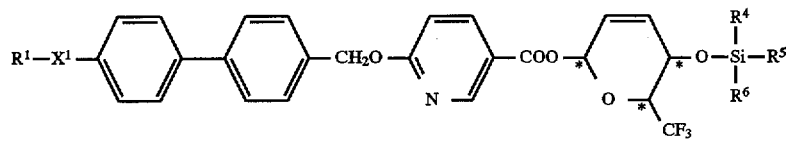
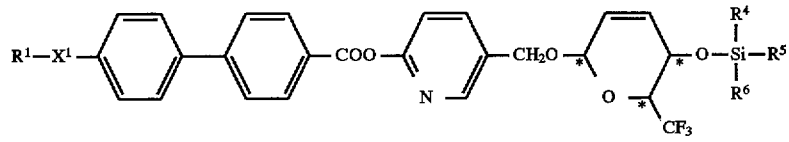

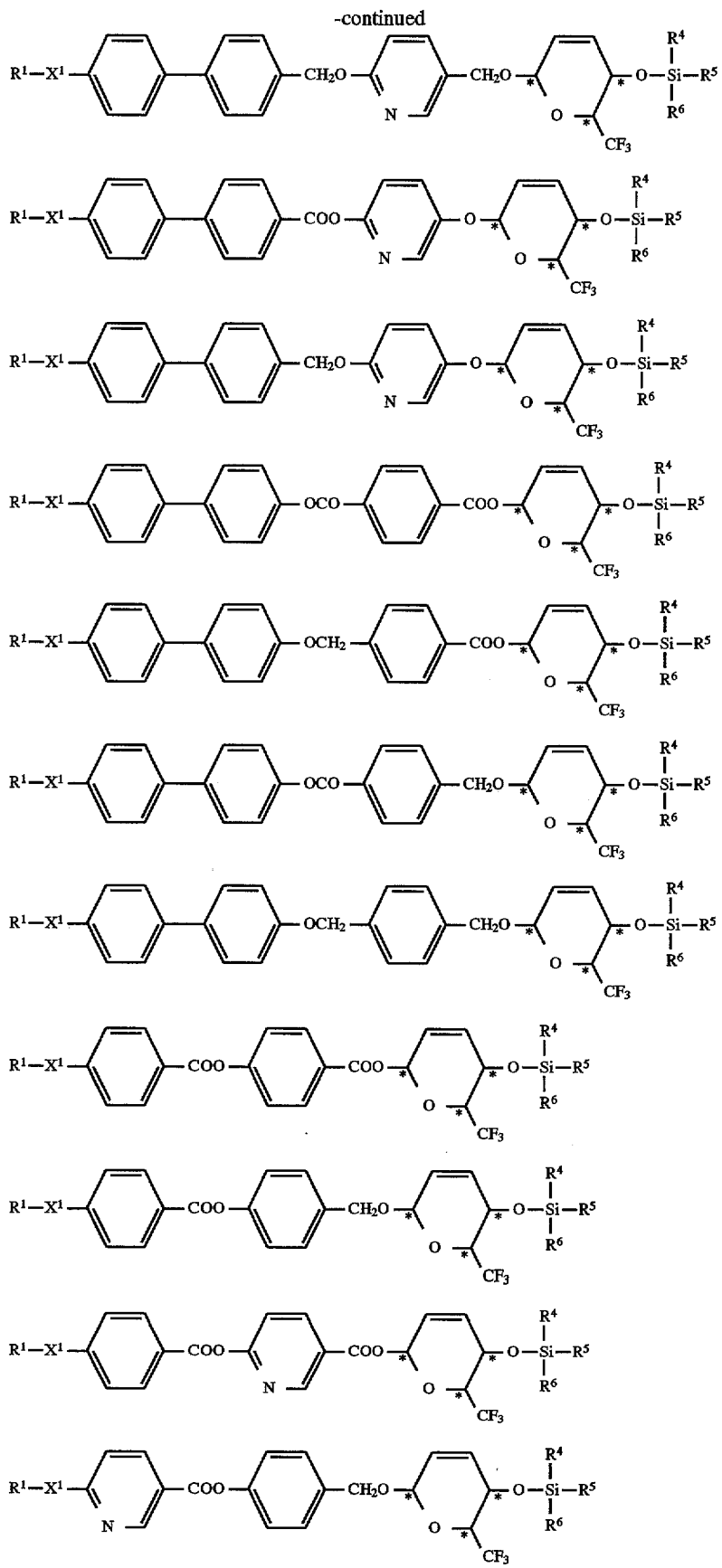

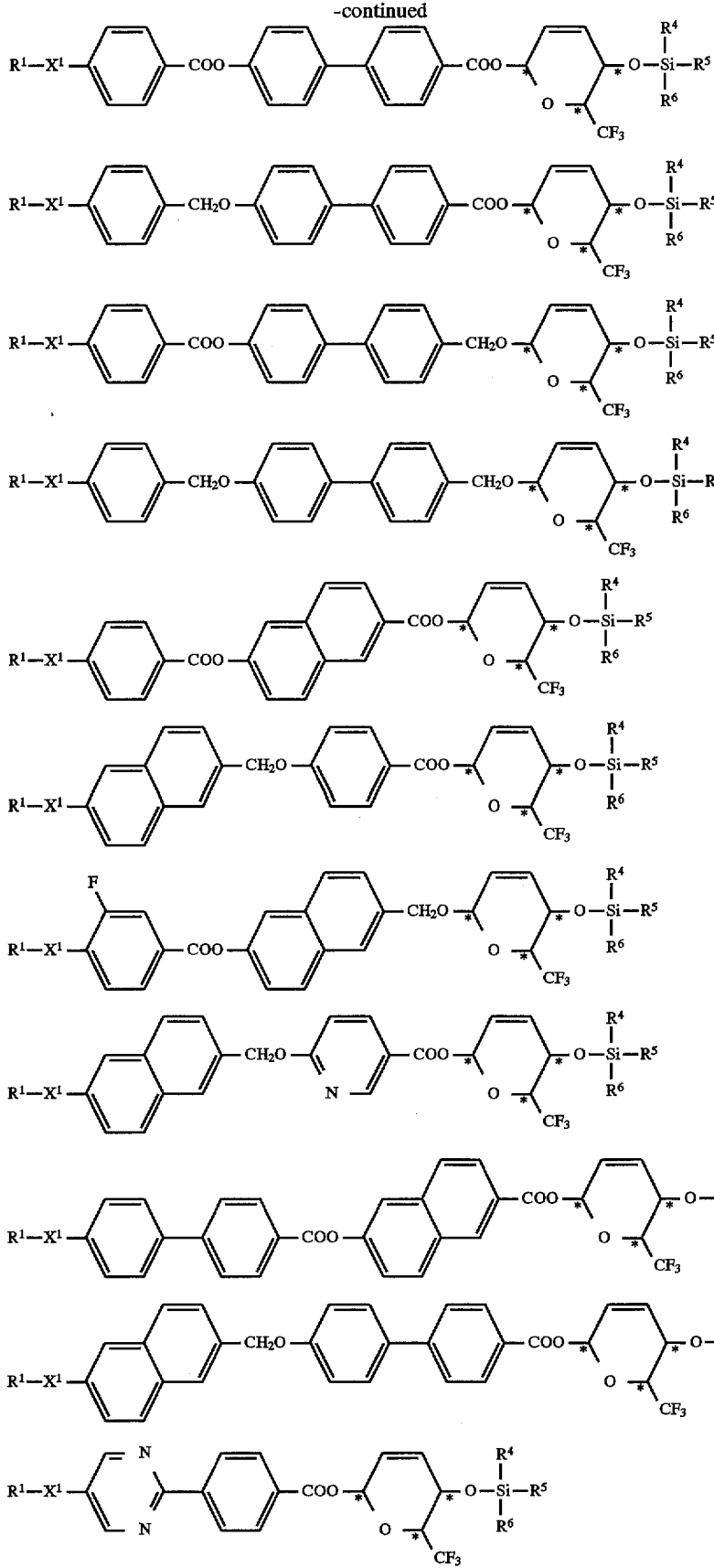

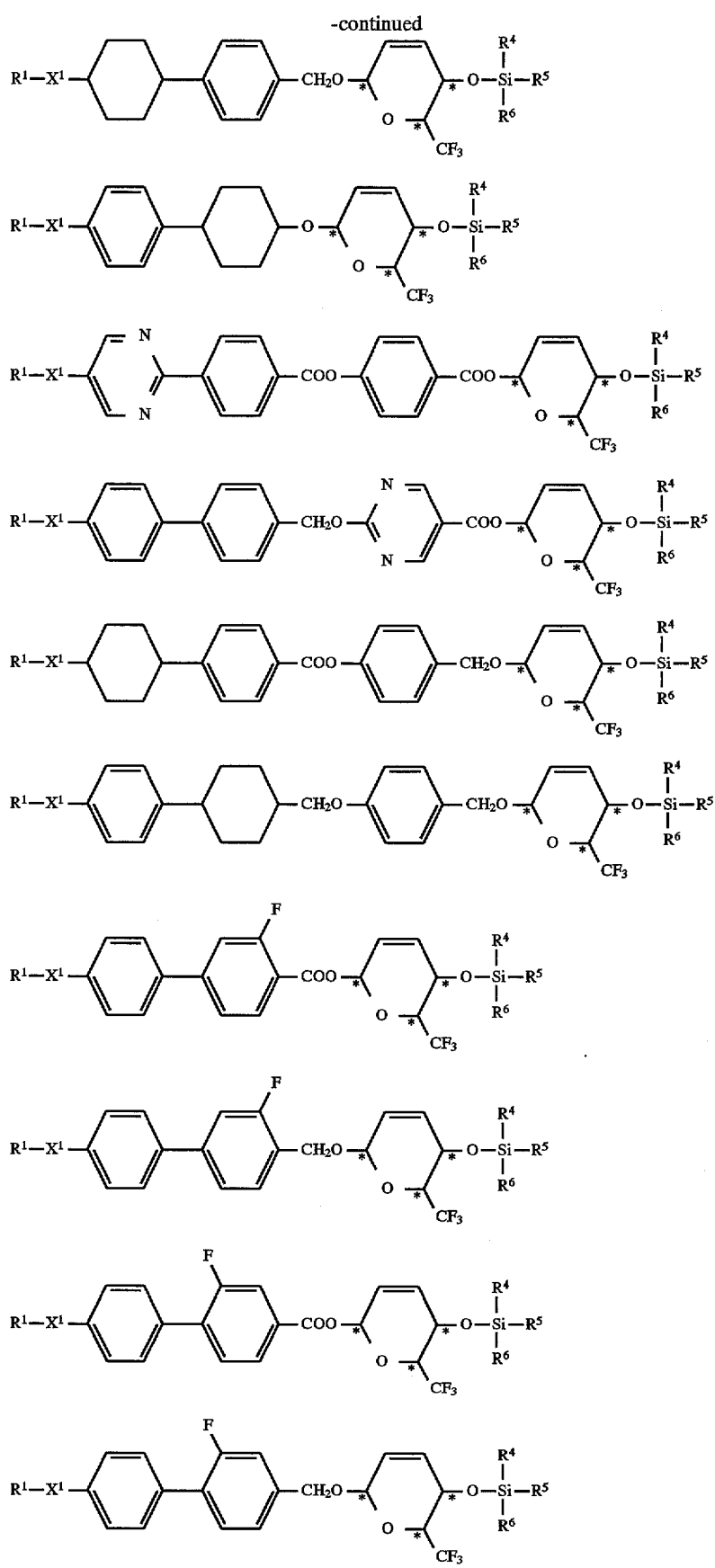

-continued
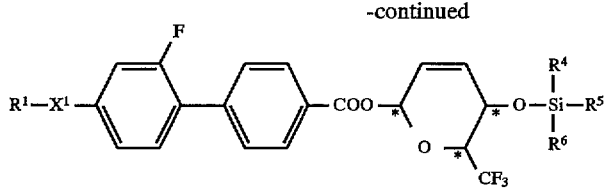
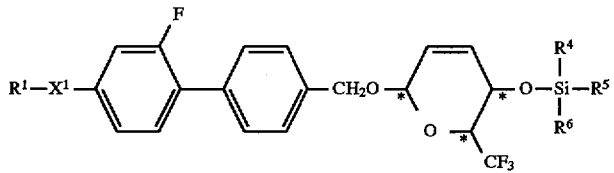
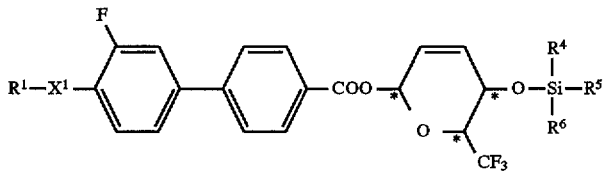
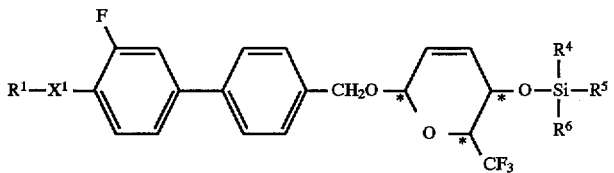
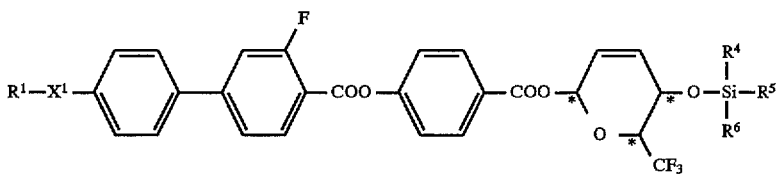
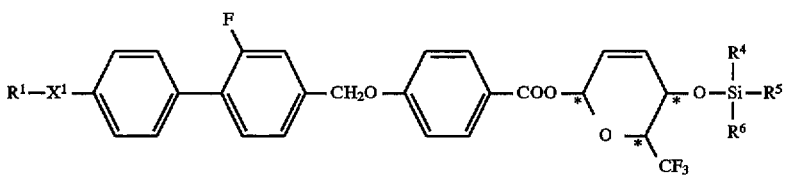
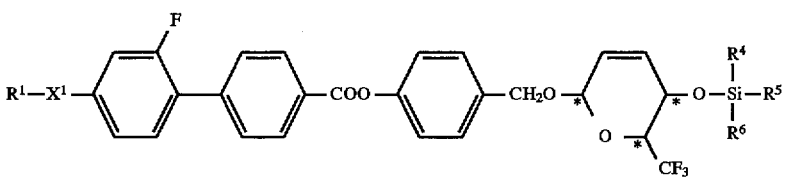
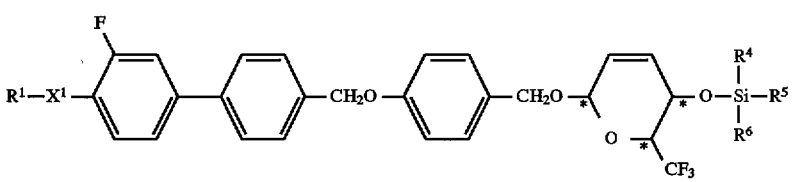
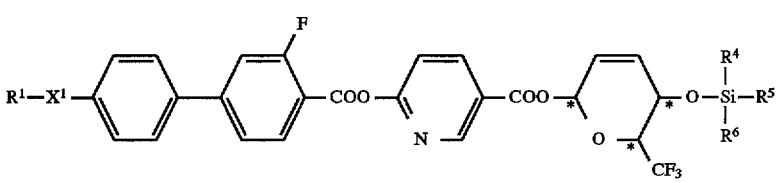

-continued
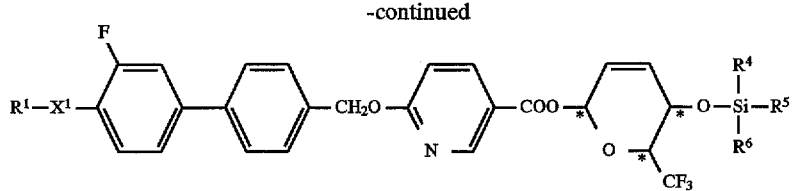
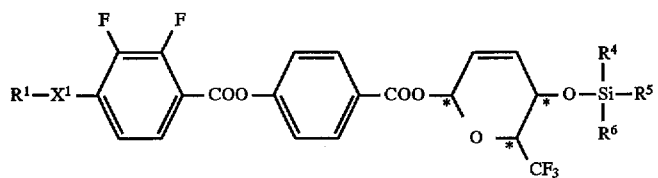
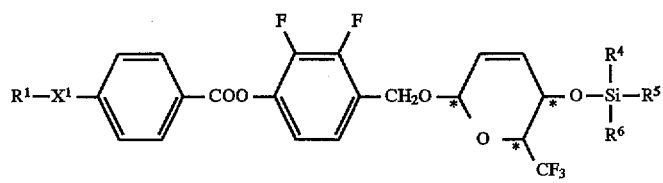
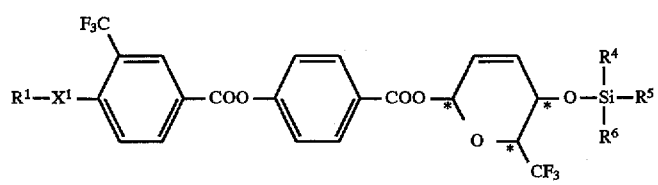
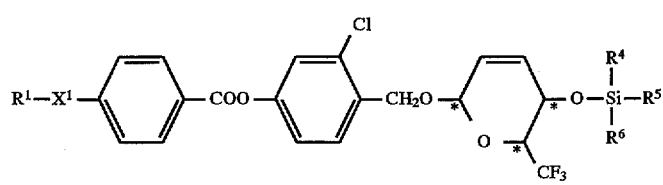
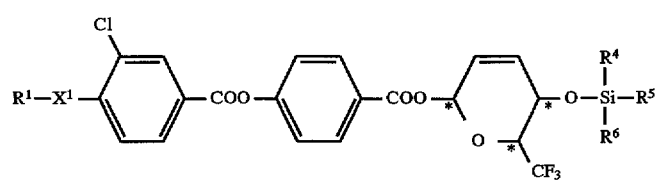
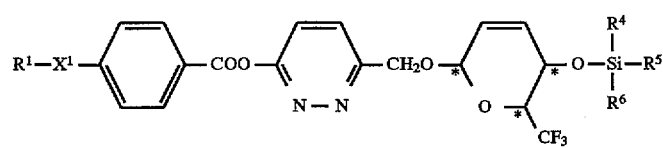
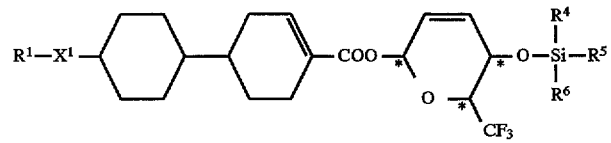
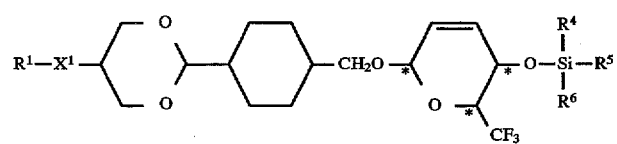
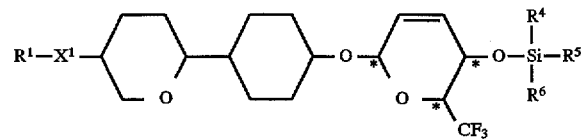

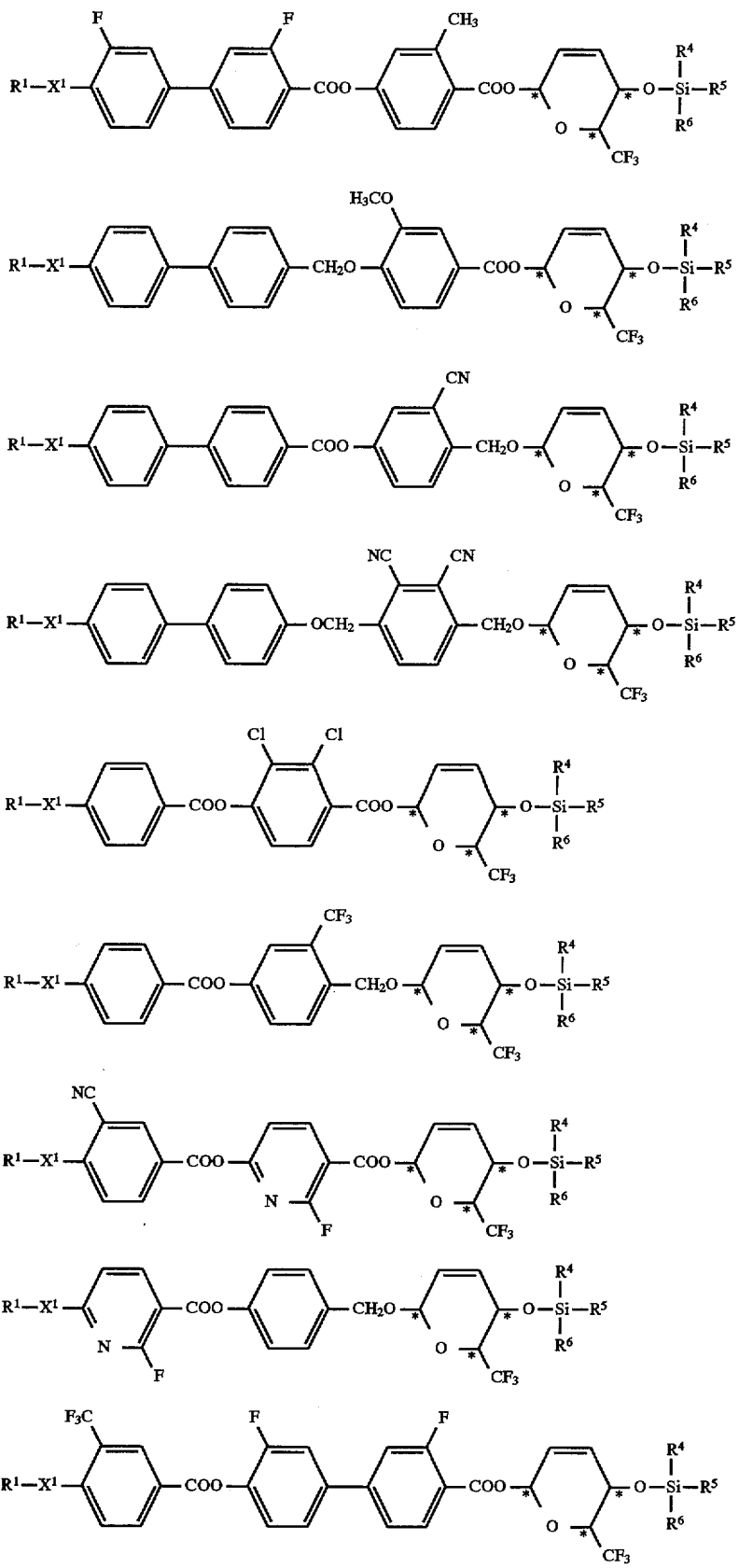

-continued

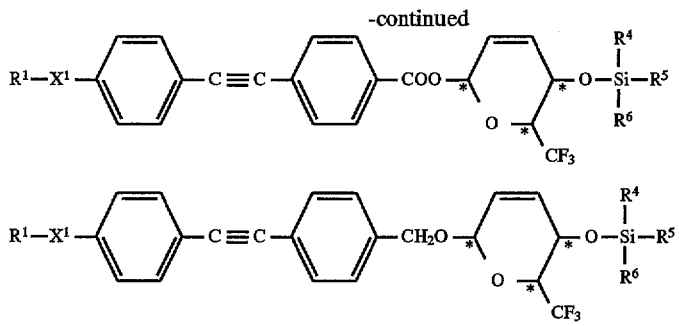

In the above formulae, $R^1$, $R^4$, $R^5$, $R^6$, $X^1$, Si, and * are the same as those described above.

The liquid crystal composition of the present invention can be obtained by mixing together:
(a) at least one type selected from the compounds represented by the general formula (I) or (I'),
(b) a compound or a mixture having a chiral smectic C phase (SmC*) excluding the optically active dihydropyran derivative used in (a), and/or
(c) a compound or a mixture having a smectic C phase (SmC) excluding the optically active dihydropyran derivative used in (a).

The content of the compound represented by the general formula (I) or (I') in the liquid crystal composition can be selected suitably in accordance with the related conditions. The content is preferably 0.1 to 99% by weight, more preferably 1 to 90% by weight in the liquid crystal composition.

In another embodiment of the present invention, the liquid crystal composition comprises at least two types selected from the compounds represented by the general formula (I) or (I').

As the compound or the mixture of the component (b) or (c), various types of conventional compounds or mixtures can be used.

Specific examples of the compound used as the component (b) include compounds described in Table 7.1 in page 229 of "Structure and Properties of Ferroelectric Liquid Crystals", published by Corona Co., 1990. More specific examples of the compound used as the component (b) include the following compounds. Examples of the compounds having the structure:

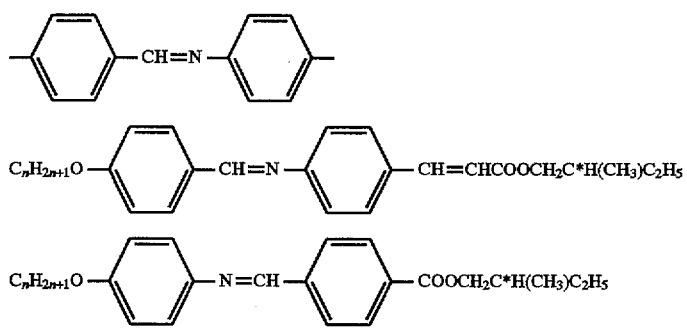

An example of the compound having the structure:

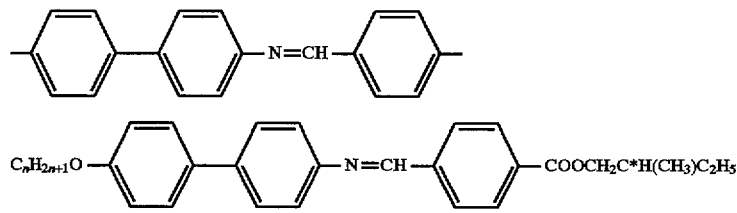

An example of the compound having the structure:

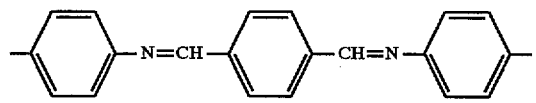

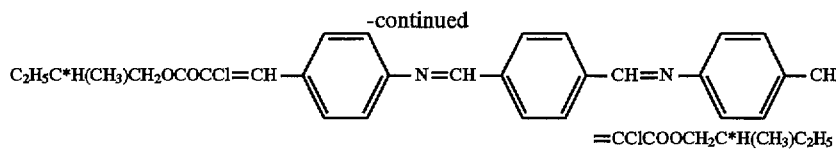

An example of the compound having the structure:

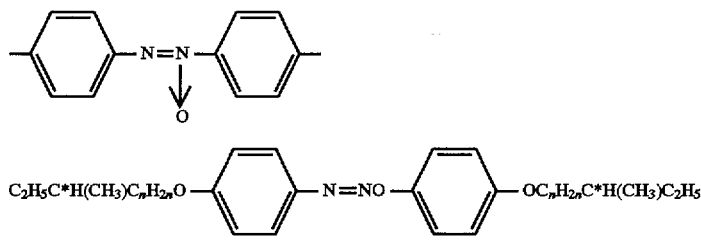

An example of the compound having the structure:

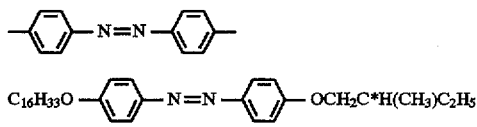

An example of the compound having the structure:

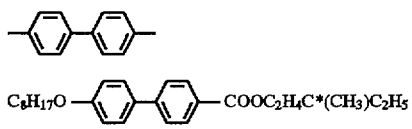

Examples of the compound having the structure:

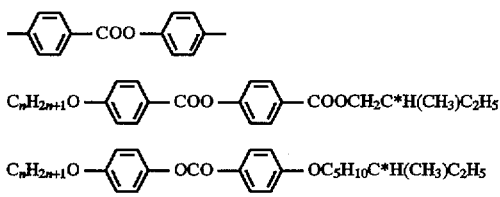

Examples of the compound having the structure:

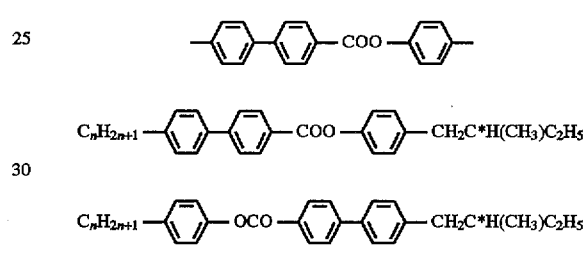

Examples of the compound having the structure:

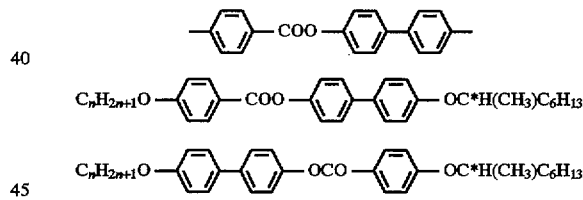

Examples of the compound having the structure:

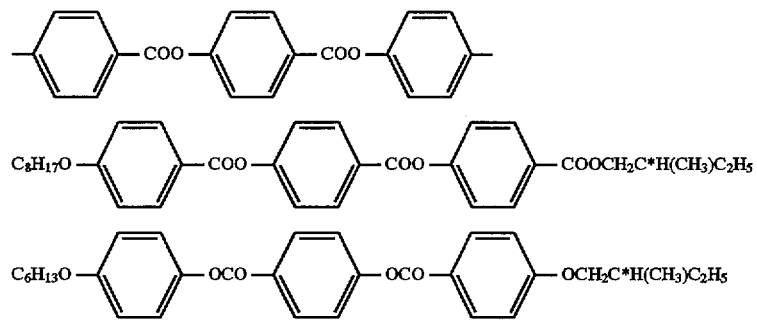

An example of the compound having the structure:

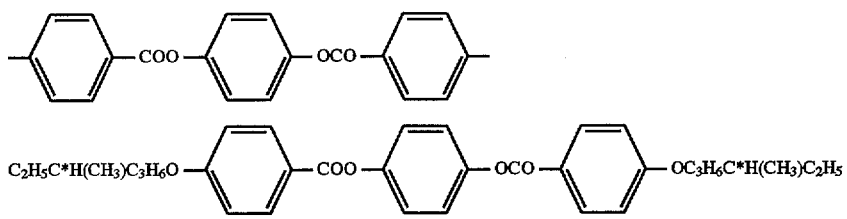
An example of the compound having the structure:
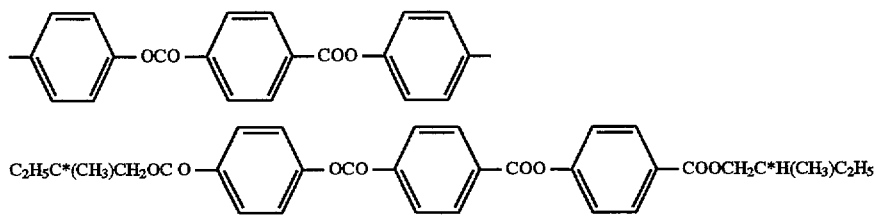
Examples of the compound having the structure:
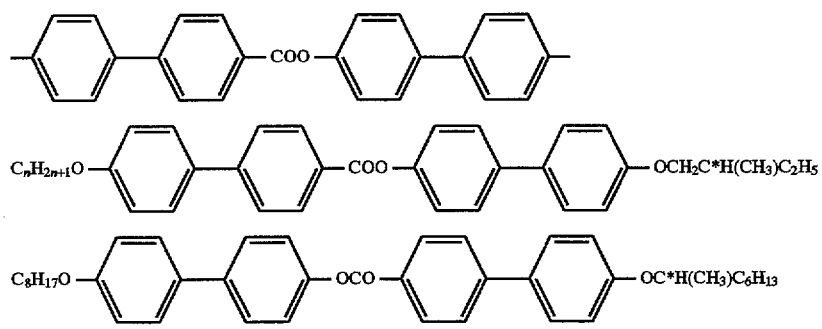
An example of the compound having the structure:
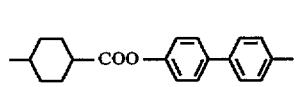
-continued
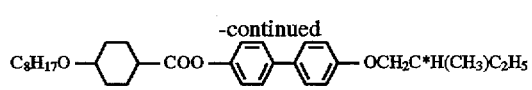
An example of the compound having the structure:
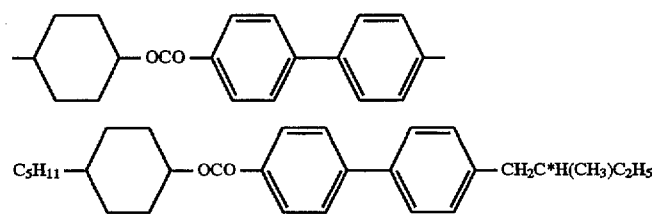
An example of the compound having the structure:
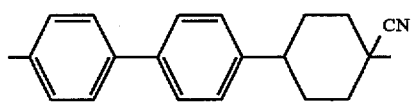

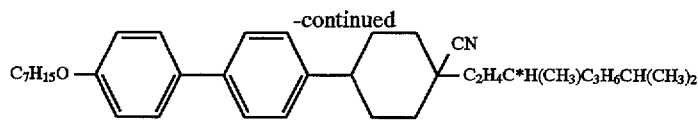
Compounds having the structure:
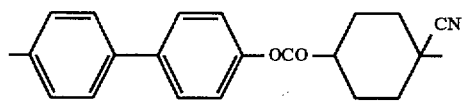
Compounds having the structure:
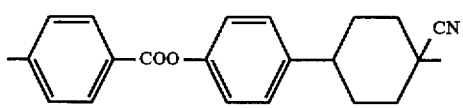
Compounds having the structure:
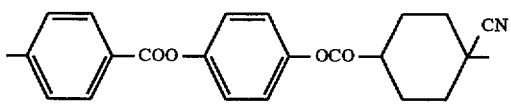
Compounds having the structure:
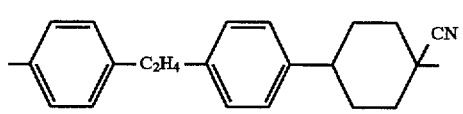
Compounds having the structure:
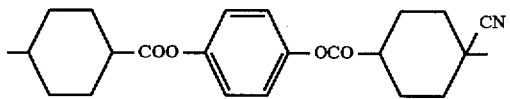
Examples of the compound having the structure:
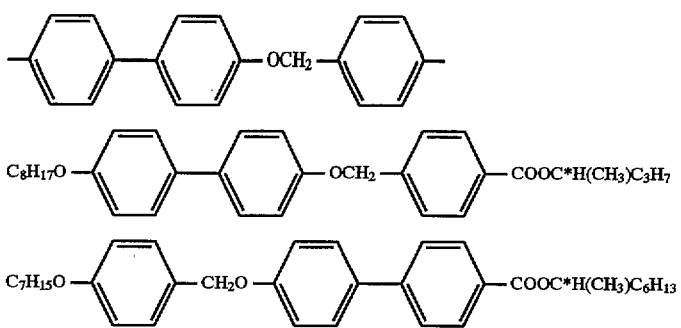
Examples of the compound having the structure:
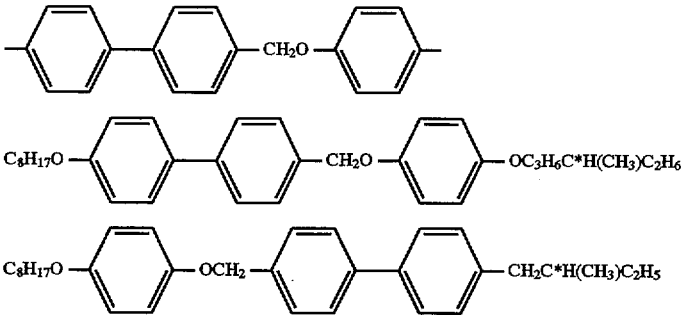
An example of the compound having the structure:

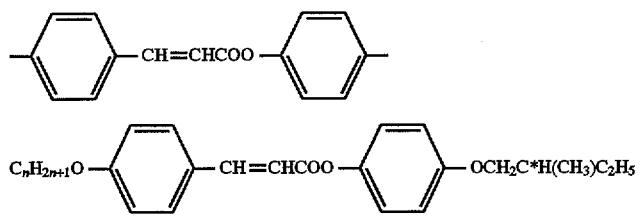
Examples of the compound having the structure:
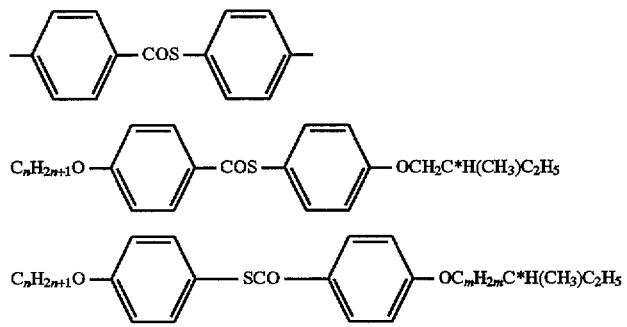
An example of the compound having the structure:
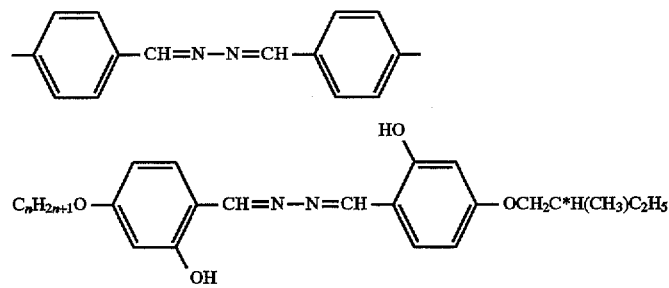
Examples of the compound having the structure:
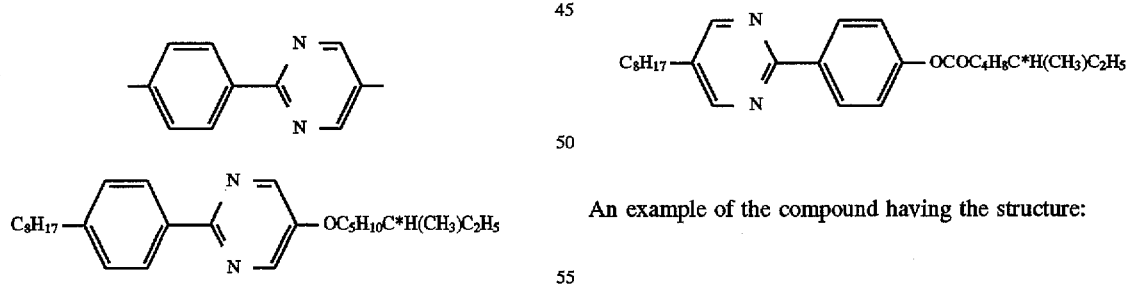
An example of the compound having the structure:
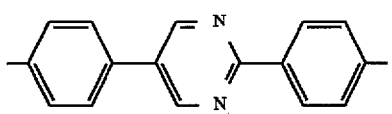

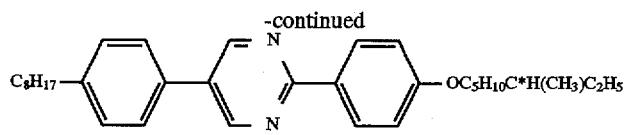
An example of the compound having the structure:
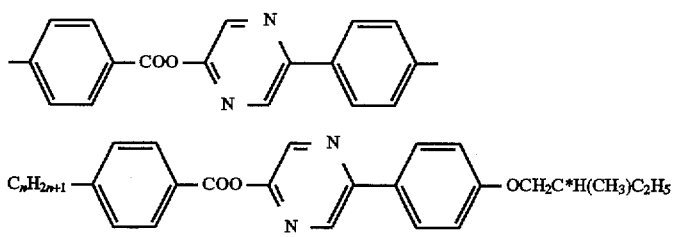
An example of the compound having the structure:
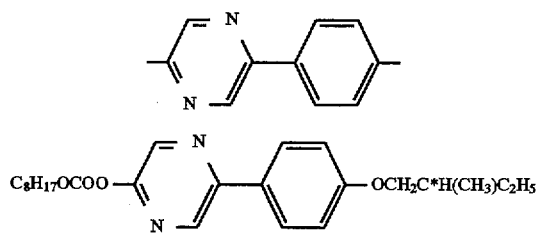
An example of the compound having the structure:
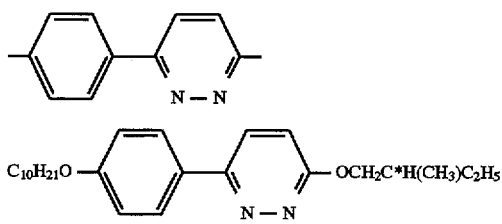
An example of the compound having the structure:
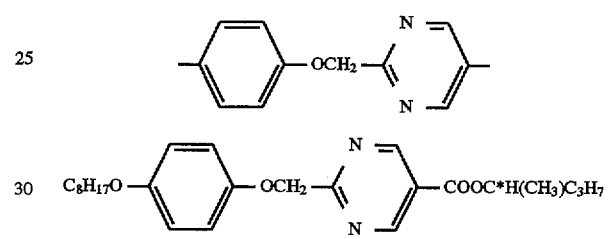
An example of the compound having the structure:
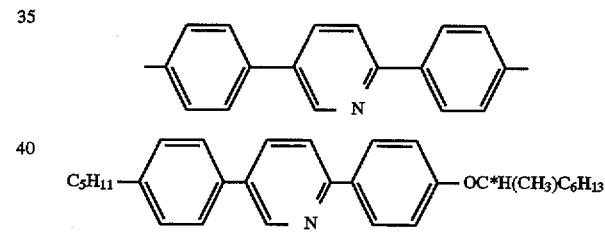
An example of the compound having the structure:
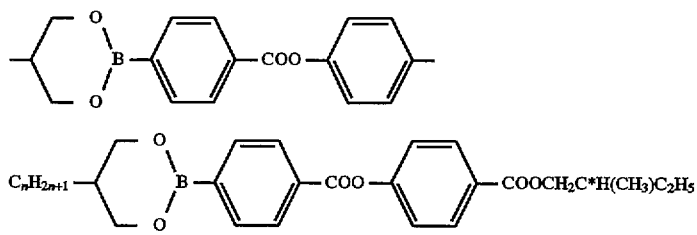
An example of the compound having the structure:
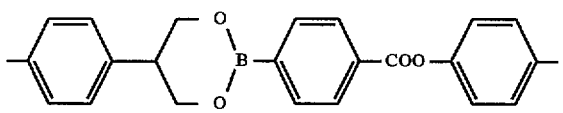

-continued
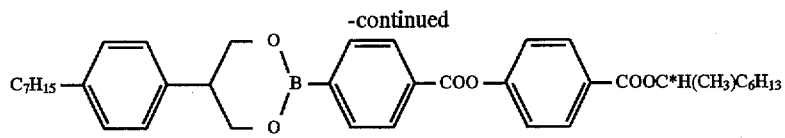
Examples of the compound having the structure:
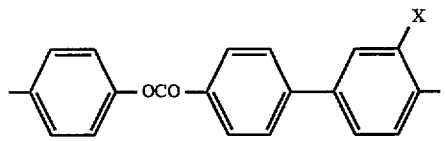
X: H, F, Cl, Br, CN
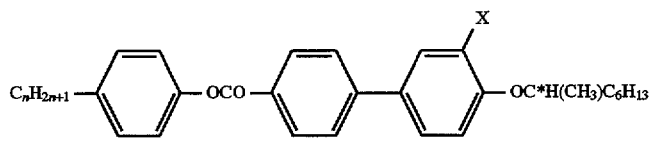
Examples of the compound having the structure:
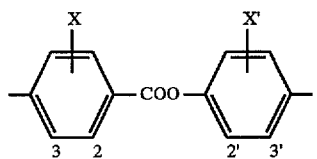
X: H, H, H, H, 3-F, 3-Cl, 2-F, 2-Cl
X': 3'-F, 3'-Cl, 2'-F, 2'-Cl, H, H, H, H
-continued
$C_{10}H_{21}O$—⬡—COO—⬡—$COOCH_2C^*H(CH_3)C_2H_5$
(with X at 3,2 and X' at 2',3')
An example of the compound having the structure:
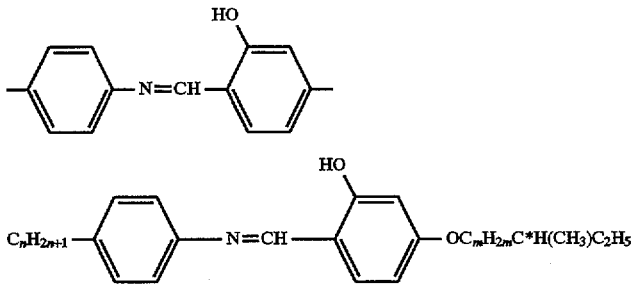

Preferable examples of the compound used as the component (c) include compounds represented by the following general formula:

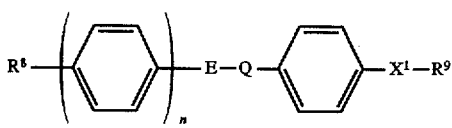

[wherein $R^8$ represents a substituted or unsubstituted alkyl or alkoxy group having 1 to 15 carbon atoms, $R^9$ represents a substituted or unsubstituted alkyl group having 1 to 15 carbon atoms, Q represents —O—, —COO—, —OCO—, —OCOO—, or a single bond, E represents

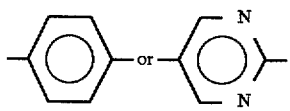

n represents 0 or 1, and $X^1$ is the same as that described above]. Specific examples of the compound used as the component (c) include the following compounds.

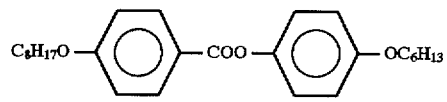

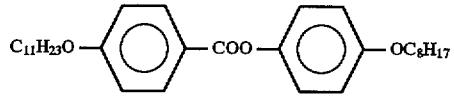

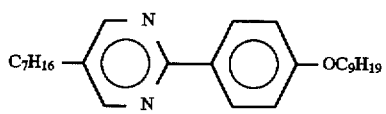

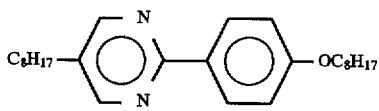

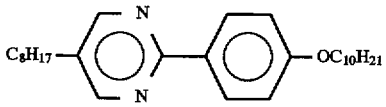

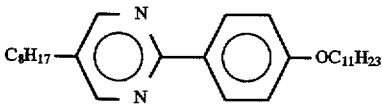

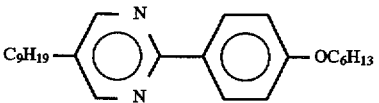

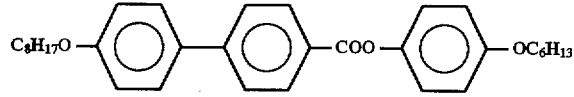

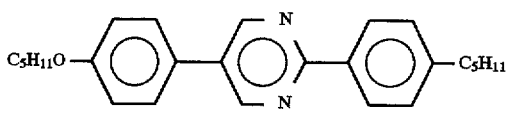

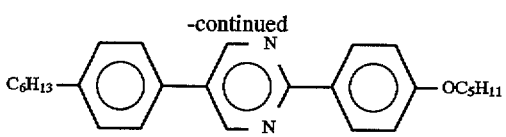

The liquid crystal device of the present invention comprises the above-described liquid crystal composition which comprises the compound represented by the general formula (I) or (I') and is disposed between a pair of electrode plates. The electrode plate comprises a transparent substrate plate, a transparent electrode which is made from, for example, $InO_3$, $SnO_2$, or ITO (a mixed oxide of indium oxide and tin oxide) which is disposed on the transparent substrate plate, and an alignment film which is made of polyvinyl alcohol or polyimide which is disposed on the transparent electrode and polarizing plates disposed on the other sides of transparent substrate plates.

In other words, the liquid crystal device of the present invention can be obtained by disposing the liquid crystal composition described above between a pair of the alignment film described above, and by subsequently disposing a transparent electrode on the both sides of the resultant combination. The liquid crystal device can be used as a display device or an electro-optical device by using it in the birefringence mode.

To summarize the advantages of the invention, the optically active dihydropyran derivative of the present invention is a novel compound which is chemically stable, does not cause coloring, and is excellent in light stability. This compound exhibits a high speed response.

Therefore, the optically active dihydropyran derivative of the present invention decreases response time of a composition which comprises the derivative, and is useful as a component in a ferroelectric liquid crystal which induces a high spontaneous polarization.

The invention will be described with reference to the following reference examples and examples.

In the following examples, R or S in the optically active compounds represented by the general formula (I) or (I') of the present invention is indicated with reference to the position numbers shown in the following formulae:

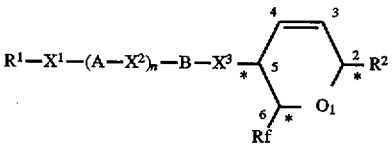

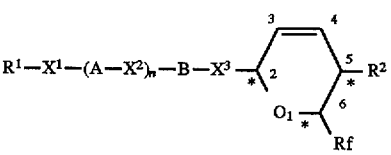

[wherein Rf, $R^1$, $R^2$, $X^2$, $X^2$, $X^3$, A, B, n, and * are the same as those described above].

REFERENCE EXAMPLE 1

Synthesis of (5S,6S)-2H-5,6-dihydro-5-tert-butyldimethylsiloxy-6-trifluoromethyl-2-hydroxypyran

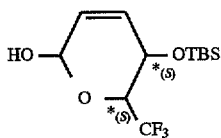

In the above formula, TBS and * are the same as those described above.

(a) Under an atmosphere of nitrogen, 13.6 g (200 mmol) of furan was added to 150 ml of tetrahydrofuran. A 1.5 mol/liter solution of n-butyllithium in hexane in an amount of 133 ml (200 mmol) was added dropwise to the resultant solution at −20° C., and the reaction was allowed to proceed for 1 hour. To the obtained reaction mixture, 21.7 g (200 mmol) of trimethylsilyl chloride was added dropwise, and the mixture was stirred at −20° C. for further 1 hour. Then, 133 ml (200 mmol) of a 1.5 mol/liter solution of n-butyllithium in hexane was added to the mixture, and the reaction was allowed to proceed at −20° C. for 1 hour. To the resultant reaction mixture, 28.4 g (200 mmol) of ethyl trifluoroacetate was added dropwise at −78° C., and the reaction was allowed to proceed at −78° C. for 1 hour and then at a room temperature for 1 hour. The reaction was stopped by addition of 3N hydrochloric acid. The resultant reaction mixture was extracted with ethyl acetate. The extract was washed with a saturated solution of sodium hydrogen carbonate and a saturated aqueous solution of sodium chloride successively, and then dried with anhydrous magnesium sulfate. Ethyl acetate was removed from the solution by distillation under a vacuum to obtain a crude product of the furan derivative.

(b) To 100 ml of dry ethanol, 2.3 g (60 mmol) of sodium borohydride was added, and then the crude product of the furan derivative obtained above was added to the resultant mixture dropwise in 30 minutes at 0° C. After the reaction was allowed to proceed at a room temperature for 2 hours, ethanol was removed by distillation under a vacuum. The reaction was stopped by addition of 3N hydrochloric acid. The resultant reaction mixture was extracted with ethyl acetate. Then, the extract was washed with a saturated solution of sodium hydrogen carbonate and a saturated aqueous solution of sodium chloride successively, and then dried with anhydrous magnesium sulfate. Ethyl acetate was removed from the solution by distillation under a vacuum, and the remaining product was distilled under a vacuum to obtain 40.5 g (170 mmol) of an alcohol compound.

(c) To 300 ml of methylene chloride, 64.1 g (269 mmol) of the alcohol compound obtained by the reaction in (b) and 27.7 ml (350 mmol) of pyridine were added. To the resultant mixture, 27.5 g (350 mmol) of acetyl chloride was added dropwise at 0° C., and the reaction was allowed to proceed at a room temperature for 2 hours. The reaction was stopped by addition of 3N hydrochloric acid. The resultant reaction mixture was extracted with methylene chloride. Then, the extract was washed with a saturated solution of sodium hydrogen carbonate and distilled water successively, and then dried with anhydrous magnesium sulfate. Methylene chloride was removed from the solution by distillation under a vacuum, and the remaining product was distilled under a vacuum to obtain 75.1 g (268 mmol) of an ester compound.

(d) To 1800 ml of distilled water, 58.5 g (209 mmol) of the ester compound obtained by the above reaction was added, and the mixture was stirred in a mini-jar fermenter at 40° C. To the mixture, 30 g of lipase PS was added, and the reaction was allowed to proceed for 10 hours. The reaction was stopped by addition of 3N hydrochloric acid and cooling to 0° C. The obtained reaction mixture was filtered by using celite, and the filtrate was extracted with ethyl acetate. The extract was washed with a saturated aqueous solution of sodium chloride and dried with anhydrous magnesium sulfate. Ethyl acetate was removed from the obtained solution under a vacuum. The resultant product was purified with separation by using the silica-gel column chromatography to obtain 23.2 g (97.4 mmol) of an optically active alcohol compound and 25.6 g (91.4 mmol) of an optically active ester compound. The optical purity of the obtained alcohol compound was 98.0% e.e.

(e) Into 200 ml of methylene chloride, 25.8 g (108 mmol) of the optically active alcohol compound obtained by the above reaction was dissolved. To the resultant solution, 10.5 g (151 mmol) of imidazole and 23.0 g (151 mmol) of t-butyldimethylsilyl chloride were added at 0° C., and the mixture was stirred for 15 minutes. The reaction was allowed to proceed at a room temperature for 16 hours, and then stopped by addition of distilled water. The reaction mixture was extracted with methylene chloride. The extract was washed with distilled water and dried with anhydrous magnesium sulfate. Methylene chloride was removed from the dried extract by distillation under a vacuum, and the resultant product was purified with separation by using the column chromatography to obtain 37.2 g (106 mmol) of a silyl ether compound.

(f) Under an atmosphere of nitrogen, 14.1 g (40 mmol) of the silyl ether compound obtained by the above reaction and 23.2 g (60 mmol) of magnesium monoperoxyphthalate were added to 120 ml of acetic acid, and the reaction was allowed to proceed at 80° C. for 12 hours. Acetic acid was removed from the mixture by distillation under a vacuum, and a saturated solution of sodium hydrogen carbonate was added to the remaining product. The resultant mixture was extracted with ethyl acetate. Then, the obtained extract was washed with a saturated aqueous solution of sodium chloride and dried with anhydrous magnesium sulfate. Ethyl acetate was removed from the solution by distillation under a vacuum. The remaining product was purified with separation by using the column chromatography to obtain 4.7 g (16 mmol) of a (4S,1'S)butenolide compound and 3.0 g (10 mmol) of a (4R,1'S)butenolide compound. The starting material in an amount of 4.2 g (12 mmol) was also recovered.

(g) Under an atmosphere of nitrogen, 0.95 g (3.2 mmol) of the (4S,1')butenolide compound obtained by the above reaction was added to 4 ml of diethyl ether. To the resultant solution, 4.23 ml (3.94 mmol) of a 0.93 mol/liter solution of diisobutylaluminum hydride in n-hexane was added dropwise at −78° C., and the reaction was allowed to proceed for 3 hours. The reaction was stopped by addition of distilled water, and the reaction product was filtered with celite. The obtained filtrate was extracted with diethyl ether. The extract was washed with a saturated aqueous solution of sodium chloride and dried with anhydrous magnesium sulfate. Diethyl ether was removed from the dried extract by distillation under a vacuum. The remaining product was purified by using the silica-gel column chromatography to obtain 0.75 g (2.52 mmol) of a lactol compound.

(h) Under an atmosphere of nitrogen, 1.00 g (3.36 mmol) of the lactol compound obtained by the above reaction was added to 2 ml of tetrahydrofuran. To the resultant solution, 2 ml of a tetrahydrofuran solution containing 0.45 g(4.02 mmol) of potassium tert-butoxide was added dropwise at −78° C. The reaction was allowed to proceed for 5 hours and then stopped by addition of distilled water. The obtained solution was neutralized by addition of 1N hydrochloric acid and extracted with diethyl ether. The extract was washed with a saturated aqueous solution of sodium chloride and dried with anhydrous magnesium sulfate. Diethyl ether was removed from the dried extract by distillation under a vacuum. The remaining product was purified by using the silica-gel column chromatography to obtain 0.54 g (1.81 mmol) of the object compound: (5S,6S)-2H-5,6-dihydro-5-tert-butyldimethylsiloxy-6-trifluoro-methyl-2-hydroxypyran. The measurement of nuclear magnetic resonance using the isotope of fluorine showed that the obtained compound was a mixture of diastereomers in a ratio by mol of 95:5.

Physical properties of the obtained compounds are shown in the following.

Molecular formula: $C_{12}H_{21}F_3O_3Si$ $^1$H-NMR (proton nuclear magnetic resonance); δ(ppm)

| | |
|---|---|
| 0.06 | (s, 3H) |
| 0.09 | (s, 3H) |
| 0.87 | (s, 9H) |
| 3.06 | (d, J=5.0 Hz, 1H) |
| 4.16 | (ddq, J=0.6, 8.7, 6.4 Hz, 1H) |
| 4.40 | (dddd, J=1.2, 1.3, 1.5, 8.9 Hz, 1H) |
| 5.84 | (m, 1H) |

$^{19}$F-NMR (nuclear magnetic resonance of an isotope of fluorine, reference compound: $CF_3COOH$); δ(ppm)

| | |
|---|---|
| 3.8 | (d, J=6.1 Hz) |

REFERENCE EXAMPLE 2

Synthesis of (2R,5S,6S)-2H-5,6-dihydro-6-trifluoromethyl-2-hexyloxy-5-hydroxypyran and (2S,5S,6S)-2H-5,6-dihydro-6-trifluoro-methyl-2-hexyloxy-5-hydroxypyran

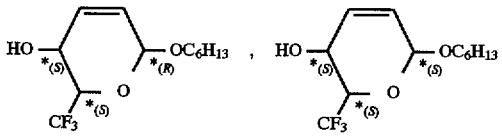

(a) Into 10 ml of hexanol, 1.00 g (3.36 mmol) of (5S,6S)-2H-5,6-dihydro-5-tert-butyldimethylsiloxy-6-trifluoromethyl-2-hydroxypyran obtained in Reference Example 1 (h) was dissolved. To the obtained solution, 0.1 g of para-toluenesulfonic acid was added, and the reaction was allowed to proceed at a room temperature for 18 hours. The reaction product was purified by using the silica-gel column chromatography without further treatment to obtain 1.21 g (3.15 mmol) of an acetal compound. The obtained compound was a mixture of diastereomers and used for the next reaction without separation.

(b) Into 10 ml of tetrahydrofuran, 1.21 g (3.15 mmol) of the acetal compound obtained by the above reaction was dissolved. To the resultant solution, 1.6 ml of a 1.0 mol/liter solution of tetra-n-butylammonium fluoride in tetrahydrofuran was added, and the reaction was allowed to proceed at 0° C. for 1 hour and then at a room temperature for further 3 hours. The reaction was stopped by addition of distilled water, and the reaction solution was extracted with diethyl ether.

The extract was washed with a saturated aqueous solution of sodium chloride and dried with anhydrous magnesium sulfate. Diethyl ether was removed from the dried extract by distillation under a vacuum, and the remaining product was purified with separation by using the silica-gel column chromatography to obtain the object compounds: 0.71 g (2.65 mmol) of (2R,5S,6S)-2H-5,6-dihydro-6-trifluoromethyl-2-hexyloxy-5-hydroxypyran and 0.09 g (0.32 mmol) of (2S,5S,6S)-2H-5,6-dihydro-6-trifluoromethyl-2-hexyloxy-5-hydroxypyran.

Physical properties of the obtained compounds are shown in the following.

(1) The (2R,5S,6S) isomer

Molecular formula: $C_{12}H_{19}F_3O_3$ $^1$H-NMR (proton nuclear magnetic resonance); δ(ppm)

| | |
|---|---|
| 0.89 | (t, J=6.5 Hz, 3H) |
| 1.26~1.38 | (m, 6H) |
| 1.58~1.68 | (m, 2H) |
| 2.09 | (d, J=6.5 Hz, 1H) |
| 3.53 | (dt, J=9.6, 6.5 Hz, 1H) |
| 3.78 | (dt, J=9.6, 6.8 Hz, 1H) |
| 4.10 | (dq, J=9.1, 6.4 Hz, 1H) |
| 4.42~4.49 | (m, 1H) |
| 5.04~5.06 | (m, 1H) |
| 5.79~5.85 | (m, 1H) |
| 5.89~5.93 | (m, 1H) |

$^{19}$F-NMR (nuclear magnetic resonance of an isotope of fluorine, reference compound: $CFCl_3$); δ(ppm)

| | |
|---|---|
| −76.10 | (d, J=6.4 Hz) |

$[α]_D^{26} = +52.8°$ (C. (concentration)=1.02, solvent: methanol)

(2) The (2S,5S,6S) isomer

Molecular formula: $C_{12}H_{19}F_3O_3$ $^1$H-NMR (proton nuclear magnetic resonance); δ(ppm)

| | |
|---|---|
| 0.88 | (t, J=6.7 Hz, 3H) |
| 1.25~1.37 | (m, 6H) |
| 1.54~1.67 | (m, 2H) |
| 2.19 | (d, J=6.3 Hz, 1H) |
| 3.52 | (dt, J=8.1, 6.8 Hz, 1H) |
| 3.87 | (dt, J=8.1, 6.7 Hz, 1H) |
| 3.99 | (dq, J=6.8, 6.8 Hz, 1H) |
| 4.43~4.53 | (m, 1H) |
| 5.18~5.19 | (m, 1H) |
| 5.83~5.89 | (m, 1H) |
| 5.94~5.99 | (m, 1H) |

$^{19}$F-NMR (nuclear magnetic resonance of an isotope of fluorine, reference compound: $CFCl_3$); δ(ppm)

| | |
|---|---|
| −75.87 | (d, J=6.7 Hz) |

$[α]_D^{24} = +31.2°$ (C. (concentration)=0.63, solvent: methanol)

EXAMPLE 1

Synthesis of (2R,5S,6S)-2H-5,6-dihydro-2-hexyloxy-6-trifluoro-methyl-5-(4″-hexyloxybiphenyl-4′-carbonyloxy)pyran

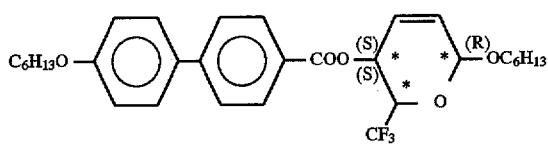

Into 10 ml of a toluene solution containing 0.21 g (0.38 mmol) of 4'-hexyloxy-4-biphenylcarboxylic acid chloride and 0.09 g (0.32 mmol) of (2R,5S,6S)-2H-5,6-dihydro-6-trifluoroethyl-2-hexyloxy-5-hydroxypyran obtained in Reference Example 2, 0.31 ml (2.23 mmol) of triethylamine was added, and the reaction was allowed to proceed at a room temperature for 24 hours. The reaction was stopped by addition of 1N hydrochloric acid to the reaction solution, and the resultant solution was extracted with diethyl ether. The extract was washed with a saturated aqueous solution of sodium chloride and dried with anhydrous magnesium sulfate. Diethyl ether was removed from the dried extract by distillation under a vacuum, and the remaining product was purified by using the silica-gel column chromatography to obtain 0.10 g (0.17 mmol) of the object compound: (2R,5S,6S)-2H-5,6-dihydro-2-hexyloxy-6-trifluoro-methyl-5-(4"-hexyloxybiphenyl-4'-carbonyloxy)pyran.

Physical properties of the obtained compound are shown in the following.

Molecular formula: $C_{31}H_{39}O_5F_3$ $^1$H-NMR; $\delta$(ppm)

| | |
|---|---|
| 0.87–0.94 | (m, 6H) |
| 1.25–1.66 | (m, 14H) |
| 1.76–1.84 | (m, 2H) |
| 3.56 | (dt, J=6.7, 9.3 Hz, 1H) |
| 3.93 | (dt, J=6.7, 9.3 Hz, 1H) |
| 4.01 | (t, J=6.5 Hz, 2H) |
| 4.37 | (dq, J=6.6, 6.7 Hz, 1H) |
| 5.29 | (ddd, J=1.4, 1.5, 1.7 Hz, 1H) |
| 5.77–5.81 | (m, 1H) |
| 6.01 | (ddd, J=1.3, 1.3, 10.4 Hz, 1H) |
| 6.08 | (ddd, J=1.5, 2.9, 10.4 Hz, 1H) |
| 6.99 | (d, J=8.7 Hz, 2H) |
| 7.35 | (d, J=8.5 Hz, 2H) |
| 7.56 | (d, J=8.8 Hz, 2H) |
| 8.06 | (d, J=8.4 Hz, 2H) |

$^{19}$F-NMR (reference compound: CF $Cl_3$); $\delta$(ppm)

| | |
|---|---|
| −76.09 | (d, J=6.7 Hz) | mass analysis m/e (M$^+$+H) calculated 548.2750 found 548.2775

EXAMPLE 2

Synthesis of (2S,5S,6S)-2H-5,6-dihydro-6-trifluoromethyl-2-(4"-hexyloxybiphenyl-4'-carbonyloxy)-5-hexyloxypyran

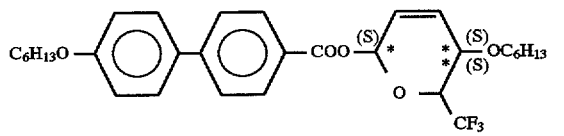

a) Under an atmosphere of nitrogen, 10 ml of a tetrahydrofuran solution containing 1.11 g (4.12 mmol) of (2R,5S,6S)-2H-5,6-dihydro-6-trifluoromethyl-2-hexyloxy-5-hydroxypyran obtained in Reference Example 2 was added dropwise into 7 ml of a tetrahydrofuran solution containing 0.12 g (4.93 mmol) of sodium hydride at 0° C. To the obtained solution, 0.696 ml (4.93 mmol) of hexyl bromide and 4 ml of dimethylsulfoxide were added, and the reaction was allowed to proceed at a room temperature for 24 hours. The reaction was stopped by adding distilled water to the reaction solution, and the resultant solution was extracted with diethyl ether. The extract was washed with a saturated aqueous solution of sodium chloride and dried with anhydrous magnesium sulfate. Diethyl ether was removed from the dried extract by distillation under a vacuum, and the remaining product was purified by using the silica-gel column chromatography to obtain 1.41 g (4.04 mmol) of an acetal compound.

b) Into 15 ml of tetrahydrofuran, 1.41 g (4.04 mmol) of the acetal compound obtained by the above reaction was dissolved. To the obtained solution, 4 ml of distilled water and 1 ml of a 36N sulfuric acid were added, and the reaction was allowed to proceed at 80° C. for 24 hours. The reaction was stopped by adding 1N potassium hydroxide to the reaction solution, and the resultant solution was extracted with diethyl ether. The extract was washed with a saturated aqueous solution of sodium chloride and dried with anhydrous magnesium sulfate. Diethyl ether was removed from the dried extract by distillation in a vacuum, and the remaining product was purified by using the silica-gel column chromatography to obtain 0.14 g (0.53 mmol) of a hemiacetal compound.

c) Into 10 ml of a solution containing 0.24 g (0.80 mmol) of 4'-hexyloxy-4-biphenylcarboxylic acid chloride and 0.14 g (0.53 mmol) of the hemiacetal compound obtained by the above reaction, 0.11 ml (0.80 mmol) of triethylamine was added, and the reaction was allowed to proceed at a room temperature for 24 hours. The reaction was stopped by addition of 1N hydrochloric acid to the reaction solution, and the resultant solution was extracted with diethyl ether. The extract was washed with a saturated aqueous solution of sodium chloride and dried with anhydrous magnesium sulfate. Diethyl ether was removed from the dried extract by distillation in a vacuum, and the remaining product was purified by using the silica-gel column chromatography to obtain 0.11 g (0.21 mmol) of the object compound: (2S,5S,6S)-2H-5,6-dihydro-6-trifluoromethyl-2-(4"-hexyloxybiphenyl-4'-carbonyloxy)-5-hexyloxypyran.

Physical properties of the obtained compound are shown in the following.

Molecular formula: $C_{31}H_{39}O_5F_3$ $^1$H-NMR; $\delta$(ppm)

| | |
|---|---|
| 0.87–0.94 | (m, 6H) |
| 1.25–1.63 | (m, 14H) |
| 1.78–1.84 | (m, 2H) |
| 3.54 | (dt, J=8.9, 6.7 Hz, 1H) |
| 3.68 | (dt, J=8.9, 6.3 Hz, 1H) |
| 4.01 | (t, J=6.6 Hz, 2H) |
| 4.18 | (ddd, J=1.6, 3.0, 9.3 Hz, 1H) |
| 4.25 | (dq, J=9.2, 5.8 Hz, 1H) |
| 5.97 | (ddd, J=1.8, 2.8, 10.3 Hz, 1H) |
| 6.18–6.23 | (m, 1H) |
| 6.59–6.60 | (m, 1H) |
| 6.99 | (d, J=8.7 Hz, 2H) |
| 7.42 | (d, J=8.8 Hz, 2H) |
| 7.62 | (d, J=8.5 Hz, 2H) |
| 8.09 | (d, J=8.4 Hz, 2H) |

$^{19}$F-NMR (reference compound: CF Cl$_3$); δ(ppm)

| -76.28 | (d, J=5.8 Hz) |
|---|---| mass analysis m/e (M$^+$+H) calculated 548.2750 found 548.2772

EXAMPLE 3

Synthesis of (2S,5S,6S)-2H-5,6-dihydro-6-trifluoromethyl-2-(4"-hexyloxybiphenyl-4"-carbonyloxy)-5-tert-butyldimethylsiloxypyran and (2R,5S,6S)-2H-5,6-dihydro-6-trifluoromethyl-2-(4"-hexyloxybiphenyl-4'-carbonyloxy)-5-tert-butyldimethylsiloxypyran

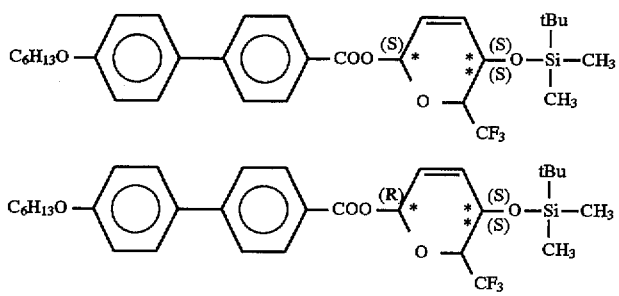

In the above formula, tBu represents a tert-butyl group.

In accordance with the same procedures as those used in Example 1 except that 0.50 g (1.68 mmol) of (5S,6S)-2H-5,6-dihydro-5-tert-butyldimethylsiloxy-6-trifluoromethyl-2-hydroxypyran obtained in Reference Example 1 and 0.64 g (2.01 mmol) of 4'-hexyloxy-4-biphenylcarboxylic acid chloride were used, the object compounds were obtained as follows: (2S,5S,6S)-2H-5,6-dihydro6-trifluoromethyl-2-(4"-hexyloxybiphenyl-4'-carbonyloxy)-5-tert-butyldimethylsiloxypyran in an amount of 0.45 g (0.78 mmol) and (2R,5S,6S)-2H-5,6-dihydro-6-trifluoromethyl-2-(4"-hexyloxybiphenyl-4'-carbonyloxy)-5-tert-butyl-dimethylsiloxypyran in an amount of 0.09 g (0.15 mmol).

Physical properties of the obtained compounds are shown in the following.

(1) The (2S,5S,6S) isomer

Molecular formula: C$_{31}$H$_{41}$O$_5$F$_3$Si $^1$H-NMR; δ(ppm)

| 0.13 | (s, 3H) |
|---|---|
| 0.15 | (s, 3H) |
| 0.89–0.94 | (m, 12H) |
| 1.26–1.57 | (m, 6H) |
| 1.75–1.83 | (m, 2H) |
| 4.01 | (t, J=6.6 Hz, 2H) |
| 4.22 | (dq, J=4.2, 7.6 Hz, 1H) |
| 4.42–4.46 | (m, 1H) |
| 5.98 | (ddd, J=1.2, 2.2, 10.4 Hz, 1H) |
| 6.10 | (ddd, J=1.3, 3.7, 10.4 Hz, 1H) |
| 6.68 | (m, 1H) |
| 6.99 | (d, J=8.8 Hz, 2H) |
| 7.56 | (d, J=8.7 Hz, 2H) |
| 7.63 | (d, J=8.6 Hz, 2H) |
| 8.09 | (d, J=8.4 Hz, 2H) |

$^{19}$F-NMR (reference compound: CF Cl$_3$); δ(ppm)

| -74.88 | (d, J=7.5 Hz) |
|---|---|

[α]$^{26}$D=+133.3° (C.(concentration)=0.99, solvent: chloroform)

mass analysis m/e (M$^+$+H) calculated 578.2676 found 578.2646

(2) The (2R,5S,6S) isomer

Molecular formula: C$_{31}$H$_{41}$O$_5$F$_3$Si $^1$H-NMR; δ(ppm)

| 0.12 | (s, 3H) |
|---|---|
| 0.16 | (s, 3H) |
| 0.84–1.00 | (m, 12H) |
| 1.26–1.56 | (m, 5H) |
| 1.76–1.87 | (m, 2H) |
| 4.01 | (t, J=6.6 Hz, 2H) |
| 4.18 | (dq, J=8.9, 6.2 Hz, 2H) |
| 4.53–4.57 | (m, 1H) |
| 5.91 | (ddd, J=2.3, 2.3, 10.3 Hz, 1H) |
| 6.01–6.05 | (m, 1H) |
| 6.58 | (m, 1H) |
| 6.99 | (d, J=8.8 Hz, 2H) |
| 7.56 | (d, J=8.8 Hz, 2H) |
| 7.64 | (d, J=8.5 Hz, 2H) |
| 8.11 | (d, J=8.4 Hz, 2H) |

$^{19}$F-NMR (reference compound: CF Cl$_3$); δ(ppm)

| -75.27 | (d, J=6.2 Hz) |
|---|---| mass analysis m/e (M$^+$+H) calculated 578.2676 found 578.2685

EXAMPLE 4

Synthesis of (2S,5S,6S)-2H-5,6-dihydro-2-hexyloxy-6-trifluoromethyl-5-(4"-hexyloxybiphenyl-4'-carbonyloxy)pyran

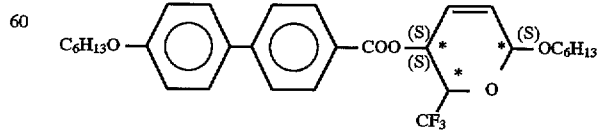

In accordance with the same procedures as those used in Example 1 except that 0.50 g (1.86 mmol) of (2S,5S,6S)-

2H-5,6-dihydro-6-trifluoromethyl-2-hexyloxy-5-hydroxypyran obtained in Reference Example 2, and 0.67 g (2.23 mmol) of 4'-hexyloxy-4-biphenylcarboxylic acid chloride were used, the object compound was obtained as follows: (2S,5S,6S)-2H-5,6-dihydro-2-hexyloxy-6-trifluoromethyl-5-(4"-hexyloxy -biphenyl-4'-carbonyloxy) pyran in an amount of 0.42 g (0.17 mmol).

Physical properties of the obtained compound are shown in the following.

Molecular formula: $C_{31}H_{39}O_5F_3$ $^1$H-NMR; δ(ppm)

| | |
|---|---|
| 0.88~0.93 | (m, 6H) |
| 1.25~1.84 | (m, 16H) |
| 3.57 | (dt, J=9.5, 6.5 Hz, 1H) |
| 3.86 | (dt, J=9.5, 6.7 Hz, 1H) |
| 4.01 | (t, J=6.5 Hz, 2H) |
| 4.51 | (dq, J=9.4, 6.1 Hz, 1H) |
| 5.15 | (m, 1H) |
| 5.86~6.01 | (m, 3H) |
| 6.98 | (d, J=8.7 Hz, 2H) |
| 7.56 | (d, J=8.7 Hz, 2H) |
| 7.62 | (d, J=8.3 Hz, 2H) |
| 8.06 | (d, J=8.3 Hz, 2H) |

$^{19}$F-NMR (reference compound: CF Cl$_3$); δ(ppm)

| | |
|---|---|
| −76.83 | (d, J=6.2 Hz) |

$[α]^{25}$D=+118.59° (C.(concentration)=1.10, solvent: chloroform)

mass analysis m/e (M$^+$+H) calculated 548.2750 found 548.2766

EXAMPLE 5

A base liquid crystal A containing 25 % by weight each of the following compounds:

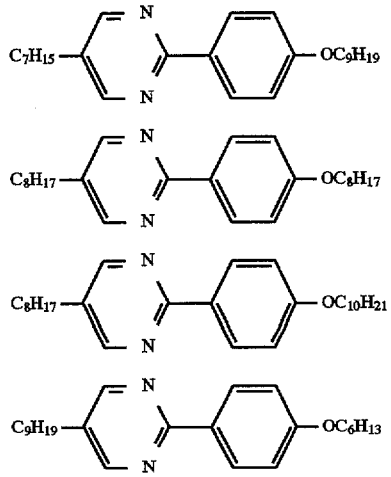

was prepared. The optically active dihydropyran derivative synthesized in Example 1 was mixed with the obtained base liquid crystal A in such an amount that the content of the optically active dihydropyran derivative is 2% by weight to prepare a liquid crystal composition.

The obtained liquid crystal composition had the following phase transition temperatures:

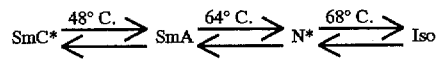

wherein

SmC*: ferroelectric chiral smectic C phase

SmA: smectic A phase

N*: chiral nematic phase

Iso: isotropic liquid state

The thus prepared liquid crystal composition was injected at an isotropic phase into a liquid crystal cell of 2.0 μm gap having alignment films of polyimide treated with parallel rubbing. The liquid crystal composition was cooled slowly and aligned. The combined liquid crystal device showed a response time ($τ_{0-90}$) of 147 μsecond at 30° C. under the application of a rectangular voltage of $V_{pp}$=20 V. The response time was obtained as the time elapsed in changing the intensity of the transmitted light from 0 to 90% under crossed nicols. The liquid crystal device also showed a spontaneous polarization of 2.4 nC/cm$^2$ by the measurement in accordance with the triangular wave method.

EXAMPLE 6

The optically active dihydropyran derivative synthesized in Example 2 was mixed with the base liquid crystal A obtained in Example 5 in such an amount that the content of the optically active dihydropyran derivative was 2% by weight to prepare a liquid crystal composition.

The obtained liquid crystal composition had the following phase transition temperatures:

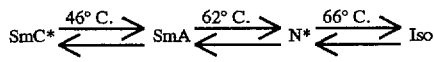

The thus prepared liquid crystal composition was injected at isotropic phase into a liquid crystal cell of 1.9 μm gap having alignment films of polyimide treated with parallel rubbing. The liquid crystal composition was cooled slowly and aligned. The combined liquid crystal device showed a response time ($τ_{0-90}$) of 79 μsecond at 30° C. under the application of a rectangular voltage of $V_{pp}$=19 V. The liquid crystal device also showed a spontaneous polarization of 6.6 nC/cm$^2$ by the measurement in accordance with the triangular wave method.

EXAMPLE 7

The optically active dihydropyran derivative having (2S, 5S,6S) asymmetric carbons which was synthesized in Example 3 was mixed with the base liquid crystal A obtained in Example 5 in such an amount that the content of the optically active dihydropyran derivative was 2% by weight to prepare a liquid crystal composition.

The obtained liquid crystal composition had the following phase transition temperatures:

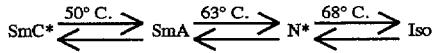

The thus prepared liquid crystal composition was injected at isotropic phase into a liquid crystal cell of 1.9 μm gap having alignment films of polyimide treated with parallel rubbing. The liquid crystal composition was cooled slowly and aligned. The combined liquid crystal device showed a response time ($τ_{0-90}$) of 92 μsecond at 30° C. under the application of a rectangular voltage of $V_{pp}=19$ V. The liquid crystal device also showed a spontaneous polarization of 5.3 $nC/cm^2$ by the measurement in accordance with the triangular wave method.

EXAMPLE 8

The optically active dihydropyran derivative having (2R, 5S,6S) asymmetric carbons which was synthesized in Example 3 was mixed with the base liquid crystal A obtained in Example 5 in such an amount that the content of the optically active dihydropyran derivative was 2% by weight to prepare a liquid crystal composition.

The obtained liquid crystal composition had the following phase transition temperatures:

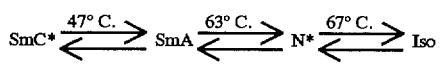

The thus prepared liquid crystal composition was injected at isotropic phase into a liquid crystal cell of 1.9 μm gap having alignment films of polyimide treated with parallel rubbing. The liquid crystal composition was cooled slowly and aligned. The combined liquid crystal device showed a response time ($\tau_{0-90}$) of 89 μsecond at 30° C. under the application of a rectangular voltage of $V_{pp}=19$ V. The liquid crystal device also showed a spontaneous polarization of 4.6 $nC/cm^2$ by the measurement in accordance with the triangular wave method.

EXAMPLE 9

The optically active dihydropyran derivative synthesized in Example 4 was mixed with the base liquid crystal A obtained in Example 5 in such an amount that the content of the optically active dihydropyran derivative was 2% by weight to prepare a liquid crystal composition.

The obtained liquid crystal composition had the following phase transition temperatures:

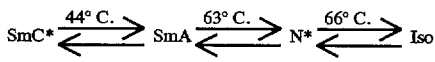

The thus prepared liquid crystal composition was injected at isotropic phase into a liquid crystal cell of 1.8 μm gap having alignment films of polyimide treated with parallel rubbing. The liquid crystal composition was cooled slowly and aligned. The combined liquid crystal device showed a response time ($\tau_{0-90}$) of 102 μsecond at 30° C. under the application of a rectangular voltage of $V_{pp}=18$ V. The liquid crystal device also showed a spontaneous polarization of 3.4 $nC/cm^2$ by the measurement in accordance with the triangular wave method.

EXAMPLE 10

A base liquid crystal B containing 17.5% by weight each of the following compounds:

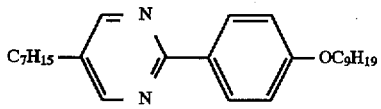

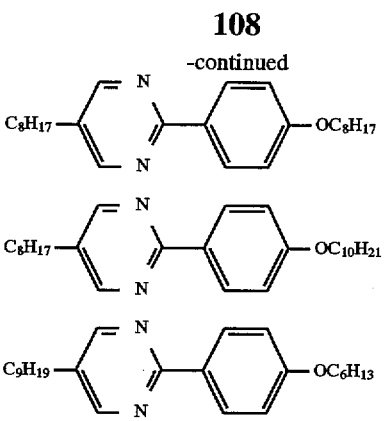

and 30.0% by weight of the following compound:

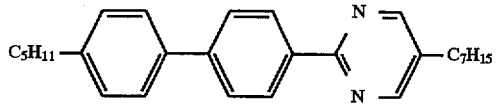

was prepared. The optically active dihydropyran derivative synthesized in Example 2 was mixed with the obtained base liquid crystal B in such an amount that the content of the optically active dihydropyran derivative is 5 % by weight to prepare a liquid crystal composition.

The obtained liquid crystal composition had phase transition temperatures as shown in the following:

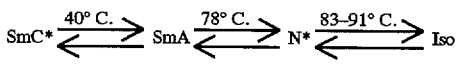

The thus prepared liquid crystal composition was injected at isotropic phase into a liquid crystal cell of 1.7 μm gap having alignment films of polyimide treated with parallel rubbing. The liquid crystal composition was cooled slowly and aligned. The combined liquid crystal device showed a response time ($\tau_{0-90}$) of 51 μsecond at 30° C. under the application of a rectangular voltage of $V_{pp}=17$ V. The response speed was obtained as the time elapsed in changing the intensity of the transmitted light from 0 to 90% under crossed nicols. The liquid crystal device also showed a spontaneous polarization of 8.1 $nC/cm^2$ by the measurement in accordance with the triangular wave method.

EXAMPLE 11

The optically active dihydropyran derivative having (2S, 5S,6S) asymmetric carbons which was synthesized in Example 3 was mixed with the base liquid crystal B obtained in Example 10 in such an amount that the content of the optically active dihydropyran derivative was 5% by weight to prepare a liquid crystal composition.

The obtained liquid crystal composition had the following phase transition temperatures:

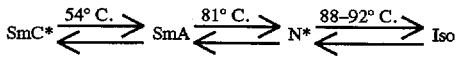

The thus prepared liquid crystal composition was injected at isotropic phase into a liquid crystal cell of 1.8 μm gap having alignment films of polyimide treated with parallel rubbing. The liquid crystal composition was cooled slowly and aligned. The combined liquid crystal device showed a response time ($\tau_{0-90}$) of 58 μsecond at 30° C. under the application of a rectangular voltage of $V_{pp}$=18 V. The liquid crystal device also showed a spontaneous polarization of 9.6 nC/cm$^2$ by the measurement in accordance with the triangular wave method.

What is claimed is:

1. A 2H-5,6-optically active dihydropyran derivative represented by the general formula (I) or (I'):

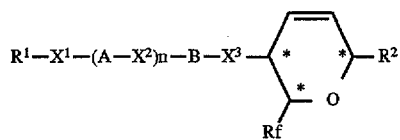  (I)

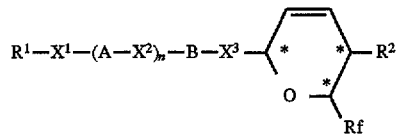  (I')

wherein Rf represents a fluoroalkyl group having 1 or 2 carbon atoms, R$^1$ represents a linear or branched alkyl group having 1 to 20 carbon atoms, R$^2$ represents a substituent group represented by the general formula (II):

  (II)

wherein X$^4$ represents —O— or —OCO—, and R$^3$ represents hydrogen, a linear or branched alkyl group having 1 to 15 carbon atoms, an alkenyl group having 2 to 15 carbon atoms, or an aralkyl group having 7 to 10 carbon atoms, X$^1$ represents —COO—, —OCO—, —O—, or a single bond, X$^2$ represents —COO—, —OCO—, —CH$_2$O—, —OCH$_2$—, —C=C—, or a single bond, X$^3$ represents —COO—, —CH$_2$O—, or —O—, * represents asymmetry of a carbon, A and B represent each independently a substituted or unsubstituted group containing a six-membered ring, and n represents 0 or 1.

2. A liquid crystal composition comprising:

(a) at least one type of the 2H-5,6-optically active dihydropyran derivative described in claim 1, (b) a compound or a mixture having a chiral smectic C phase (SmC*) excluding the optically active dihydropyran derivative used in (a), and/or (c) a compound or a mixture having a smectic C phase (SmC) excluding the optically active dihydropyran derivative used in (a).

3. A liquid crystal composition comprising at least two types of the 2H-5,6-optically active dihydropyran derivative described in claim 1.

4. A liquid crystal device comprising the 2H-5,6-optically active dihydropyran derivative described in claim 1, the liquid crystal composition described in claim 2, or the liquid crystal composition described in claim 3, which is disposed between a pair of electrode plates.

5. A racemic mixture comprising at least one type of the 2H-5,6-optically active dihydropyran derivative described in claim 1.

6. The 2H-5,6-optically active dihydropyran derivative as claimed in claim 1, having the formula:

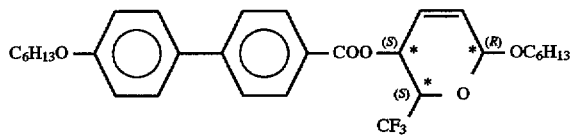

* * * * *